United States Patent
Lan et al.

(10) Patent No.: US 9,890,168 B2
(45) Date of Patent: Feb. 13, 2018

(54) 2,4-DISUBSTITUTED 7H-PYRROLO[2,3-D]PYRIMIDINE DERIVATIVE, PREPARATION METHOD AND MEDICINAL USE THEREOF

(71) Applicants: Shanghai Haiyan Pharmaceutical Technology Co., Ltd., Shanghai (CN); Yangtze River Pharmaceutical Group Co., Ltd., Jiangsu (CN)

(72) Inventors: Jiong Lan, Shanghai (CN); Yunzhou Jin, Shanghai (CN); Fusheng Zhou, Shanghai (CN); Jing Lei, Shanghai (CN); Chong Wen, Shanghai (CN); Zhiyuan Zhang, Shanghai (CN); Xiangyu He, Shanghai (CN)

(73) Assignees: Shanghai Haiyan Pharmaceutical Technology Co., Ltd., Shanghai (CN); Yangtze River Pharmaceutical Group Co., Ltd., Jiangsu (CN)

( * ) Notice: Subject to any disclaimer, the term of this patent is extended or adjusted under 35 U.S.C. 154(b) by 0 days.

(21) Appl. No.: 15/329,183

(22) PCT Filed: Jul. 24, 2015

(86) PCT No.: PCT/CN2015/085089
§ 371 (c)(1),
(2) Date: Jan. 25, 2017

(87) PCT Pub. No.: WO2016/011979
PCT Pub. Date: Jan. 28, 2016

(65) Prior Publication Data
US 2017/0233395 A1    Aug. 17, 2017

(30) Foreign Application Priority Data
Jul. 25, 2014  (CN) .......................... 2014 1 0361024

(51) Int. Cl.
*C07D 487/04* (2006.01)
*A61K 31/519* (2006.01)
*C07D 519/00* (2006.01)
*A61P 35/02* (2006.01)
*A61K 45/06* (2006.01)
*A61K 31/5377* (2006.01)

(52) U.S. Cl.
CPC .......... *C07D 487/04* (2013.01); *A61K 31/519* (2013.01); *A61K 31/5377* (2013.01); *A61K 45/06* (2013.01); *C07D 519/00* (2013.01)

(58) Field of Classification Search
CPC ... C07D 495/04; A61K 31/519; D07D 487/04
USPC .......... 544/278, 105, 280; 514/260.1, 230.5, 514/265.1
See application file for complete search history.

(56) References Cited

FOREIGN PATENT DOCUMENTS

| CN | 103501612 A | 1/2014 |
|---|---|---|
| WO | 2011140338 A1 | 11/2011 |
| WO | 2013169401 A1 | 11/2013 |

OTHER PUBLICATIONS

Stella (J. Pharmaceutical Sciences, 2010, 99(12), pp. 4755-4765).*
Int'l Search Report dated Oct. 14, 2015 in Int'l Application No. PCT/CN2015/085089.

* cited by examiner

*Primary Examiner* — Susanna Moore
(74) *Attorney, Agent, or Firm* — Panitch Schwarze Belisario & Nadel LLP

(57) ABSTRACT

The present invention relates to a 2,4-disubstituted 7H-pyrrolo[2,3-d]pyrimidine derivative, a preparation method and a medicinal use thereof. In particular, the present invention discloses a compound of formula (I) or a pharmaceutically acceptable salt, stereoisomer, solvate or prodrug thereof, and a preparation method and use thereof. For the definition of each group in formula (I), see the description tbr details.

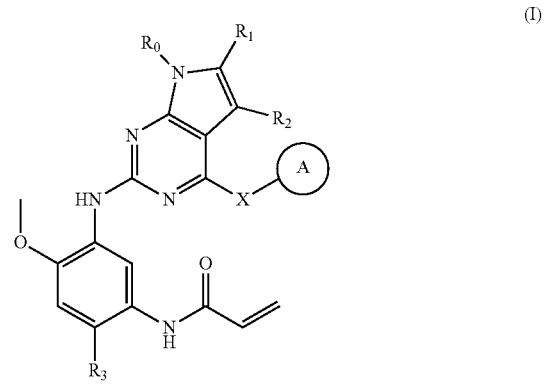

20 Claims, No Drawings

2,4-DISUBSTITUTED 7H-PYRROLO[2,3-D]PYRIMIDINE DERIVATIVE, PREPARATION METHOD AND MEDICINAL USE THEREOF

CROSS-REFERENCE TO RELATED APPLICATION

This application is a Section 371 of International Application No. PCT/CN2015/085089, filed Jul. 24, 2015, which was published in the Chinese language on Jan. 28, 2016, under International Publication No. WO 2016/011979 A1, and the disclosure of which is incorporated herein by reference.

TECHNICAL FIELD

The present invention relates to the field of medical technology, in particular to a 2,4-disubstituted 7H-pyrrolo [2,3-d]pyrimidine derivative, preparation method thereof and use as an EGFR tyrosine kinase inhibitor, as well as pharmaceutical compositions and medicinal compositions prepared therefrom.

BACKGROUND ART

Lung cancer is a cancer having the highest incidence in the world. In China, the incidence of lung cancer ranks first among all cancers and it is also a cancer having the highest morbidity and mortality.

In Chinese patients with lung cancer, 30% of patients have the EGFR mutation, wherein L858R and exon 19 deletion mutations account for more than 90% and these patients are more sensitive to EGFR inhibitors. The existing first generation EGER inhibitors in market such as erlotinib and gefitinib have good treatment effects on these patients and can make the tumors of more than 60% of the patients shrink, thereby significantly prolonging the progression-free survival of patients. However, drug resistance develops within 6-12 months for the overwhelming majority of patients, and the first generation EGFR inhibitors are no longer effective, while no drugs are available to these patients currently. It has been found in clinic that EGFR T790M mutation was present in 50% of the patients who developed resistance to the first-generation EGFR inhibitors. The first-generation EGFR inhibitors, erlotinib and gefitinib, were greater than 3 uM in the T790M mutant cell line H1975 and almost have no activity.

Currently the second-generation irreversible pan-EGER inhibitor, alfatinib, has been approved for the market. This drug has significantly better treatment effect on patients with EGFR mutation lung cancer compared with the first-generation EGFR inhibitors. However, the second-generation inhibitors also have a strong inhibitory activity on wild-type EGFR. The inhibitory activity on wild-type EGFR is significantly higher than that on the resistant T790M mutation. The side effects such as rash and the like were serious and it has poor treatment effect on drug-resistant patients. Only a small proportion of the patients resistant to first-generation EGFR inhibitors respond to this drug.

In order to increase the inhibitory activity against EGFR T790M resistance mutant while reducing the inhibitory activity against wild-type EGFR, developing third-generation EGFR mutant selective inhibitors with higher activity, better selectivity and lower toxicity is of great significance.

SUMMARY OF THE INVENTION

The object of the present invention is to provide a 2,4-disubstituted 7H-pyrrolo[2,3-d]pyrimidine derivative, which not only has higher it activity against EGFR T790M drug-resistant mutation and sensitive mutations (e.g., L858R mutation or exon 19 deletion) but also exhibits significantly reduced inhibitory activity against wild type EGFR, thus having higher selective inhibition, and it has low cytotoxicity. Moreover, the compounds of the present invention also exhibit advantageous physical properties, toxic characteristics and/or metabolic characteristics in comparison with other known EGFR mutant inhibitors.

In the first aspect of the present invention, a compound represented by formula (I), or a pharmaceutically acceptable salt, solvate, stereoisomer, or prodrug thereof is provided,

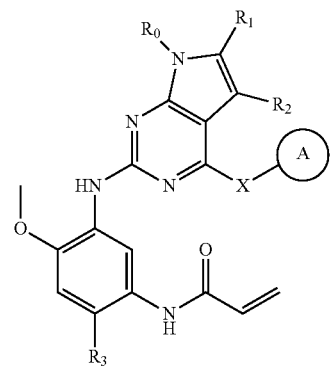

I wherein,

A ring is substituted or unsubstituted $C_{3-10}$ heterocyclic radical, substituted or unsubstituted $C_{6-10}$ aryl ring or substituted or unsubstituted $C_{4-10}$ cycloalkenyl;

said "substituted" means that 1-6 hydrogen atoms on the ring atoms are substituted with substituents selected from the group consisting of: hydroxy, CN, $NO_2$, halogen, $C_{1-3}$ alkyl, $C_{1-3}$ haloalkyl, —CON($C_{1-3}$ alkyl)$_2$, —C(O)O$C_{1-3}$ alkyl, —OC(O)$C_{1-3}$ alkyl, —CO$C_{1-3}$ alkyl, —CO-phenyl, —SO$_2C_{1-3}$ alkyl, —SO$_2$-phenyl, —S(O)$C_{1-3}$ alkyl, —S(O)-phenyl, —N($C_{1-3}$ alkyl)$_2$;

X is a covalent bond, or NH, O or S;

$R_0$ is H, $C_{1-3}$ alkyl, $C_{1-3}$ haloalkyl, $C_{3-6}$ cycloalkyl, $C_{3-6}$ halocycloalkyl, —CHO, —CO$C_{1-3}$ alkyl, —CO-phenyl, —SO$_2C_{1-3}$ alkyl, —SO$_2$-phenyl;

$R_1$ and $R_2$ are each independently H, halogen, $C_{1-3}$ alkyl, $C_{1-3}$ haloalkyl;

$R_3$ is selected from the group consisting of:

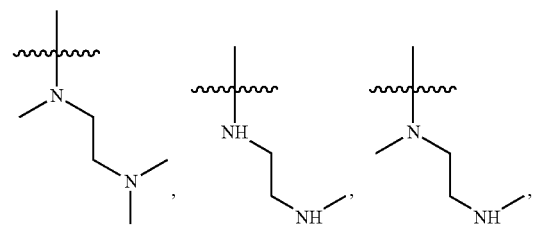

-continued

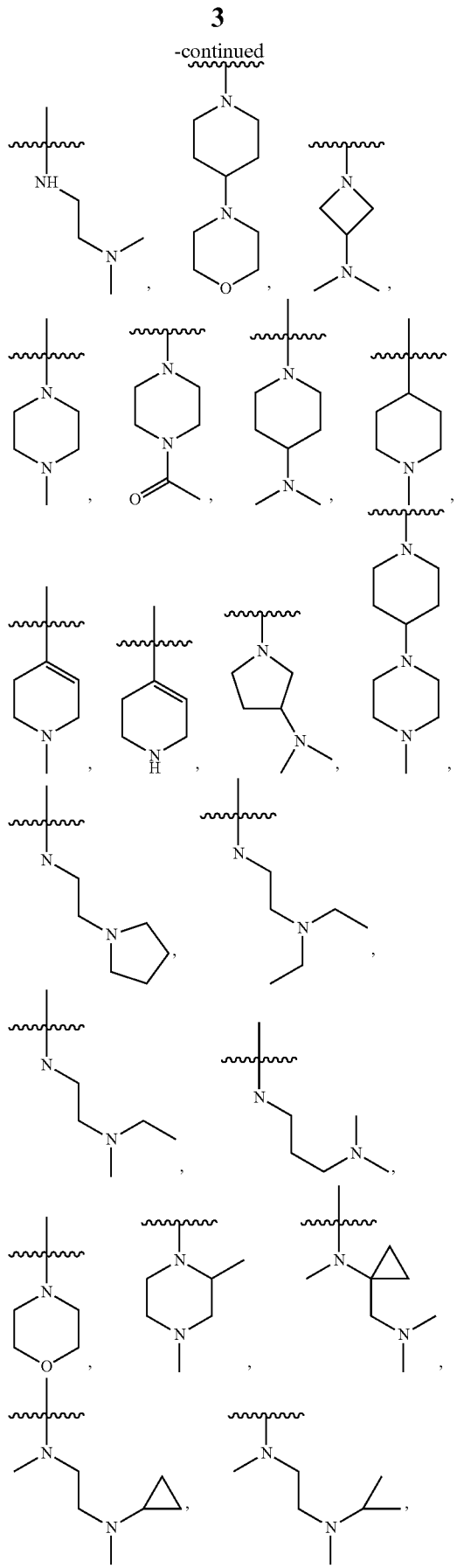

-continued

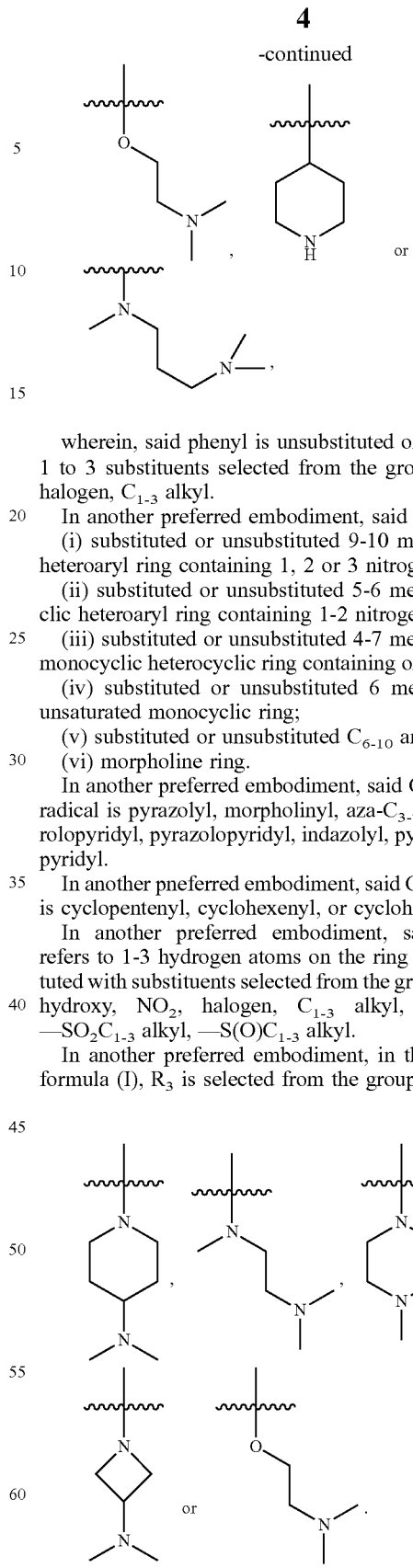

wherein, said phenyl is unsubstituted or substituted with 1 to 3 substituents selected from the group consisting of: halogen, $C_{1-3}$ alkyl.

In another preferred embodiment, said A ring is:
(i) substituted or unsubstituted 9-10 membered bicyclic heteroaryl ring containing 1, 2 or 3 nitrogen atoms;
(ii) substituted or unsubstituted 5-6 membered monocyclic heteroaryl ring containing 1-2 nitrogen atoms;
(iii) substituted or unsubstituted 4-7 meinbered saturated monocyclic heterocyclic ring containing one nitrogen atom;
(iv) substituted or unsubstituted 6 membered partially unsaturated monocyclic ring;
(v) substituted or unsubstituted $C_{6-10}$ aryl ring; or
(vi) morpholine ring.

In another preferred embodiment, said $C_{3-10}$ heterocyclic radical is pyrazolyl, morpholinyl, aza-$C_{3-7}$ cycloalkyl, pyrrolopyridyl, pyrazolopyridyl, indazolyl, pyrrolyl, indolyl, or pyridyl.

In another pneferred embodiment, said $C_{4-10}$ cycloalkenyl is cyclopentenyl, cyclohexenyl, or cycloheptenyl.

In another preferred embodiment, said "substituted" refers to 1-3 hydrogen atoms on the ring atoms are substituted with substituents selected from the group consisting of: hydroxy, $NO_2$, halogen, $C_{1-3}$ alkyl, $C_{1-3}$ haloalkyl, $—SO_2C_{1-3}$ alkyl, $—S(O)C_{1-3}$ alkyl.

In another preferred embodiment, in the compounds of formula (I), $R_3$ is selected from the group consisting of:

In another preferred embodiment, in the compounds of founula (I), $R_0$ is H, methyl, ethyl, propyl, isopropyl, cyclopropyl, cyclobutyl, cyclopentyl, cyclohexyl, monofluoroethyl, difluoromethyl, trifluoromethyl, —COCH$_3$, —CO-phenyl, —SO$_2$CH$_3$ or —SO$_2$-phenyl; said phenyl is unsubstituted or substituted with 1 to 3 substituents selected from the group consisting of: fluorine, chlorine, bromine, methyl, ethyl.

In another preferred embodiment, in the compounds of formula (I), $R_1$, $R_2$ are each independently H, fluorine, chlorine, bromine, methyl, ethyl, propyl, isopropyl, monofluomethyl, difluoromethyl, trifluoromethyl.

In another preferred embodiment, in the compounds of formula (I), said substituted or unsubstituted C$_{3-10}$ heterocyclic radical is substituted or unsubstituted 9-10 membered bicyclic heteroaryl ring containing 1, 2 or 3 nitrogen atoms and is selected from the group consisting of:

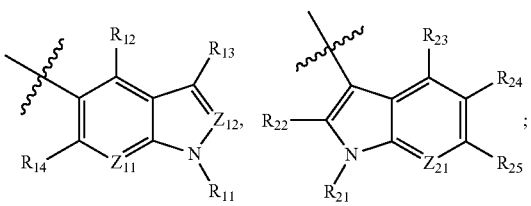

wherein, $Z_{11}$ is CR$_{15}$ or N; $Z_{12}$ is CR$_{16}$ or N; $Z_{21}$ is CR$_{26}$ or N;

$R_{12}$, $R_{13}$, $R_{14}$, $R_{15}$, $R_{16}$, $R_{22}$, $R_{23}$, $R_{24}$, $R_{25}$, and $R_{26}$ are each independently H, hydroxy, CN, NO$_2$, halogen, C$_{1-3}$ haloalkyl, C$_{1-3}$ alkyl, —CON(C$_{1-3}$ alkyl)$_2$, —N(C$_{1-3}$ alkyl)$_2$, —C(O)OC$_{1-3}$ alkyl, —OC(O)C$_{1-3}$ alkyl, —COC$_{1-3}$ alkyl, —CO-phenyl, —SO$_2$C$_{1-3}$ alkyl, —SO$_2$-phenyl, —S(O)C$_{1-3}$ alkyl, —S(O)-phenyl; said alkyl and phenyl are unsubstituted or substituted with 1 to 3 substituents selected from the group consisting of: fluorine, chlorine, methyl;

$R_{11}$ and $R_{21}$ are each independently H, C$_{1-3}$ haloalkyl, C$_{1-3}$ alkyl, —COC$_{1-3}$ alkyl, —CO-phenyl, —SO$_2$C$_{1-3}$ alkyl, —SO$_2$-phenyl. Said phenyl is unsubstituted or substituted with 1 to 3 substituents selected from the group consisting of: fluorine, chlorine, methyl.

In another preferred embodiment, $Z_{11}$ is N; $Z_{12}$ is CR$_{16}$; $R_{12}$, $R_{13}$, $R_{14}$, and $R_{16}$ are each independently H, halogen, C$_{1-3}$ haloalkyl, C$_{1-3}$ alkyl; $R_{11}$ is H, C$_{1-3}$ haloalkyl, C$_{1-3}$ alkyl, —COC$_{1-3}$ alkyl, —SO$_2$C$_{1-3}$ alkyl.

In another preferred embodiment, $Z_{11}$ is N; $Z_{12}$ is CR$_{16}$; $R_{12}$, $R_{13}$, $R_{14}$, and $R_{16}$ are each independently H, fluorine, chlorine, bromine, methyl, ethyl, propyl, isopropyl, monofluoroethyl, difluoromethyl, trifluoromethyl; $R_{11}$ is H, methyl, ethyl, propyl, isopropyl, monofluoroethyl, difluoromethyl, trifluoromethyl, —COCH$_3$, —SO$_2$CH$_3$.

In another preferred embodiment, $Z_{21}$ is CR$_{26}$; $R_{22}$, $R_{23}$, $R_{24}$, $R_{25}$, and $R_{26}$ are each independently H, halogen, C$_{1-3}$ haloalkyl, C$_{1-3}$ alkyl; $R_{21}$ is H, C$_{1-3}$ haloalkyl, C$_{1-3}$ alkyl, —COC$_{1-3}$ alkyl, —SO$_2$C$_{1-3}$ alkyl.

In another preferred embodiment, $Z_{21}$ is CR$_{26}$; $R_{22}$, $R_{23}$, $R_{24}$, $R_{25}$, and $R_{26}$ are each independently H, fluorine, chlorine, bromine, methyl, ethyl, propyl, isopropyl, monofluoroethyl, difluoromethyl, trifluoromethyl; $R_{21}$ is H, methyl, ethyl, propyl, isopropyl, monofluoroethyl, difluoromethyl, trifluoromethyl, —COCH$_3$, —SO$_2$CH$_3$.

In another preferred embodiment, in the compounds of formula (I), said substituted or unsubstituted C$_{3-10}$ heterocyclic radical is substituted or unsubstituted 5-6 membered monocyclic heteroaryl ring containing 1-2 nitrogen atoms and is selected from the group consisting of:

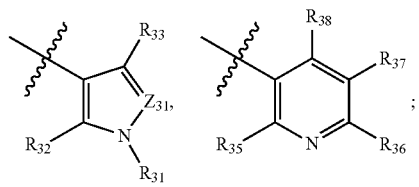

wherein, $Z_{31}$ is CR$_{34}$ or N;

$R_{32}$, $R_{33}$, $R_{34}$, $R_{35}$, $R_{36}$, $R_{37}$, and $R_{38}$ are each independently H, hydroxy, CN, NO$_2$, halogen, C$_{1-3}$ haloalkyl, C$_{1-3}$ alkyl, —CON(C$_{1-3}$ alkyl)$_2$, —N(C$_{1-3}$ alkyl)$_2$, —C(O)OC$_{1-3}$ alkyl, —OC(O)C$_{1-3}$ alkyl, —COC$_{1-3}$ alkyl, —CO-phenyl, —SO$_2$C$_{1-3}$ alkyl, —SO$_2$-phenyl, —S(O)C$_{1-3}$ alkyl, —S(O)-phenyl; said phenyl is unsubstituted or substituted with 1 to 3 substituents selected from the group consisting, of: fluorine, chlorine, methyl;

$R_{31}$ is H, C$_{1-3}$ haloalkyl, C$_{1-3}$ alkyl, —COC$_{1-3}$ alkyl, —CO-phenyl, —SO$_2$C$_{1-3}$ alkyl, —SO$_2$-phenyl; said phenyl is unsubstituted or substituted with 1 to 3 substituents selected from the group consisting of: fluorine, chlorine, methyl.

In another preferred embodiment, $Z_{31}$ is N; $R_{32}$ and $R_{33}$ are each independently H, halogen, C$_{1-3}$ haloalkyl, C$_{1-3}$ alkyl; $R_{31}$ is H, C$_{1-3}$ haloalkyl, C$_{1-3}$ alkyl, —COC$_{1-3}$ alkyl, —SO$_2$C$_{1-3}$ alkyl.

In another preferred embodiment, $Z_{31}$ is N; $R_{32}$ and $R_{33}$ are each independently H, fluorine, chlorine, bromine, methyl, ethyl, propyl, isopropyl, monofluoroethyl, difluoromethyl, trifluoromethyl; $R_{31}$ is H, methyl, ethyl, propyl, isopropyl, monofluoromethyl, difluoromethyl, trifluoromethyl, —COCH$_3$, —SO$_2$CH$_3$.

In another preferred embodiment, $R_{35}$, $R_{36}$, $R_{37}$, and $R_{38}$ are each independently, H, halogen, C$_{1-3}$ alkyl.

In another preferred embodiment, $R_{35}$, $R_{36}$, $R_{37}$, and $R_{38}$ are each independently H, fluorine, chlorine, bromine, methyl, ethyl, propyl, isopropyl.

In another preferred embodiment, in the compounds of formula (I), said substituted or unsubstituted C$_{3-10}$ heterocyclic radical is substituted or unsubstituted 4-7 membered saturated monocyclic heterocyclic ring containing one nitrogen atom and is selected from the group consisting of:

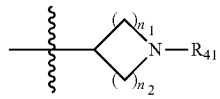

wherein, $n_1$ is 1, 2 or 3; $n_2$ is 1 or 2;

$R_{41}$ is H, C$_{1-3}$ alkyl, C$_{1-3}$ haloalkyl, —COC$_{1-3}$ alkyl, —CO-phenyl, —SO$_2$C$_{1-3}$ alkyl, —SO$_2$-phenyl, —S(O)C$_{1-3}$ alkyl, —S(O)-phenyl; said phenyl is unsubstituted or substituted with 1 to 3 substituents selected from the group consisting of: fluorine, chlorine, methyl.

In another preferred embodiment, $n_1$ is 1; $n_2$ is 1; $R_{41}$ is H, methyl, ethyl, propyl, isopropyl, monofluoroethyl, difluoromethyl, trifluoromethyl, —COCH$_3$, —SO$_2$CH$_3$, —SO$_2$-phenyl, —CO-phenyl; said phenyl is unsubstituted or substituted with one substituent selected from the group consisting of: fluorine, chlorine, methyl.

In another preferred embodiment, the compound of formula (I) is a compound represented by formula (II), formula (III), formula (IV), formula (V), or formula (VI):

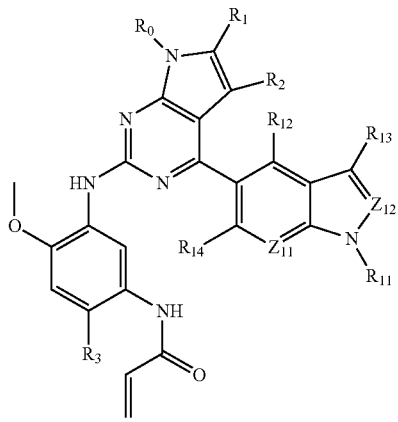

II wherein, $R_{11}$, $R_{12}$, $R_{13}$, $R_{14}$, $R_0$, $R_1$, $R_2$, $R_3$, $Z_{11}$, and $Z_{12}$ are defined as described in the specification;

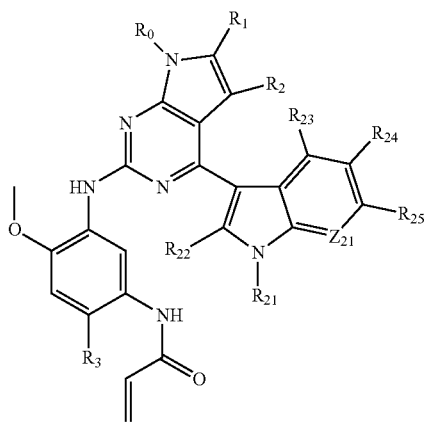

III wherein, $R_{21}$, $R_{22}$, $R_{23}$, $R_{24}$, $R_{25}$, $R_0$, $R_1$, $R_2$, $R_3$, and $Z_{21}$ are defined as described in the specification;

IV wherein, $R_{31}$, $R_{32}$, $R_{33}$, $R_0$, $R_1$, $R_2$, $R_3$, and $Z_{31}$ are defined as described in the specification;

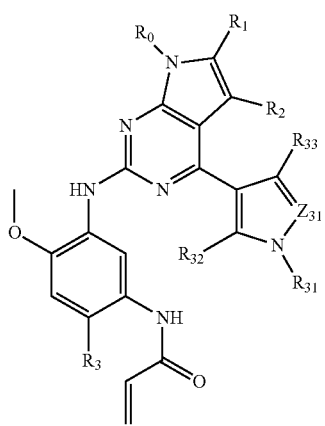

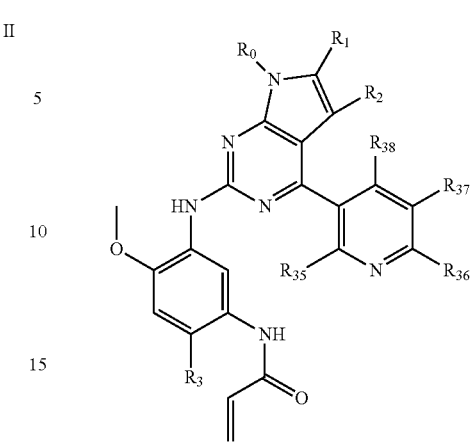

V wherein, $R_{35}$, $R_{36}$, $R_{37}$, $R_{38}$, $R_0$, $R_1$, $R_2$, and $R_3$ are defined as described in the specification;

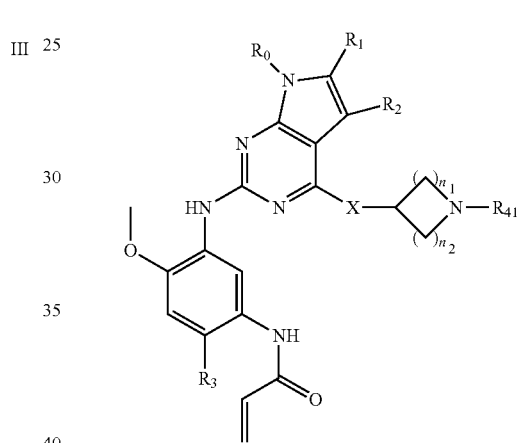

VI wherein, $R_{41}$, $R_0$, $R_1$, $R_2$, $R_3$, X, $n_1$, and $n_2$ are defined as described in the specification.

In another preferred embodiment, in the compounds of formula (VI), X is O.

In another preferred embodiment, the substituted or unsubstituted $C_{3-10}$ heterocyclic radical is selected from:

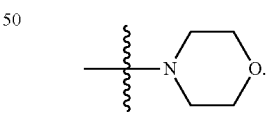

In another preferred embodiment, the substituted or unsubstituted $C_{6-10}$ aryl ring is selected from:

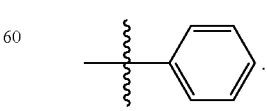

In another preferred embodiment, the compound of formula (I) is a compound represented by formula (VII) or formula (VIII):

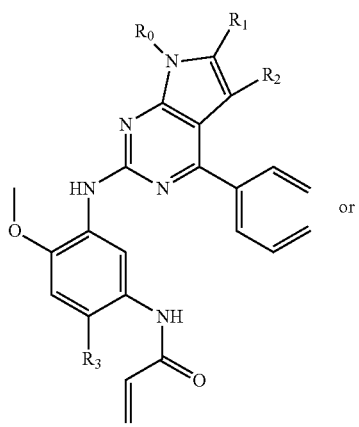

VII

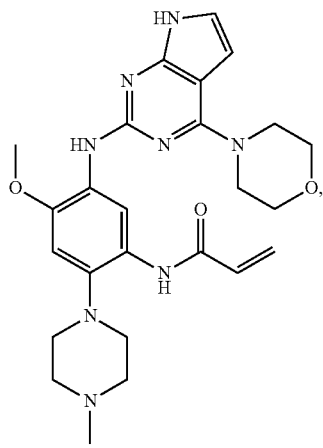

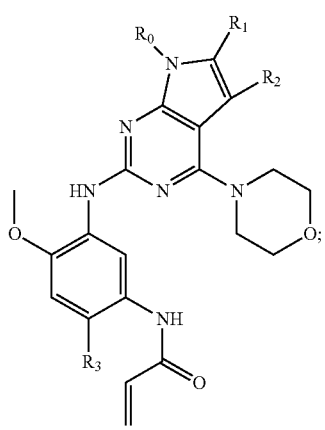

VIII wherein, $R_0$, $R_1$, $R_2$, and $R_3$ are defined as described in the specification.

In another preferred embodiment, in formula I, said $R_0$, $R_1$, $R_2$, $R_3$, X, and A ring are each independently the corresponding groups in each specific compound in the examples.

In another preferred embodiment, said compound of formula (I) comprises the compounds prepared in the examples, for example, is selected from the group consisting of:

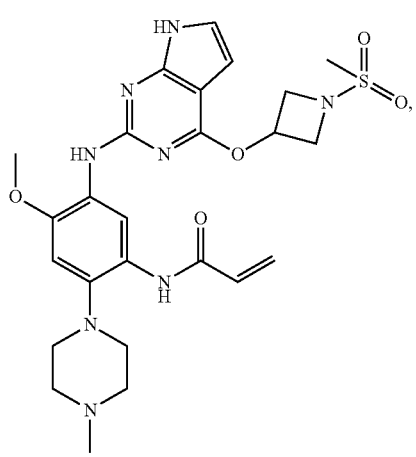

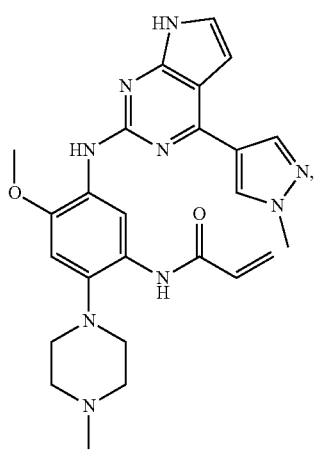

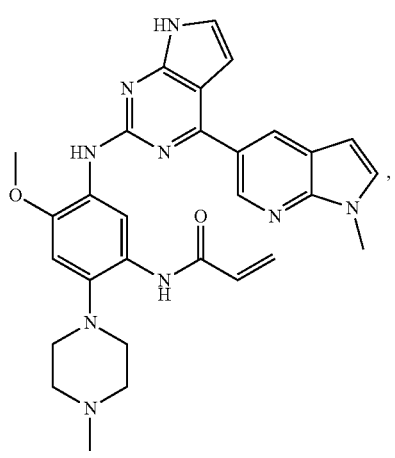

11
-continued
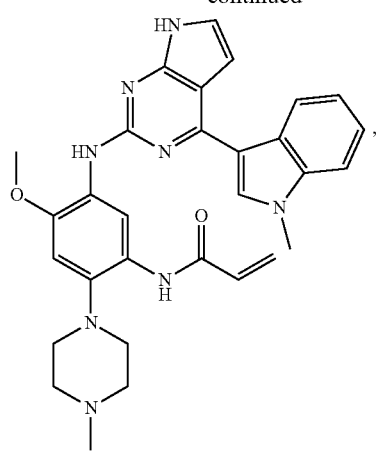
,
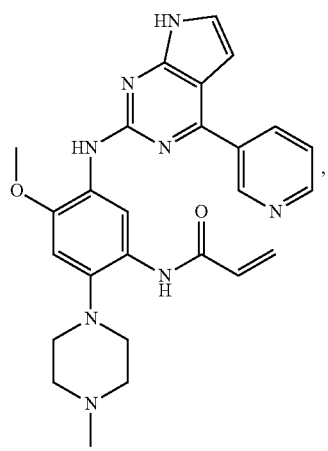
,
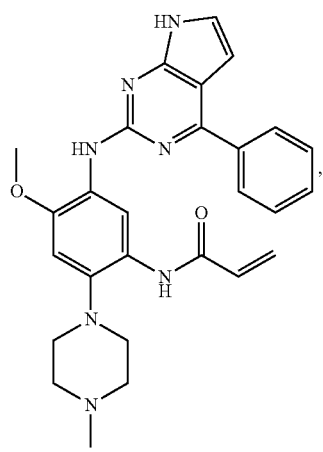
,
12
-continued
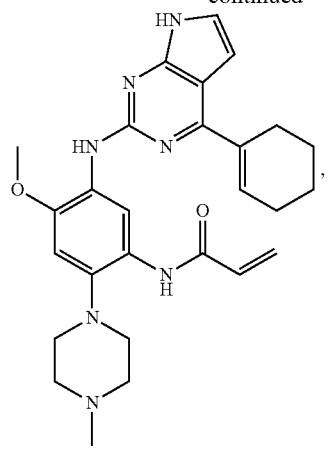
,
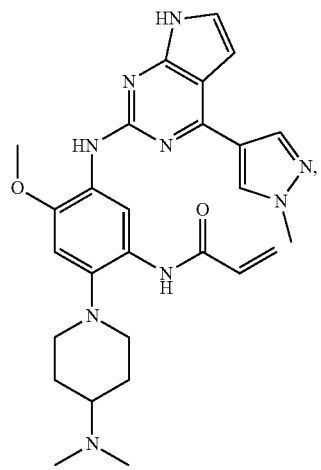
,
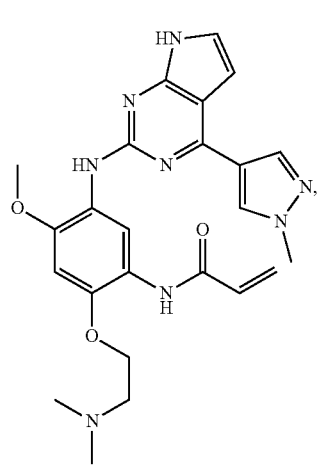
, 13
-continued
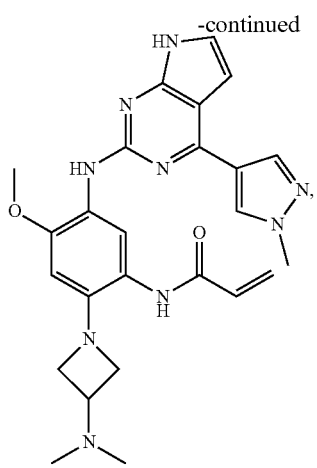
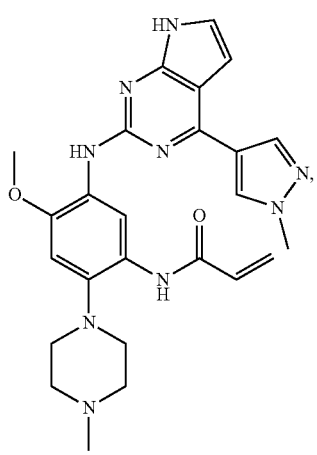
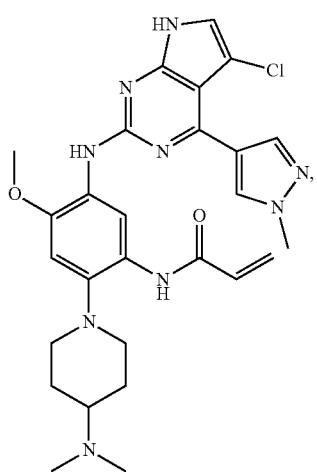
14
-continued
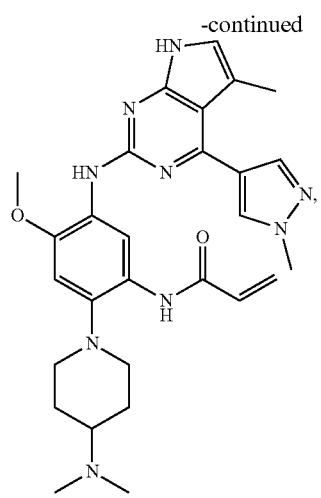
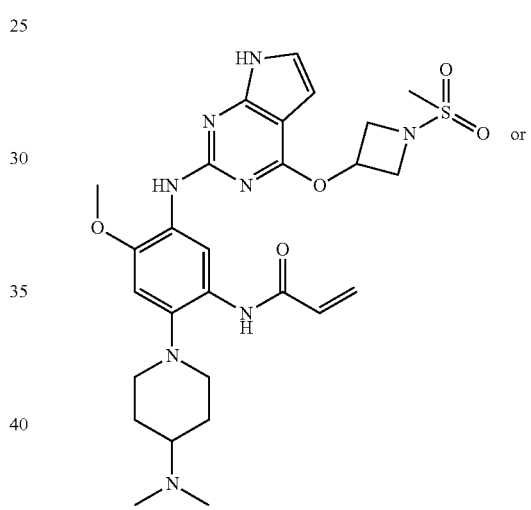
or
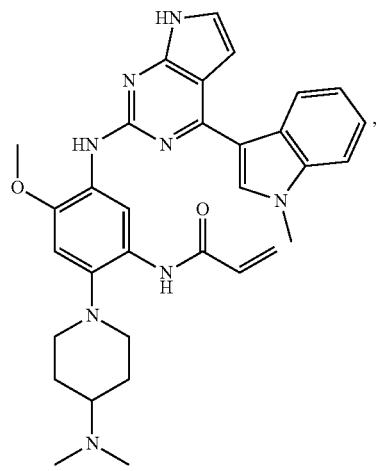

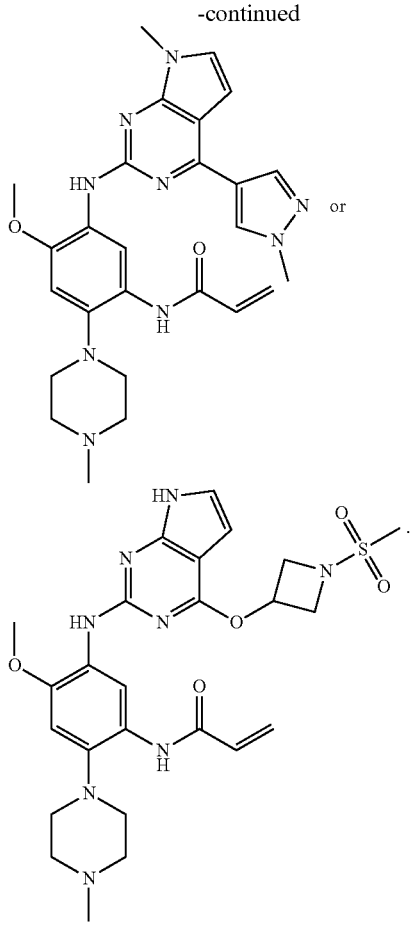

or

In the second aspect of the present invention, a pharmaceutical composition comprising the compound of the formula (I) in the first aspect of the present invention or the above exemplified compound, or a pharmaceutically acceptable salt, solvate, stereoisomer, or prodrug thereof, and a pharmaceutically acceptable carrier is provided.

In general, the compound of the present invention or a pharmaceutically acceptable salt, solvate, stereoisomer, or prodrug thereof can be administered in a suitable dosage form with one or more pharmaceutically acceptable carriers. These dosage forms are suitable for oral, rectal, topical, intra-oral and other parenteral administration (e.g., subcutaneous, muscle, intravenous, etc.). For example, dosage forms suitable for oral administration include capsules, tablets, granules, syrups and the like. The compounds of the present invention contained in these preparations may be solid powder or granules; solutions or suspensions in aqueous or nonaqueous liquids; water-in-oil or oil-in-water emulsions and the like. The above dosage forms may be made from the active compound with one or more carriers or excipients via a general pharmaceutical method. The above-mentioned carriers need to be compatible with the active compound or other excipients. For solid formulations, non-toxic carriers commonly used include, but are not limited to, mannitol, lactose, starch, magnesium stearate, cellulose, glucose, sucrose and the like. Carriers for liquid preparations include water, physiological saline, aqueous dextrose solution, ethylene glycol, polyethylene glycol and the like. The active compound may form a solution or suspension with the above carrier.

The compositions of the present invention are formulated, quantified and administered in a manner consistent with medical practice. The "effective amount" of the compound administered is dependent on the particular condition to be treated, the subject being treated, the cause of the disorder, the target of the drug, and the mode of administration.

In the third aspect of the present invention, use of said compound of the first aspect of the present invention, or a pharmaceutically acceptable salt, solvate, stereoisomer or prodrug thereof in (i) the manufacture of a medicament for the regulation of EGFR tyrosine kinase activity, or (ii) the manufacture of a medicament for preventing and/or treating EGFR-related diseases, is provided.

In another preferred embodiment, said regulation is up-regulation or down-regulation.

Preferably, said EGFR-related disease is cancer, diabetes, immune system disease, neurodegenerative disease, or cardiovascular disease, or a disease with acquired drug-resistance during treatment with an EGFR modulator.

Preferably, said cancer is non-small cell lung cancer, head and neck cancer, breast cancer, kidney cancer, pancreatic cancer, cervical cancer, esophageal cancer, pancreatic cancer, prostate cancer, bladder cancer, colorectal cancer, ovarian cancer, gastric cancer, brain malignancies including glioblastomas, etc., or any combination thereof.

Preferably, said acquired drug-resistance is caused by the T790 mutation encoded by EGFR exon 20 or contains drug resistance caused by the T790 mutation encoded by EGFR exon 20, such as T790M.

Preferably, said non-small cell lung cancer is caused by an EGFR mutation, including a sensitive mutation (such as L858R mutation or exon 19 deletion) and a drug-resistance mutation (such as EGFR T790M mutation).

In the present invention, EGFR modulators refer to small molecule tyrosine kinase inhibitors targeting EGFR, such as gefitinib, erlotinib, icotinib lapatinib, afatinib and the like.

In the fourth aspect of the present invention, it provides a medicinal composition comprising a therapeutically effective amount of said compound according to the first aspect of the invention, or a pharmaceutically acceptable salt, solvate, stereoisomer, prodrug thereof, and a medicament selected from the group consisting of: gefitinib, erlotinib, icotinib, lapatinib, XL647, NVP-AEE-788, ARRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitors, CNF2024, tanespimycin, alvespimycin, IPI-504, SNX-5422, NVP-AUY922, or a combination thereof. Except the compound of the present invention, or a pharmaceutically acceptable salt, solvate, stereoisomers, or prodrug thereof, other drugs in the above-mentioned medicinal composition are antitumor drugs well known to those skilled in the art.

The term "therapeutically effective amount" refers to an amount that is functional or active to humans and/or animals and can be accepted by humans and/or animals.

The therapeutically effective amount of the compound of the present invention or a pharmaceutically acceptable salt, solvate, stereoisomer or prodrug thereof contained in the pharmaceutical composition or the medicinal composition according to the present invention is preferably 0.1 mg to 5 g/kg (body weight).

Said medicinal composition can be used for treating EGFR-related diseases, such as cancer, diabetes, immune system diseases, neurodegenerative diseases, or cardiovascular diseases, or a disease with acquired drug-resistance during treatment with an EGFR modulator.

The acquired drug-resistance disease is a disease caused by the T790 mutation encoded by EGFR exon 20 or comprises a disease caused by the T790 mutation encoded by EGER exon 20.

In another preferred embodiment, the T790 mutation encoded by EGFR exon 20 is T790M.

The compound of formula (I) of the present invention, or a pharmaceutically acceptable salt, solvate, stereoisomer, or prodrug thereof may be used in combination with other drugs in certain diseases to achieve the desired therapeutic effect. An example of such combination is one that is used to treat advanced NSCLC. For example, a therapeutically effective amount of the compound of formula (I) of the present invention is used in combination with a mTOR inhibitor (e.g., rapamycin); or in combination with a Met inhibitor (including Met antibody MetMAb and Met small molecule inhibitor PF02341066); or in combination with an IGF1R inhibitor (e.g., OSI-906) or in combination with a heat shock protein inhibitor and so on.

In the fifth aspect of the present invention, a preparation method of the compound of formula (1) according to the first aspect, or a pharmaceutically acceptable salt, solvate, stereoisomer, or prodrug thereof is provided.

Said method comprises the following steps:

(i) subjecting the compound of formula I-f to a reduction reaction to form the compound of formula I-g;

(ii) subjecting the compound of formula I-g and acryloyl chloride to a condensation reaction to form the compound represented by formula (I);

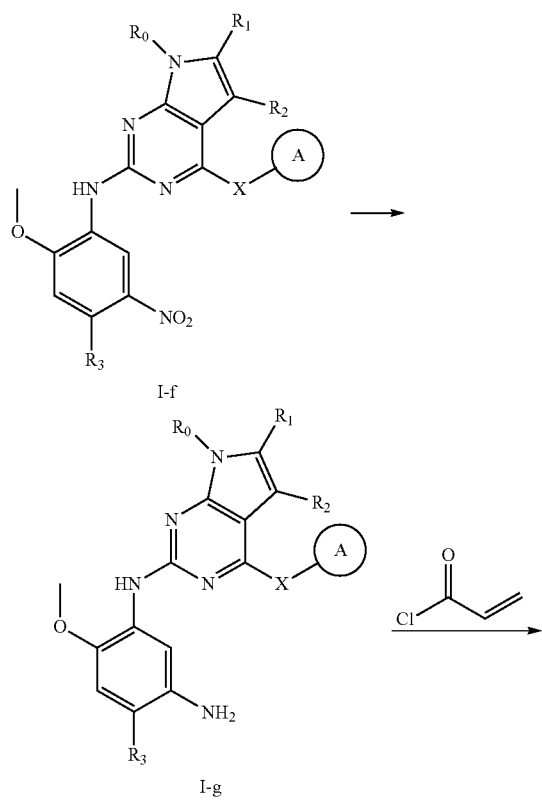

or said method comprises step (i'): allowing the compound of formula I-c to react with the compound of formula I-h in an inert solvent to form the compound represented by formula (I);

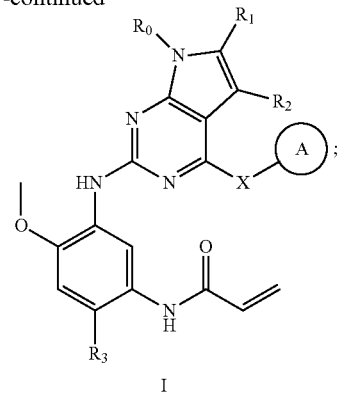

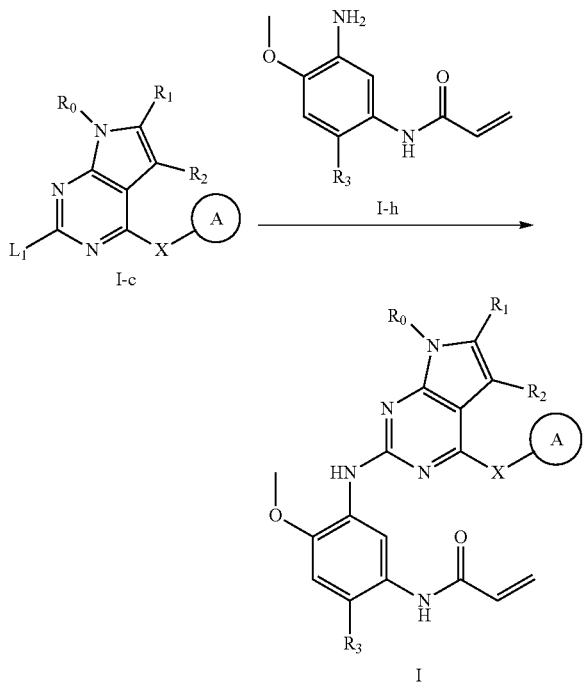

wherein, $R_0$, $R_1$, $R_2$, $R_3$, X, and A ring are defined as above; $L_1$ is a leaving group.

In another preferred embodiment, said $L_1$ includes trifluoromethanesulfonate: chlorine, bromine, iodine; sulfonate group (e.g., mesylate, tosylate, p-bromobenzenesulfonate, p-toluenesulfonate, etc.); acyloxy (e.g., acetoxy, trifluoroacetoxy, etc.)

In another preferred embodiment, in said step (i), said reaction is conducted in an acidic condition.

In another preferred embodiment, in said step (i), metal (such as iron powder, zinc powder) or stannous chloride is used for the reduction.

In another preferred embodiment, in said step (i), the reduction reaction is conducted by adding hydrogen in the presence of a palladium-carbon catalyst.

In another preferred embodiment, said step (ii) is conducted in an alkaline condition.

In another preferred embodiment, in said step (ii), the compound of formula I-g and a carboxylic acid are subjected to a condensation reaction in the presence of a condensation agent to form the compound of formula (I).

In another preferred embodiment, said step (i') is conducted in the presence of a catalyst, ligand or base.

In another preferred embodiment, in said step (i'), said catalyst is selected from the group consisting of: TFA, p-toluenesulfonic acid, $Pd_2(dba)_3$ tris(dibenzylideneacetone)dipalladium), BINAP((±)-2,2'-bis-(diphenylphosphino)-1,1'-dinaphthalene), or a combination thereof;

said ligand includes: Xantphos(4,5-bis(diphenylphosphino)-9,9-dimethylxanthene); and/or said base includes: cesium carbonate.

It is to be understood that within the scope of the present invention, each foregoing technical feature of the present invention and each technical feature described in detail below (e.g., examples) may be combined with each other to form a new or preferred technical solution.

DETAILED DESCRIPTION OF THE INVENTION

Based on a long-term and in-depth study, the inventors have unexpectedly found a class of selective inhibitors of the EGFR mutation. These selective inhibitors can inhibit the proliferation of cell line H1975 and EGFR. T790M/L858R double mutant enzyme at a nanomolar concentration, and also a have strong inhibitory effect on the EGFR-sensitive mutant cell line HCC827 (exon 19 deletion) while having relatively weak inhibition against wild-type EGFR enzyme and the cell line A431, as demonstrated by the in vitro experiments. Therefore, this kind of structure can be used not only in the treatment of cancers having an EGFR-sensitive mutant, but also in the treatment of the cases with secondary drug-resistance in the current EGFR-TKI treatment. Meanwhile, its mutation selectivity greatly reduces the toxic side effects caused by the inhibition of wild-type EGFR. Furthermore, this kind of compounds has low cytotoxicity in normal cell lines (such as NIH-3T3 cells), thus greatly reducing the non-specific toxic side effect, which makes them ideal replacements for the second-generation EGFR-TKI.

Definition of Terms

"$C_{3-10}$ heterocyclic radical" refers to a heterocyclic radical having 3-10 carbon atoms, wherein the atoms constituting the ring contain at least one heteroatom selected from N, S, and O besides the carbon atoms. The examples include pyrazolyl, morpholinyl, aza-$C_{3-7}$ cycloalkyl, pyrrolopyridyl, pyrazolopyridyl, indazolyl, pyrrolyl, indolyl, or pyridyl.

"$C_{1-3}$ alkyl" refers to a straight or branched saturated aliphatic hydrocarbyl having 1 to 3 carbon atoms, such as methyl, ethyl, propyl, isopropyl.

"$C_{3-6}$ cycloalkyl" refers to a cycloalkyl having 3 to 6 carbon atoms. Examples of cycloalkyl are cyclopropyl, cyclobutyl, cyclopentyl, cyclohexyl and the like.

"aza-$C_{3-7}$ cycloalkyl" refers to a cycloalkyl having 3 to 7 carbon atoms wherein the atoms constituting the ring contain at least one nitrogen atom besides the carbon atoms.

"$C_{6-10}$ aryl" and "$C_{6-10}$ aryl ring" can be used interchangeably and mean an aromatic hydrocarbyl having 6 to 10 carbon atoms such as phenyl, naphthyl and the like.

"halogen" refers to fluoro, chloro, bromo or iodo.

"heteroaryl ring" and "heteroaryl" can be used interchangeably and refer to a group having 5 to 10 ring atoms, preferably 5, 6, 9 or 10 ring atoms, and having 1 to 5 heteroatoms besides the carbon atoms, wherein the ring array shares 6, 10 or 14 π electrons. The term "heteroatom" refers to N, O or S.

As used herein, "partially unsaturated" refers to a π electron system which contains one or more unsaturated bonds, but is not fully conjugated.

"5 to 6 membered monocyclic heteroaryl ring containing 1 to 2 nitrogen atoms" means a monocyclic heteroaryl group having 5 to 6 ring atoms, e.g., including, but not limited to, imidazole ring, pyrrole ring, pyrazole ring, pyridine ring, pyridazine ring, pyrimidine ring, and pyrazine ring.

"9 to 10 membered bicyclic heteroatyl ring containing 1, 2 or 3 nitrogen atoms" means a bicyclic heteroaryl group having 9 to 10 ring atoms, e.g., including, but not limited to, indole ring, isoindole ring, quinoline ring, isoquinoline ring, indazole ring, benzimidazole ring, quinazoline ring, quinoxaline ring, cinnoline ring, phthalazine ring.

In the present invention, said 5 to 6 membered monocyclic heteroaryl ring or 9 to 10 membered bicyclic heteroaryl ring is preferably selected from the group consisting of:

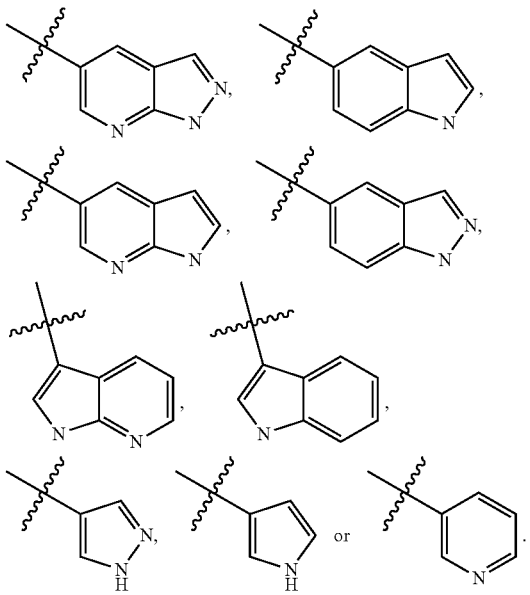

"4 to 7 membered saturated monocyclic heterocyclic ring containing one nitrogen atom" means a saturated monocyclic ring containing 4 to 7 ring atoms and one carbon atom replaced by a nitrogen atom. Examples of the monocyclic heterocyclic ring include, but are not limited to, piperidine ring, tetrahydropyrrole ring, azetidine, azepane.

"6 membered partially unsaturated monocyclic ring" refers to a partially unsaturated, all-carbon monocyclic ring containing 6 ring atoms. Examples include, but are not limited to, 1,3-cyclohexadiene, 1,4-cyclohexadiene, cyclohexene and the like.

Pharmaceutical Compositions

The phrase "the active substance of the present invention" or "the active compound of the present invention" refers to the compound of formula (I) of the present invention, or a pharmaceutically acceptable salt, solvate, stereoisomer, or prodrug thereof, which has significant EGFR T790M/L858R selective inhibitory activity.

As used herein, said "pharmaceutically acceptable salt" includes a pharmaceutically acceptable acid addition salt and a pharmaceutically acceptable base addition salt.

"Pharmaceutically acceptable acid addition salt" refers to a salt formed with an inorganic acid or an organic acid that is capable of retaining the bioavailability of the free base without any other side effects. Inorganic acid salt includes, but is not limited to, hydrochloride, hydrobromide, sulfate, phosphate and the like; and organic acid salt includes, but is not limited to formate, acetate, propionate, glycolate, gluconate, lactate, oxalate, maleate, succinate, fumarate, tartrate, citrate, glutamate, aspartate, benzoate, methanesulfonate, p-toluenesulfonate, salicylate and the like. These salts can be prepared by the methods known in the art.

"Pharmaceutically acceptable base addition salt" includes, but is not limited to, salt of an inorganic base such as sodium, potassium, calcium and magnesium salts and the like, and includes, but is not limited to, salt of an organic base such as ammonium salt, triethylamine salt, lysine salt, arginine salt and the like. These salts can be prepared by the methods known in the art.

As used herein, the compounds of formula (I) may be present in one or more crystalline forms, and the active compounds of the present invention include various crystalline forms and mixtures thereof.

"Solvate" as used in the present invention refers to a complex formed by the compound of the present invention with a solvent. They either react in a solvent or precipitate or crystallize out of the solvent. For example, a complex formed with water is called a "hydrate". Solvates of the compounds of formula (I) are within the scope of this invention.

The compounds represented by formula (I) of the present invention may contain one or more chiral centers and exist in different optically active forms. When the compound contains one chiral center, the compound comprises an enantiomer. The present invention includes both isomers and mixtures thereof, such as racemic mixtures. Enantiomers can be resolved by methods known in the art, such as crystallization, chiral chromatography and the like. When the compound of formula (I) contains more than one chiral center, diastereomers may be present. The present invention includes specific optically pure isomers which have been resolved, as well as mixtures of diastereomers. Diastereomers can be resolved by methods known in the art, such as crystallization and preparative chromatography.

The present invention includes prodrugs of the above-mentioned compounds. Prodrugs include known amino-protecting group and carboxy-protecting group, which are released to yield the parent compound via hydrolyzation or enzymatic reactions under physiological conditions. For specific preparation methods of prodrug, one can refer to Saulnier, M. G.; Frennesson, D. B.; Deshpande, M. S.; Hansel, S. B. and Vysa, D. M. Bioorg. Med. Chem Lett. 1994, 4, 1985-1990; and Greenwald, R. B.; Choe, Y. H.; Conover, C. D.; Shum, K.; Wu, D.; Royzen, M. J. Med. Chem. 2000, 43, 475.

Preparation Methods

The present invention provides a method for the preparation Of compounds of formula (I) wherein the compounds of the present invention can be readily prepared by a variety of synthetic manipulations which are well-known to the skilled in the art. Exemplary preparative methods for these compounds may include, but are not limited to, the processes described below.

In general, in the preparation method of the present invention, each of the reactions is carried out in an inert solvent at −20° C. to 150° C. (or reflux temperature) (preferably from −5° C. to 100° C. or from 0 to 80° C.) for a period of time (e.g. 0.1-72 hours, preferably 0.5-24 hours).

Preferably, the compounds of formula (I) of the present invention can be prepared by the exemplary methods described in the following schemes and examples, as well as the related publications used by those skilled in the art.

During the course of the operation, the steps in the method can be expanded or combined as needed.

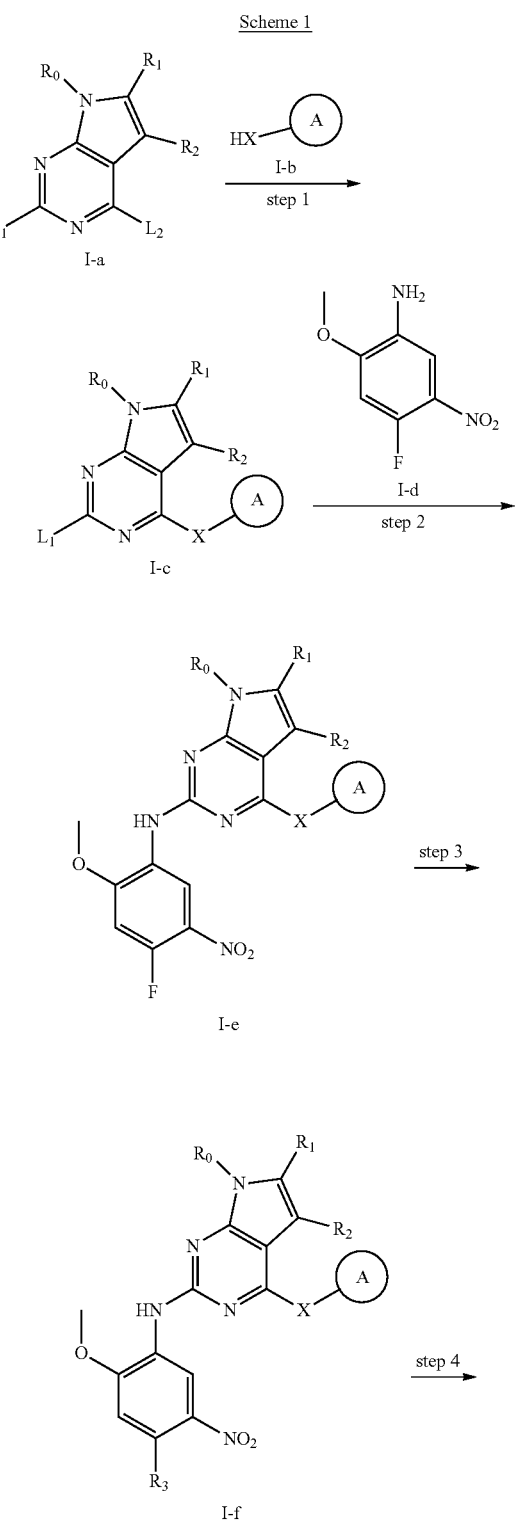

Scheme 1

-continued

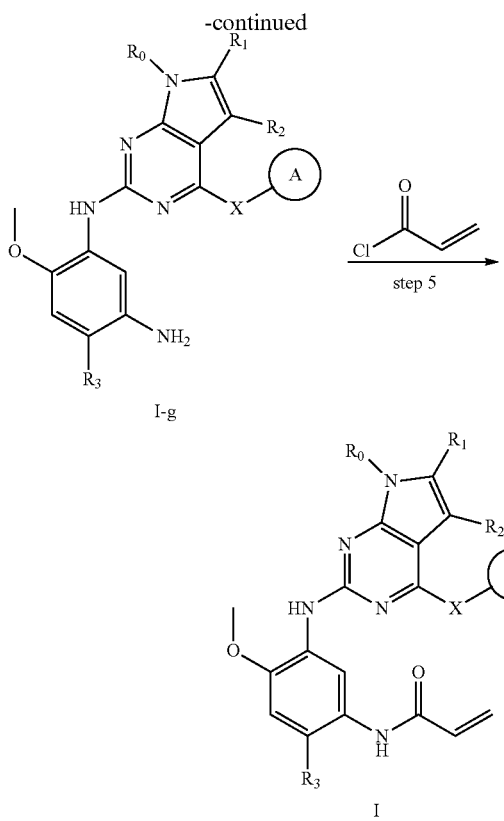

In Scheme 1, each substituent and group are defined as in the specification.

In step 1, when X is N, O, or S, formula (I-a) compound and formula (I-b) compound can generate formula (I-c) compound through a substitution reaction (e.g., nucleophilic substitution reaction or the like);

when X is a covalent bond, formula (I-b) compound is a boronic acid or borate compound of the respective ring A, formula (I-a) compound and formula (I-b) compound can generate formula (I-c) compound through a coupling reaction (e.g.; Suzuki coupling, etc.);

$L_1$ and $L_2$ in formula (I-a) compound are leaving groups which include, but are not limited to, trifluoromethanesulfonate; chlorine, bromine, iodine; sulfonate groups such as methanesulfonate, tosylate, p-bromobenzenesulfonate, p-toluenesulfonate and the like; acyloxy such as acetoxy, trifluoroacetoxy and the like.

In step 2, the compound of formula (I-c) may react with the compound of formula (I-d) via a substitution or coupling reaction to form the compound of formula (I-e), for example, using a suitable catalyst (or with suitable ligands) or alkali and a suitable solvent at a certain temperature. If acid catalysis is used, the catalyst may be, but is not limited to, TFA or p-toluenesulfonic acid. When Buchwald-Hartwig amination is used, the palladium catalyst used may be, but is not limited to $Pd_2(dba)_3$, the ligand used may be, but is not limited to, XantPhos (4,5-bis(diphenylphosphino)-9,9-dimethylxanthene), and the base used may be, but is not limited to, cesium carbonate.

In step 3, the compound of formula (I-e) may be subjected to an amine substitution reaction with various amine compounds to fora the compound of formula (I-f), wherein the synthesis can be conveniently carried out by selecting suitable conditions and methods depending on the particular amine compound. For example the synthesis can be carried out at a certain temperature by using a suitable catalyst (or with a suitable ligand) or base and a suitable solvent. The method is a conventional method used by those skilled in the art.

In step 4, conversion of the nitro compound I-f to the corresponding amine compound can be carried out through reduction by using a metal (which may be, but not limited to, iron powder, zinc powder) or stannous chloride under an acidic condition; or through reduction by hydrogenation under palladium-on-carbon catalyse.

In step 5, the amino compound I-g can condense with the corresponding acyl chloride to form an amide under a basic condition, or condense with the corresponding carboxylic acid to form an amide in the presence of a condensing agent.

In scheme 1, the compounds of formula (I-a) and formula (I-b) are commercially available or can be prepared by methods well known in the art.

Scheme 2

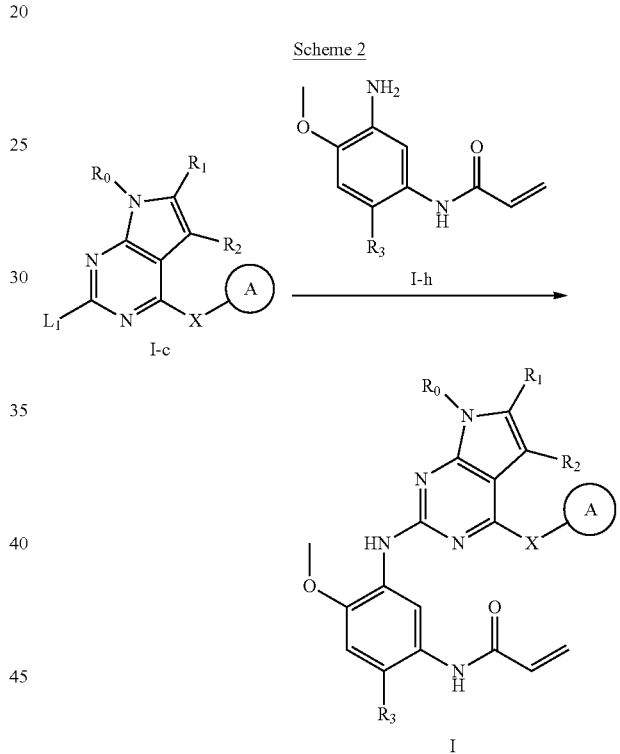

In scheme 2, each substituent and group are defined as in the specification.

The compound of formula (I-c) can react with the compound of formula (I-h) by a substitution or coupling reaction to form the compound of formula (I), for example at a certain temperature, using a suitable catalyst (or with suitable ligands) or base and an appropriate solvent. If acid catalysis is used, the catalyst may be, but is not limited to, TFA or p-toluenesulfonic acid. When Buchwald-Hartwig amination is used, the palladium catalyst used may be, but is not limited to, $Pd_2(dba)_3$ (tris(dibenzylideneacetone)dipalladium), BINAP ((±)-2,2'-bis-(diphenylphosphino)-1,1'-binaphthalene). The ligand used may be, but is not limited to, Xantphos (4,5-bis(diphenylphosphino)-9,9-dimethyloxanthene), and the base used may be, but is not limited to, cesium carbonate.

In scheme 2, the compound of formula (I-h) can be prepared by the following exemplary method:

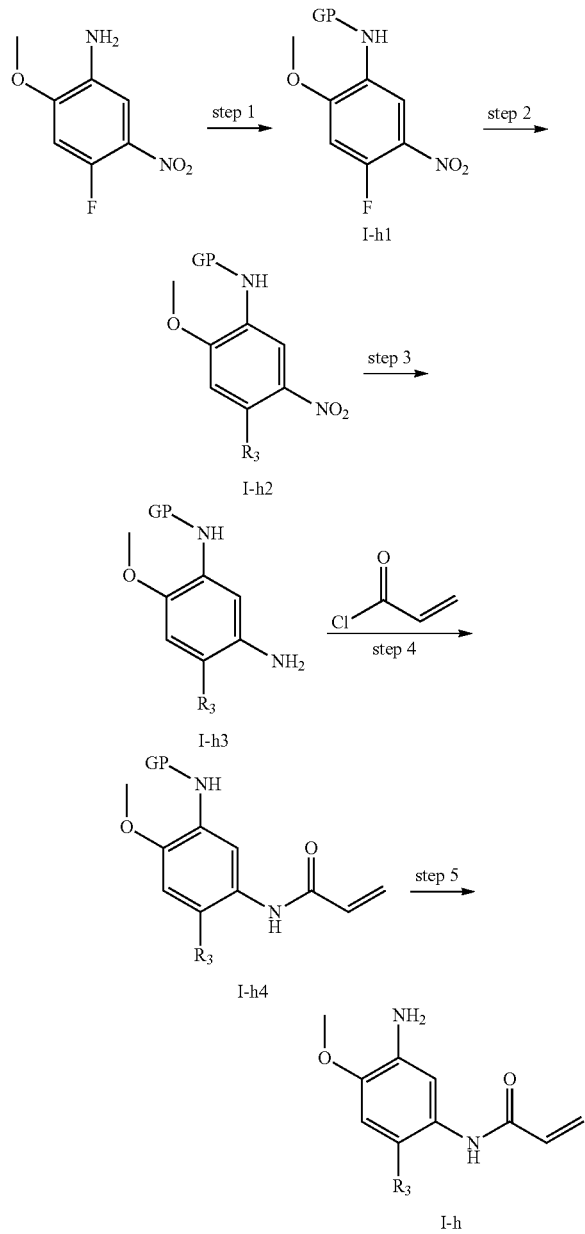

The compound of formula (I-h) is prepared from the starting material, 4-fluoro-2-methoxy-5-nitroaniline, via amino protection reaction, amine substitution reaction, nitro reduction reaction, acylation reaction and amino deprotection reaction in a sequential order. Each of the above-described reactions is conventional in the art. 4-fluoro-2-methoxy-5-nitroaniline is commercially available or can be prepared by methods known to those skilled in the art. The preparation method of the compound of formula (I-h) can be referred to WO2013014448A1.

PG in the compound of the formula (I-h1) is an amino-protecting group. The amino-protecting group includes, but is not limited to, tert-butoxy carbonyl (Boc); aryl methoxycarbonyl, benzyloxycarbonyl (Cbz) and 9-fluorenylmethyloxycarbonyl (Fmoc); benzyl (Bn), triphenylmethyl (Tr), 1,1-bis-(4'-methoxyphenyl)methyl; trimethylsilyl (TMS) and t-butyldimethylsilyl (TBS) and the like. The protection and deprotection methods can be referred to conventional methods well known in the art.

The compounds of formula (I), the preparation methods thereof, the pharmaceutical composition, and the therapeutic regimens disclosed in the present invention can be achieved by the skilled in the art with reference to the contents of the present invention and with appropriate modification of the process parameters. It is to be noted that all similar alternatives and modifications will be apparent to those skilled in the art and are considered to be included in the present invention. The products, methods and applications of the present invention have been described by way of preferred embodiments and examples, and it will be apparent to those skilled in the art that changes and combinations of the methods and applications described herein may be made to realize and apply the technology of the present invention while not departing from the contents, spirit and scope of the present invention.

Compared with the prior art, the main advantages of the present invention are:

(1) the compounds of the present invention have high inhibitory activity against EGFR. T790M mutant type (particularly EGFR T790M/L858R double mutant type) enzymes and cells, and have low inhibitory activity against EGFR wild type (EGFR WT) enzyme and cells, therefore the compounds have highly selective inhibition.

(2) while the compounds of the present invention exhibit highly selective inhibition to EGFR double mutant enzymes and cells, they also show low non-specific cytotoxicity.

(3) the compounds of the present invention also exhibit advantageous physical properties (e.g., higher water solubility), favorable toxicity characteristics (e.g., lower tendency to hERG blockage) and favorable metabolic characteristics (e.g., better pharmacokinetic characteristics, such as bioavailability) compared to other known EGFR mutation inhibitors.

The present invention will be further elucidated with reference to specific examples. It is to be understood that these examples are merely illustrative of the present invention and are not intended to limit the scope of the present invention. The experimental methods which do not specify specific conditions in the following examples are generally carried out according to conventional conditions such as those described in Sambrook et al., Molecular Cloning: Laboratory Manual (New York: Cold Spring Harbor Laboratory Press, 1989), or conditions as recommended by the manufacturers. Unless otherwise indicated, percentages and parts are by weight.

Unless otherwise defined, terms used herein are of the same meanings that are familiar to those skilled in the art. In addition, any methods and materials similar with or equivalent to those described herein can be applied to the present invention.

Reagents and Instruments

$^1$HNMR: Bruker AVANCE-400 NMR instrument, internal standard is tetramethylsilane (TMS).

LC-MS: Agilent 1200 HPLC System/6140 MS spectrometer (manufacturer: Agilent), WatersX-Bridge column, 150× 4.6 mm, 3.5 μm.

Preparative high performance liquid chromatography (pre-HPLC): Waters PHW007, XBridge C18 column, 4.6*150 mm, 3.5 um.

ISCO Combiflash-Rf75 or Rf200 automatic column instrument as well as Agela 4 g, 12 g, 20 g, 40 g, 80 g, and 120 g disposable silica gel column were used.

Known starting materials may be synthesized using methods known in the art, or can be purchased from ABCR GmbH & Co. KG, Acros Organics, Aldrich Chemical Company, Accela ChemBio Inc, Darryl Chemicals and so on.

Unless otherwise specified, the reactions in the examples were carried out in a nitrogen or argon atmosphere.

Unless otherwise stated, the solutions in the examples were aqueous solutions.

In the examples, the progress of the reaction can be monitored by thin layer chromatography (TLC), and the purification of the compounds can be carried out by column chromatography. The developing solvent system used for column chromatography or TLC can be selected from the group consisting of dichloromethane and methanol, n-hexane and ethyl acetate, petroleum ether and ethyl acetate, and acetone system, and the volume ratio of solvents is adjusted according to the polarity of the compound.

DMF: dimethylformamide, DMSO: dimethylsulfoxide, THF: tetrahydrofuran, DIEA: N,N-diisopropylethylamine, EA: ethyl acetate, PE: petroleum ether, BINAP: (2R,3S)-2,2'-bis-diphenylphosphino-1,1'-binaphthalene. NBS (N-bromosuccinimide), NCS (N-chlorosuccinimide), $Pd_2(dba)_3$ (tris (dibenzylideneacetene) dipalladium). $Pd(dppf)Cl_2$ ([1,1'-bis (diphenylphosphino) ferrocene]dichloropalladium).

As used herein, room temperature refers to about 20-30° C.

Preparation of Compound a1

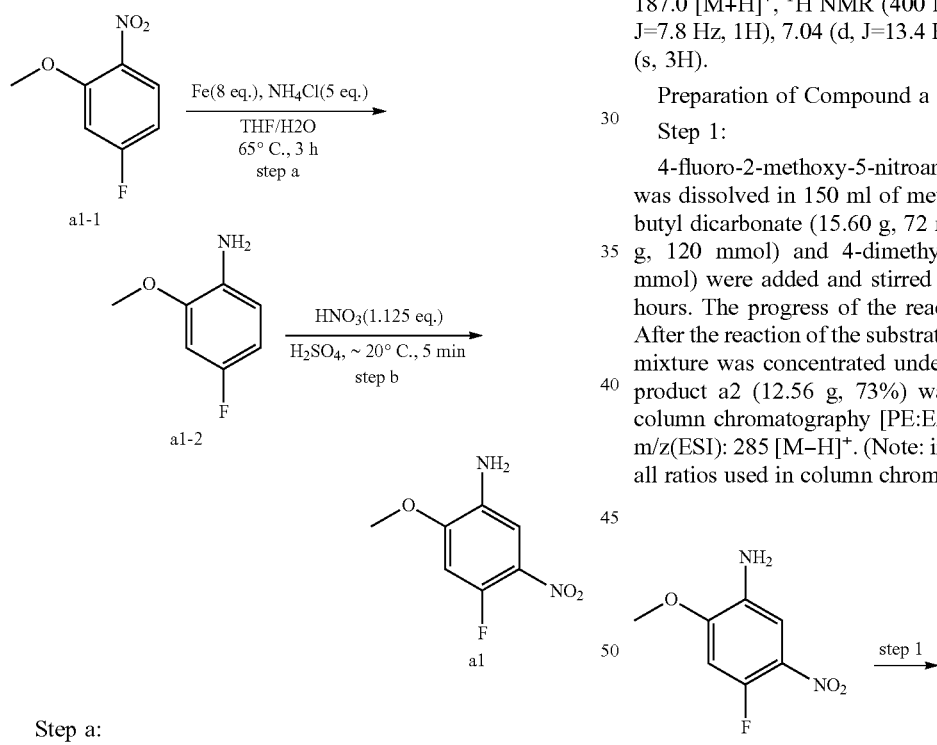

Step a:

The reaction substrate a1-1 (10.6 g, 58 mmol) was placed in a 500 mL single-necked reaction flask and a mixed solution of tetrahydrofuran/water (100 mL/60 mL) was added to dissolve the substrate. Ammonium chloride (15.5 g, 292 mmol) and reduced iron powder (26 g, 467 mmol) were added sequentially to the reaction flask under stirring at room temperature, after which the reaction was heated to 65° C. and stirred continuously for 3 hours. The progress of the reaction was monitored by TLC. After the reaction of the substrate was complete, the excess iron powder was removed by filtration and the filter cake was rinsed three times with ethyl acetate. The filtrate was extracted three times with ethyl acetate/water system, and the organic layer was separated, washed with water and then saturated brine, dried over anhydrous sodium sulfate and concentrated under reduced pressure to give compound a1-2 (8.0 g), which was directly used in the next step. Yield: 93%; purity: 90%; MS m/z(ESI): 142.0 $[M+H]^+$.

Step b:

Compound a1-2 (8.0 g, 43 mmol) was placed in a 500 mL single-necked reaction flask and concentrated sulfuric acid (100 mL) was added under stirring at a constant rate to dissolve the substrate. Concentrated nitric acid (6.15 mL, 48 mmol) was slowly added dropwise to the stirred reaction flask at −20° C. and stirred at that temperature for 5 minutes. The progress of the reaction was checked by TLC. After the reaction of the substrate was complete, the reaction mixture was poured into iced water. In −20° C. ice bath, the aqueous solution of hydroxide/water (150 mL/300 mL) was slowly added to the reaction system and pH was adjusted to 8-9. After neutralization, the reaction solution was extracted three times with ethyl acetate/water system. The organic layer was separated, washed with water and then saturated brine, dried over anhydrous sodium sulfate and concentrated under reduced pressure to give the compound 4-fluoro-2-methoxy-5-nitroaniline a1 (8.7 g) which was directly used in the next step. Yield: 80%, purity: 100%; MS m/z(ESI): 187.0 $[M+H]^+$, $^1H$ NMR (400 MHz, DMSO-$d_6$): δ 7.34 (d, J=7.8 Hz, 1H), 7.04 (d, J=13.4 Hz, 1H), 5.25 (brs, 2H), 3.90 (s, 3H).

Preparation of Compound a

Step 1:

4-fluoro-2-methoxy-5-nitroaniline a1 (11.16 g, mmol) was dissolved in 150 ml of methylene chloride and di-tert-butyl dicarbonate (15.60 g, 72 mmol), triethylamine (12.24 g, 120 mmol) and 4-dimethylaminopyridine (0.74 g, 6 mmol) were added and stirred at room temperature for 18 hours. The progress of the reaction was checked by TLC. After the reaction of the substrate was complete, the reaction mixture was concentrated under reduced pressure, and the product a2 (12.56 g, 73%) was isolated and purified by column chromatography [PE:EA volume ratio=80:20]. MS m/z(ESI): 285 $[M-H]^+$. (Note: in the following experiments, all ratios used in column chromatography are volume ratio)

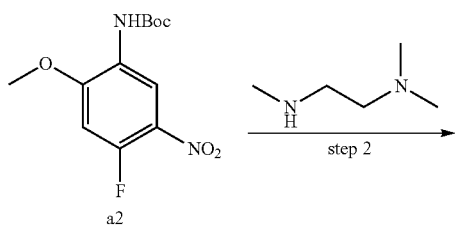

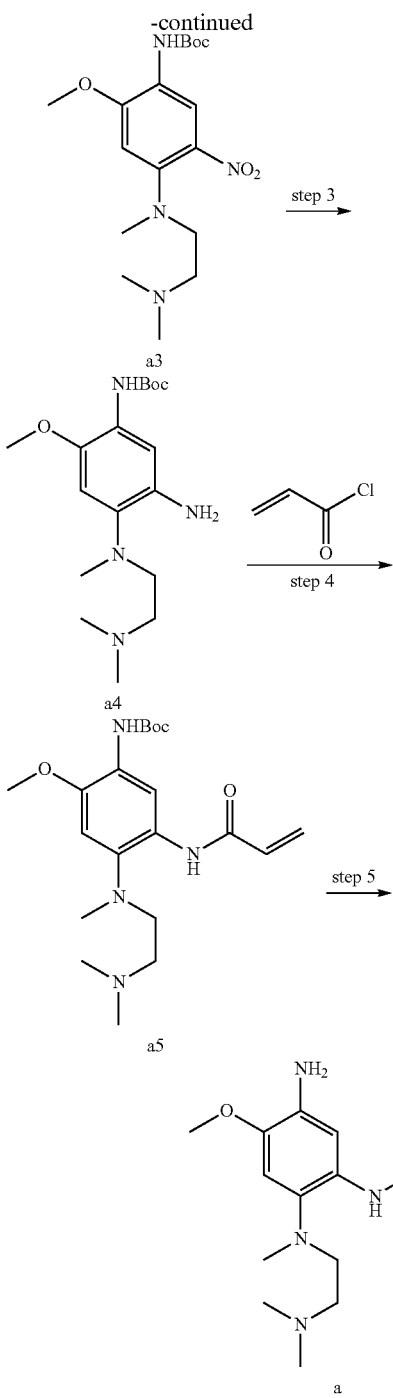

sure to give the target product a3 (12.51 g, 85%) which was directly used in the next step. MS m/z (ESI): 369 [M+H]⁺.

Step 3:

Tert-butyl 4-((2-(dimethylamino)ethyl)(methyl)amino)-2-methoxy-5-nitrophenylcarbamate a3 (12 g, 32.6 mmol) was dissolved in 200 ml of methanol and 1 g of 10% Pd/C was added. After the air was replaced with hydrogen, hydrogenation was carried out at room temperature with a hydrogen balloon, and the reaction was stirred for 1 hour. The progress of the reaction was monitored by TLC. After the reaction a the substrate was complete, the reaction mixture was filtered in vacuum through a sand-core funnel. The filter cake was washed with a small amount of methanol and the filtrate was concentrated to give the desired product a4 (10.70 g, 97%) which was directly used in the next step. MS m/z (ESI) 339 [M+H]⁺.

Step 4:

Tert-butyl 5-amino-4-((2-(dimethylamino)ethyl)(methyl)amino)-2-methoxyphenyl carbamate a4 (10.1 g, 30 mmol) and triethylamine (6.12 g, 60 mmol) were dissolved in 200 ml of methylene chloride and cooled to 0° C. Actyloyl chloride (3.24 g, 36 mmol) was added and stirred at room temperature under nitrogen for 3 hours. The reaction progress was monitored by TLC. After the reaction of the substrate was complete, the reaction mixture was washed successively with saturated aqueous solution of sodium hydrogencarbonate and saturated brine, dried over anhydrous sodium sulfate, filtered via suction and concentrated under reduced pressure to give the target product a5 (9.64 g, 82%) which was directly used in the next reaction. MS m/z(ESI):393 [M+H]⁺.

Step 5:

Tert-butyl 5-acrylamido-4-((2-(dimethylamino)ethyl)(methyl)amino)-2-methoxyphenyl carbamate a5 (9.4 g, 24 mmol) was dissolved in 100 ml of dichloromethane, cooled to 0° C., 20 ml of trifluoroacetic acid was added and the mixture was stirred at room temperature under nitrogen for 18 hours. The progress of the reaction was checked by TLC. After the reaction of the substrate was complete, the reaction solution was concentrated under reduced pressure. The residue was dissolved in 300 ml of methylene chloride, washed successively with saturated aqueous sodium bicarbonate solution and saturated brine, dried over anhydrous sodium sulfate, suction filtered and concentrated under reduced pressure to obtain a crude product which was purified by column chromatography [DCM:MeOH volume ratio=10:1] to afford the desired product N-(5-amino-2-(2-(dimethylamino)ethyl)(methyl)methoxyphenyl) acrylamide a (3.26 g, 46.5%). MS m/z(ESI): 293 [M+H]⁺.

Preparation of Compound b

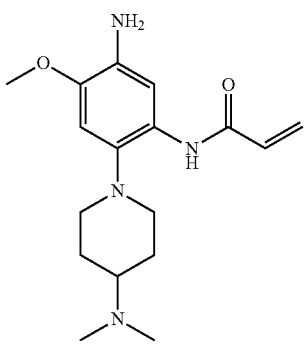

Step 2:

The reaction substrate tert-butyl 4-fluoro-2-methoxy-5-nitrophenylcarbamate a2 (11.46 g, 40 mmol) was dissolved in 60 ml of N,N-dimethylacetamide, and N,N,N'-trimethylethylenediamine (4.90 g, 48 mmol) and N,N-diisopropylethylamine (7.74 g, 60 mmol) were added. The mixture was heated to 90° C. and stirred for 6 hours. The progress of the reaction was checked by TLC. After the reaction of the substrate was complete, the reaction mixture was cooled to room temperature, poured into iced water, extracted with ethyl acetate, washed with saturated brine, dried over anhydrous sodium sulfate and concentrated under reduced pres- The preparation method was identical with that of compound a, except that N,N,N'-trimethylethylenediamine in Step 2 of the preparation method of compound a was replaced by 4-dimethylaminopiperidine.

Preparation of Compound c

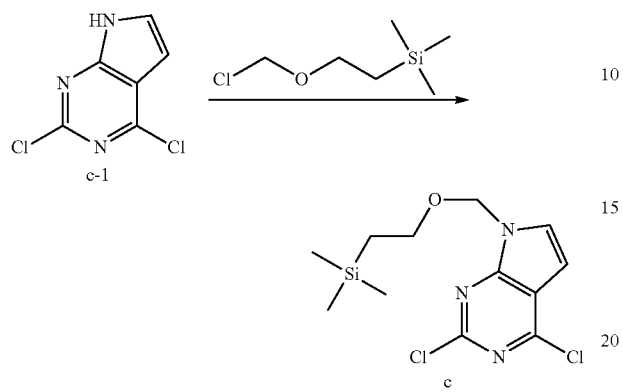

At 0° C., sodium hydride (420 mg, 10.64 mmol) was added to the solution of 2,4-dichloro-7H-pyrrolo[2,3-d]pyrimidine c-1 (1 g, 5.32 mmol) in DMF (40 ml) and the reaction mixture was stirred for 30 minutes. 2-(trimethylsilyl)ethoxymethyl chloride (1.34 g, 7.98 mmol) was then added. The reaction mixture was stirred at 0° C. for 3 hours. At the end of the reaction, the reaction was quenched with water at 0° C. The mixture was extracted with ethyl acetate and water, and the organic phase was washed with water and saturated sodium chloride solution and concentrated under reduced pressure to give 2 g of 2,4-dichloro-7-(2-(trimethylsilyl)ethoxy)methyl)-7H-pyrrolo[2,3-d]pyrimidine c as an oil which was directly used without purification in the next step. MS m/z(ESI): 318 [M+H]+.

Preparation of Compound d

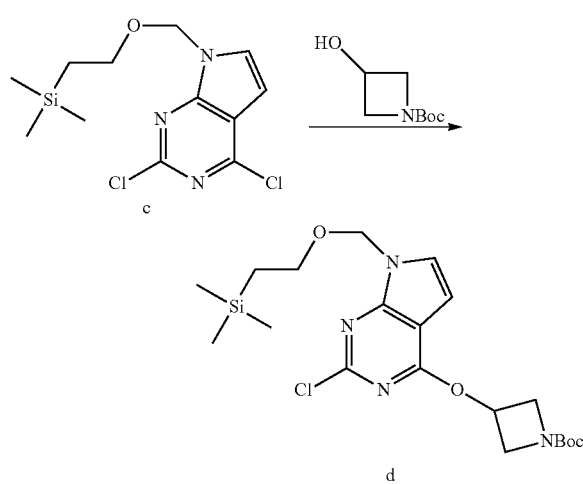

Compound c (1.6 g, 4.57 mmol), tert-butyl 3-hydroxyazetidine-1-carboxylate (881 mg, 5.09 mmol) and cesium carbonate (3 g, 9.21 mmol) were added to 30 ml of acetonitrile and the reaction mixture was stirred at 80° C. under an argon atmosphere for 5 hours. The reaction was followed by TLC plates and LC-MS. After the reaction was completed, the reaction solution was filtered, washed with methylene chloride, and the filtrate was concentrated to obtain a crude product which was purified by combiflash (PE:EA volume ratio=100:0-80:20) to give compound tert-butyl 3-(2-chloro-7-((2-(trimethylsilyl)ethoxy)methyl)-7H-pyrrolo[2,3-d]pyrimidin-4-yloxy)azetidine-1-carboxylate d (1.76 g, yield 84.53%). MS m/z(ESI):455.1 [M+H]+.

Preparation of Compound e

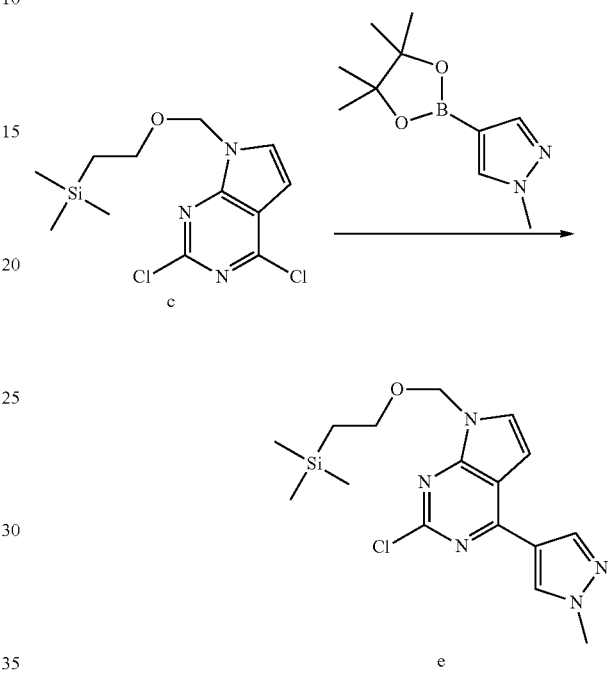

1-methyl-4-(4,4,5,5-tetramethyl-1,3,2-diaxaborolan-2-yl)-1H-pyrazole (66 mg, 0.31 mmol), Pd(dppf)Cl$_2$ (23 mg, 0.031 mmol) and sodium carbonate (66 mg, 0.62 mmol) were added to the solution of compound c (100 mg, 0.31 mmol) in acetonitrile/water (5/1 ml) under stirring. The reaction mixture was purged with argon three times and stirred at 80° C. for 4 hours. After the reaction of the substrate was complete, the reaction mixture was quenched with water. After ethyl acetate (150 mL) was added to the reaction mixture to separate, the aqueous phase was extracted twice with ethyl acetate (50 mL×2). The combined organic phase was dried over Na$_2$SO$_4$ and concentrated to obtain the crude product which was isolated and purified by Combi-flash column chromatography to give the desired product 2-chloro-4-(1-methyl-1H-pyrazol-4-yl)-7-((2-(trimethylsilyl)ethoxy)methyl)-7H-pyrrolo[2,3-d]pyrimidine e (100 mg, yield 70%). MS m/z(ESI): 364 [M+H]+.

Preparation of Compound f

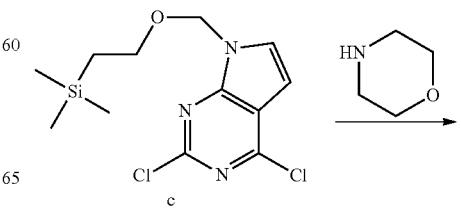

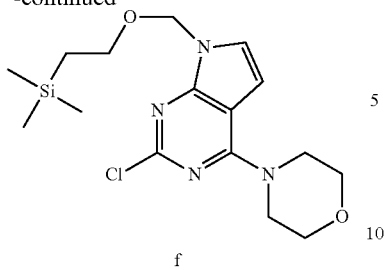

f

Morpholine (25 mg, 0.26 mmol) and triethylamine (41 mg, 0.4 mmol) were added to the solution of compound c (100 mg, 0.31 mmol) in THF (3 ml) under stirring and the reaction mixture was stirred at room temperature overnight. After the reaction was completed, water was added and the mixture was extracted with ethyl acetate. The organic phase was dried over anhydrous Na$_2$SO$_4$ and concentrated under reduced pressure to give 2-chloro-4-morpholino-7-((2-(trimethylsilyl)ethoxy)methyl)-7H-pyrrolo[2,3-d]pyrimidine f (100 mg, 70%) which was directly used in the next step without purification. MS m/z(ESI): 369 [M+H]$^+$.

Preparation of Compound g

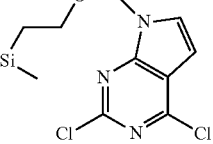

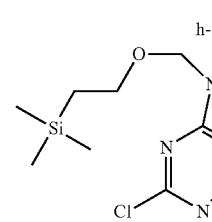

g 1-methyl-5-(4,4,5,5-tetramethyl-1,3,2-dioxaborolan-2-yl)-1H-pyrrolo[2,3-b]pyridine (370 mg, 1.43 mmol), Pd(dppf)Cl$_2$ (106 mg, 0.14 mmol) and sodium carbonate (304 mg, 2.87 mmol) were added to the solution of compound c (500 mg, 1.58 mmol) in acetonitrile/water (10/2 ml) under stirring and the reaction mixture was stirred at 80° C. under Ar for 4 h. After the reaction was completed, the reaction mixture was quenched with water. After adding ethyl acetate (150 mL) to the reaction mixture to separate, the aqueous phase was extracted twice with ethyl acetate (50 mL×2). The combined organic phases were dried over Na$_2$SO$_4$ and concentrated. The resulting crude product was separated and purified by Combi-flash column chromatography to obtain 210 mg of the desired product 2-chloro-4-(1-methyl-1H-pyrrolo[2,3-b]pyridin-5-yl)-7-((2-trimethylsilyl)ethoxy)methyl)-7H-pyrrolo[2,3-d]pyrimidine g. MS m/z(ESI): 414.1 [M+H]$^+$.

Preparation of Compound h

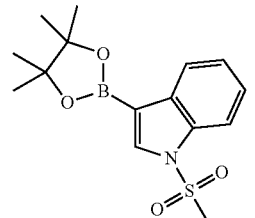

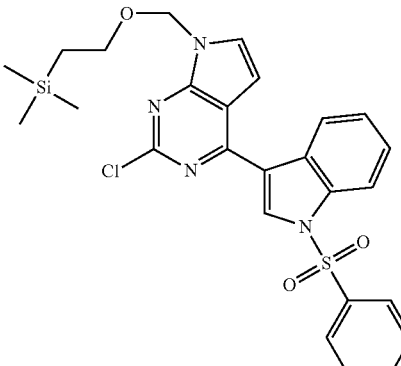

h-1

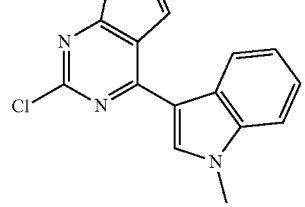

h-2

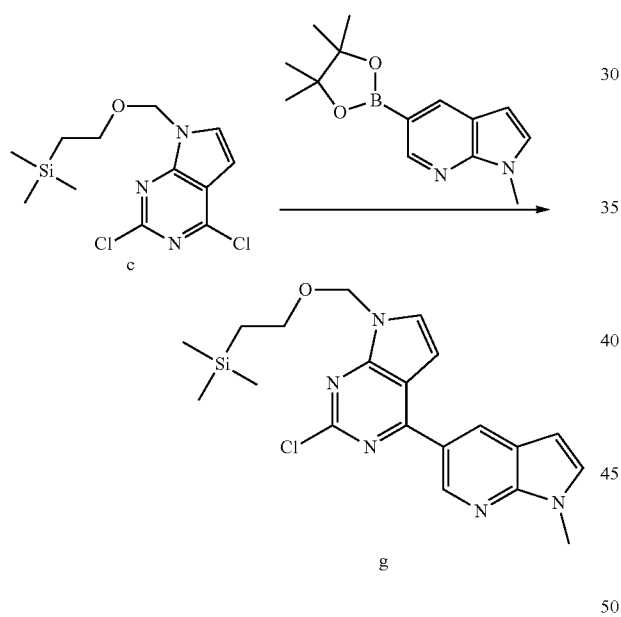

h

Step 1:
Compound h-1 (400 mg, yield 60%) was prepared from compound c (500 mg, 1.57 mmol) and compound 1-(phenylsulfonyl)-3-(4,4,5,5-tetramethyl-1,3,2-dioxaborolan-2-yl)-1H-indole (605 mg, 1.57 mmol) by referring to the method of preparation of compound g. MS m/z(ESI): 539 [M+H]$^+$.

Step 2:
Potassium hydroxide (365 mg, 6.5 mmol) was added to the solution of compound h-1 (350 mg, 0.65 mmol) in 20 mL of methanol. The reaction mixture stirred at room temperature for 4 hours. After the reaction as completed, the reaction mixture was adjusted to pH 7 with 2M HCl solution, concentrated, and extracted with water and ethyl acetate. The organic phase was washed with water and then saturated brine and concentrated under reduced pressure to give 300 mg of the objective compound h-2 which was used directly in the next step without purification. MS m/z(ESI): 399.2 [M+H]+.

Step 3:

At 0° C., compound h-2 (630 mg, 1.58 mmol) was added to the solution of sodium hydride (126 mg, 3.16 mmol) in THF (8 mL). The reaction mixture was stirred at 0° C. for 20 minutes. Iodomethane (337 mg, 2.37 mmol) was added. The reaction mixture was stirred at room temperature for 2 hours. After the reaction was completed, water was added at 0° C. to quench the reaction. The mixture was extracted with ethyl acetate, washed with water and then saturated sodium chloride solution and concentrated to give the crude product. After purified by Combi-flash column chromatography, 340 mg of the aimed product 2-chloro-4-(1-methyl-1H-indol-3-yl)-7-((2-(trimethylsilyl)ethoxy)methyl)-7H-prrolo[2,3-d]pyrimidine h was obtained. MS m/z(ESI): 413.3[M+H]+.

Preparation of Compound i

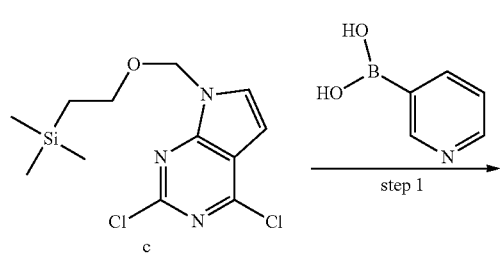

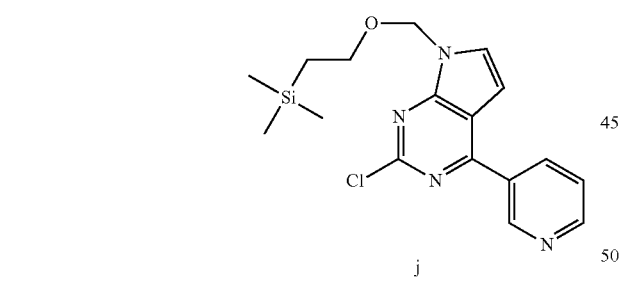

Pyridin-3-ylboronic acid (173 mg, 1.43 mmol), Pd(dppf)Cl₂ (116 mg, 0.14 mmol) and sodium carbonate (344 mg, 2.87 mmol) were added to the solution of compound c (500 mg, 1.58 mmol) in acetonitrile/water (10/2 mL), and the reaction mixture was subjected to a microwave reaction at 100° C. for 15 minutes. After the reaction was completed, the reaction mixture was quenched with water. After ethyl acetate (150 mL) was added to the reaction mixture to separate, the aqueous phase was extracted twice with ethyl acetate (50 mL×2). The combined organic phase was dried over Na₂SO₄. The resulting crude product was separated and purified by Combi-flash column chromatography to obtain 280 mg of the desired product 2-chloro-4-(pyridin-3-yl)-7-((2-(trimethylsilyl)ethoxy)methyl)-7H-pyrrolo[2,3-d]pyrimidine i. MS m/z(ESI): 361.1 [M+H]+.

Preparation of Compound j

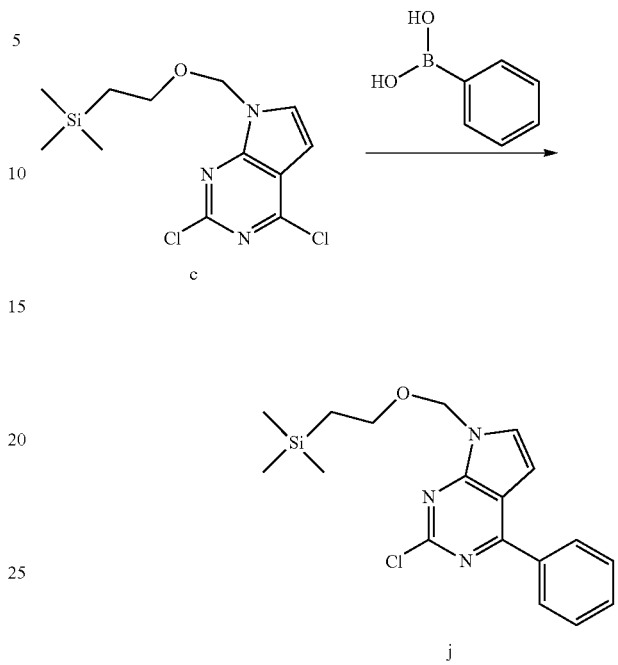

The title compound was prepared from compound c and phenylboronic acid as starting materials with reference to the preparation method of compound i. MS m/z(ESI): 360 [M+H]+.

Preparation of Compound k

Step 1:

Pd₂(dba)₃ (101 mg, 0.11 mmol), BINAP (137 mg, 0.22 mmol) and cesium carbonate (718 mg, 2.21 mmol) were added to the solution of compound d (500 mg, 1.10 mmol) and compound a (321 mg, 1.10 mmol) in 15 mL of 1,4-dioxane. The reaction mixture was subjected to a microwave reaction at 140° C. for 25 minutes. After the reaction was completed, the reaction mixture was filtered, washed with methylene chloride and the filtrate was concentrated under reduced pressure to give a crude product which was separated and purified by preparative liquid chromatography to give 700 mg of compound k-1, MS m/z(ESI): 711.3 [M+H]+.

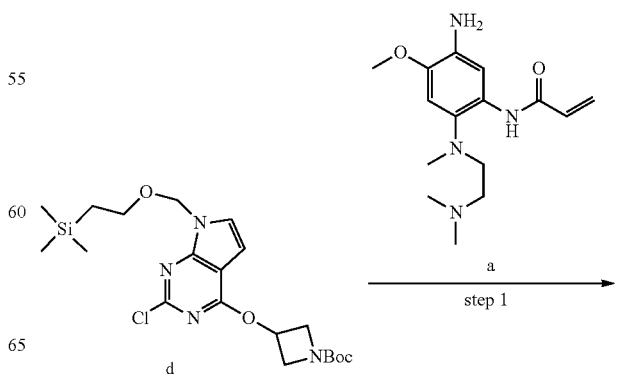

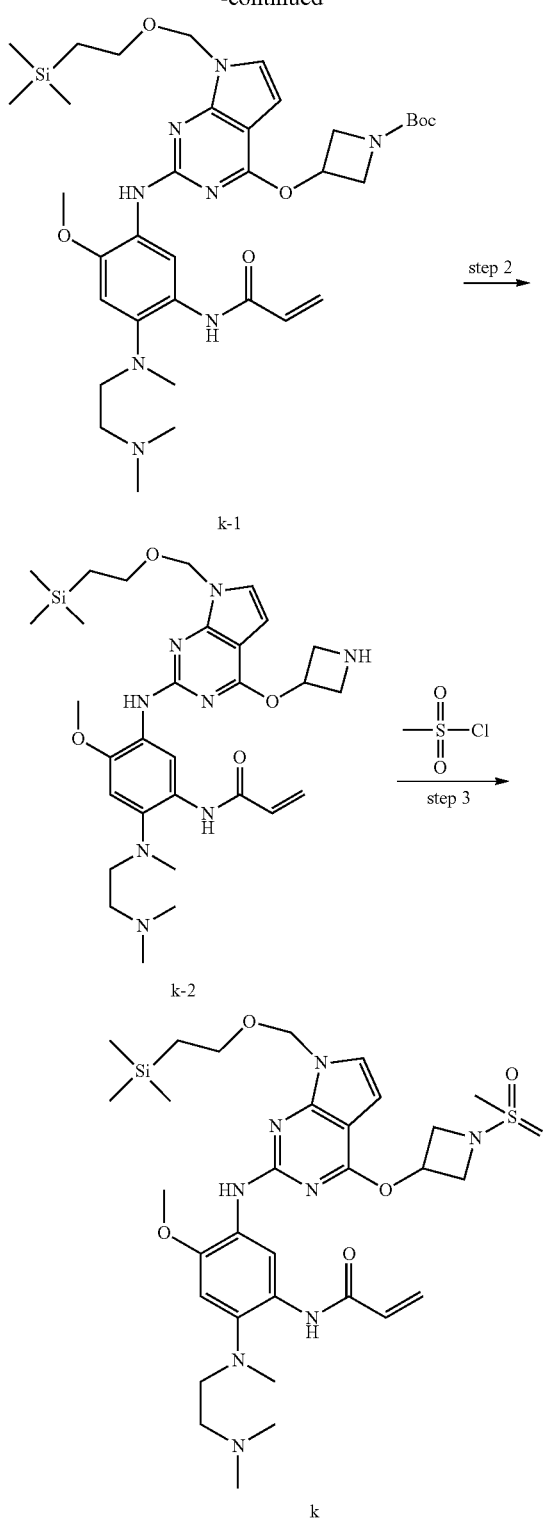

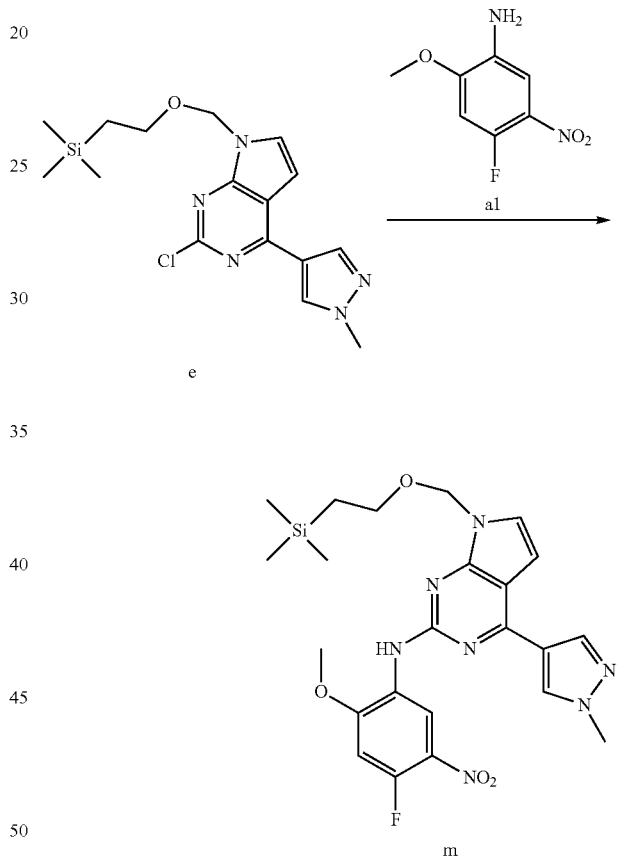

under reduced pressure to obtain 1.5 g of compound k-2, and the product was directly used in the next step. MS m/z(ESI): 611 [M+H]+.

Step 3:

Triethylamine (747 mg, 7.39 mmol) was added to a solution of compound k-2 (750 mg, 0.49 mmol) in 5 mL of methylene chloride (5 ml) at 0° C. and vigorously stirred at 0° C. for 30 minutes. Then methanesullonyl chloride (56 mg, 0.49 mmol) was added and vigorously stirred at 0° C. for 2 h. After the reaction was completed, water was added to dilute and the mixture was extracted three times with dichloromethane/water. The organic layer as concentrated under is reduced pressure and purified by combillash to give 90 mg of compound k. MS m/z(ESI):689.3 [M+H]+.

Preparation of Compound m

Step 2:

At 0° C., trifluoroacetic acid (1.124 g, 9.86 mmol) was added to the solution of compound k-1 (700 mg, 0.986 mmol) in 10 ml of dichloromethane and stirred vigorously for 2 hours at room temperature. After the reaction was completed, the reaction solution was evaporated to dryness Pd$_2$(dba)$_3$ (202 mg, 0.22 mmol), BINAP (274 mg, 0.44 mmol) and cesium carbonate (1.437 g, 4.41 mmol) were added to the solution of compound e (800 mg, 2.2 mmol) and compound a1 (410 mg, 2.2 mmol) in 10 mL of 1,4-dioxane. The reaction mixture was reacted under microwave at 140° C. for 25 minutes. After the reaction was completed, the reaction mixture was filtered, washed with dichloromethane, and the filtrate was concentrated under reduced pressure to give crude product which was purified by combiflash [PE:EA=100:0] to give 840 mg of compound N-(4-fluoro-2-methoxy-5-nitrophenyl)-4-(1-methyl-1H-pyrazol4-yl)-7-((2-(trimethylsilyl)ethoxy)methyl)-7H-pyrrolo[2,3-d]pyrrolo[2,3-d]pyrimidin-2-amine m. MS m/z (ESI): 514.2[M+H]+.

Preparation of Compound n

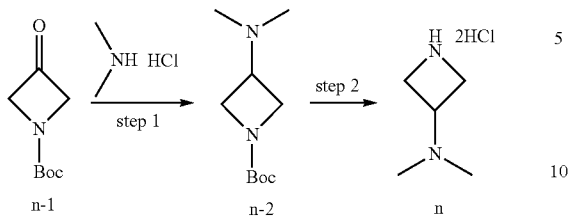

Step 1:

Compound n-1 (5.0 g, 0.0292 mmol), dimethylamine hydrochloride (4.77 g, 0.0584 mmol) 2.1 g of Pd/C and 2.5 ml of acetic acid were added to 100 ml of methanol under hydrogen atmosphere and reacted at room temperature for 48 hours after hydrogen purging. After the reaction was completed, the reaction mixture was filtered and concentrated to give a crude product. The mixture was extracted with saturated NaHCO$_3$ and ethyl acetate, washed with brine, and concentrated to give the object n-2 (5.0 g, yield 85%). MS m/z(ESI): 201 [M+H]$^+$.

Step 2:

To a solution of compound n-2 (5.0 g, 0.025 mmol) in dichloromethane (100 ml) was added a hydrochloric acid/1,4-dioxane solution (4 M) at 0° C. The reaction mixture was stirred at room temperature for 3 hours. After the reaction was completed, the mixture was concentrated to give the object N,N-dimethylazetidin-3-amine dihydrochloride n (3.5 g, 82%). MS m/z(ESI): 173 [M+H]$^+$.

Preparation of Compound p

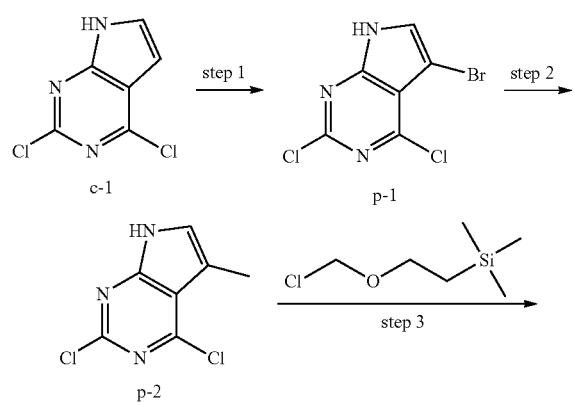

Step 1:

To a solution of compound c-1 (1 g, 5.32 mmol) in 80 mL of dichloromethane was added NBS (1.04 g, 5.85 mmol). The reaction mixture was stirred at room temperature for 4 hours. After the reaction was completed, the mixture was concentrated under reduced pressure and purified by combiflash to give compound p-1 (900 mg, yield 64%). MS m/z(ESI):266[M+H]$^+$.

step 2:

N-butyllithium (576 mg, 9 mmol) was slowly added dropwise to the solution of compound p-1 (800 m, 3 mmol) in 110 ml of THF at −70° C. After the reaction mixture was stirred for 1 how, iodomethane (511 mg, 3.6 mmol) was added at −70° C. and stirred at that temperature for another 1.5 hours. After the reaction was completed, the saturated ammonium chloride solution was added to quench at −70° C. The mixture was extracted with ethyl acetate, dried and concentrated under reduced pressure and then purified by combiflash to give 320 mg of compound p-2. MS m/z(ESI): 202[M+H]$^+$.

step 3:

Compound p-3 was prepared by using compound p-2 as a starting material and by a method for preparing compound c. MS m/z(ESI): 332[M+H]$^+$.

Step 4:

2-chloro-5-methyl-4-(1-methyl-1H-pyrazol-4-yl)-7-((2-(trimethylsilyl)ethoxy)methyl)-7H-pyrrolo [2,3-d] pyrimidine p was prepared by using compound p-3 as a starting material and by a method for preparing compound e. MS m/z(ESI): 378.2[M+H]$^+$.

Preparation of Compound r

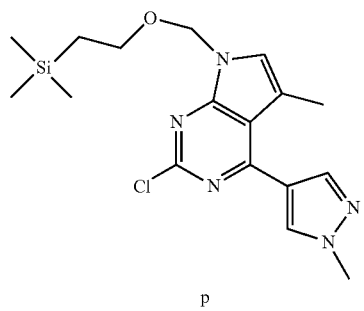

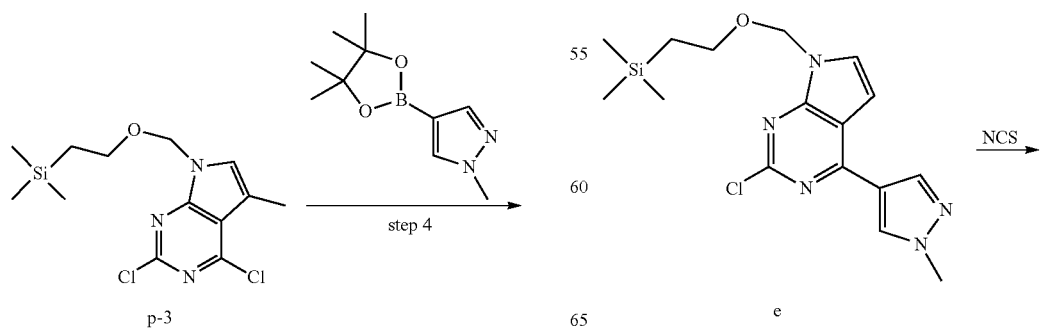

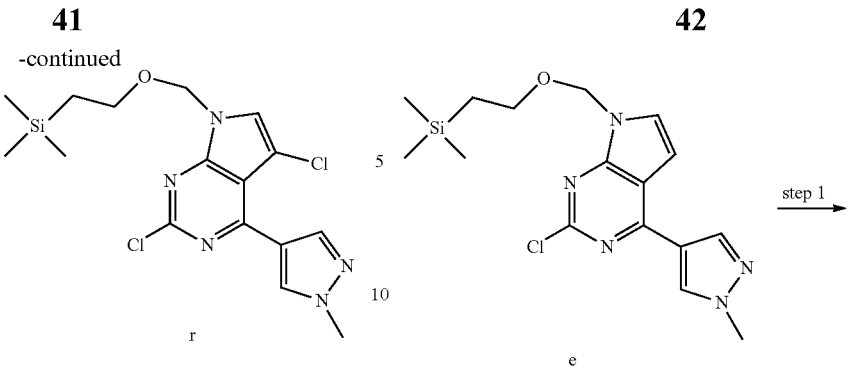

To the solution of compound e (410 mg, 1.12 mmol) in 10 mL of acetonitrile was added NCS (180 mg, 1.35 mmol). The reaction mixture was stirred at 70° C. for 2 hours. After the reaction was completed, the reaction mixture was concentrated and purified by combiflash to give the compound 2,5-dichloro-4-(1-methyl-1H-pyrazol-4-yl)-7-((2-trimethylsilyl)ethoxy) methyl)-7H-pyrrolo[2,3-d]pyrimidine r (300 mg, 67% yield). MS m/z(ESI): 398[M+H]+.

Preparation of Compound s

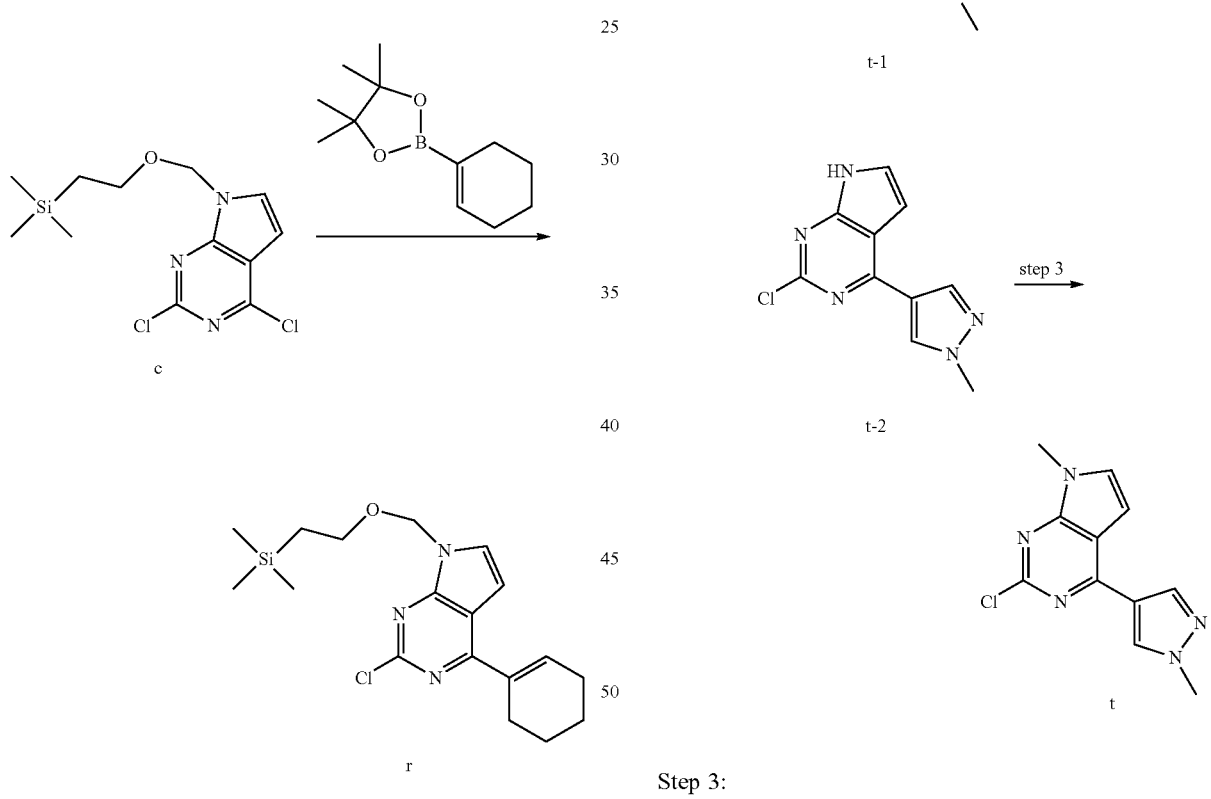

Compound 2-chloro-4-cyclohexenyl-7-((2-(trimethylsilyl)ethoxy)methyl)-7H-pyrrolo[2, 3-d]pyrimidine s was prepared by using compound c and 2-cyclohexenyloxy-4,4,5,5-tetramethyl-1,3,2-dioxaborolane as starting materials and by a method for preparing compound g. MS m/z(ESI): 364 [M+H]+.

Preparation of Compound t

Step 1-2

Compound t-2 was prepared in a similar manner to that of Example 3 using compound e as a starting material. MS m/z (ESL): 234 [M+H]+.

Step 3:

Sodium hydride (5 mg, 0.12 mmol) was added in one portion to the solution of compound t-2 (23.3 mg, 0.1 mmol) in 5 ml of DMF under ice-bath. The reaction mixture was stirred at 0° C. for 20 minutes and then methyl iodide (28.4 mg, 0.2 mmol) was dropwise added. The reaction solutim was warmed to room temperature and stirred for 2 hours. After the reaction was completed, the reaction mixture was quenched with water and extracted with ethyl acetate. The organic phase was dried over anhydrous sodium sulfate, concentrated and purified by combiflash to give the compound 2-chloro-7-methyl-4-(1-methyl-1H-pyrazol-4-yl-7H-pyrrolo[2,3-d]pyrimidine t (20 mg, 0.08 mmol). MS m/z (ESI): 248[M+H]+.

Preparation of Compound u

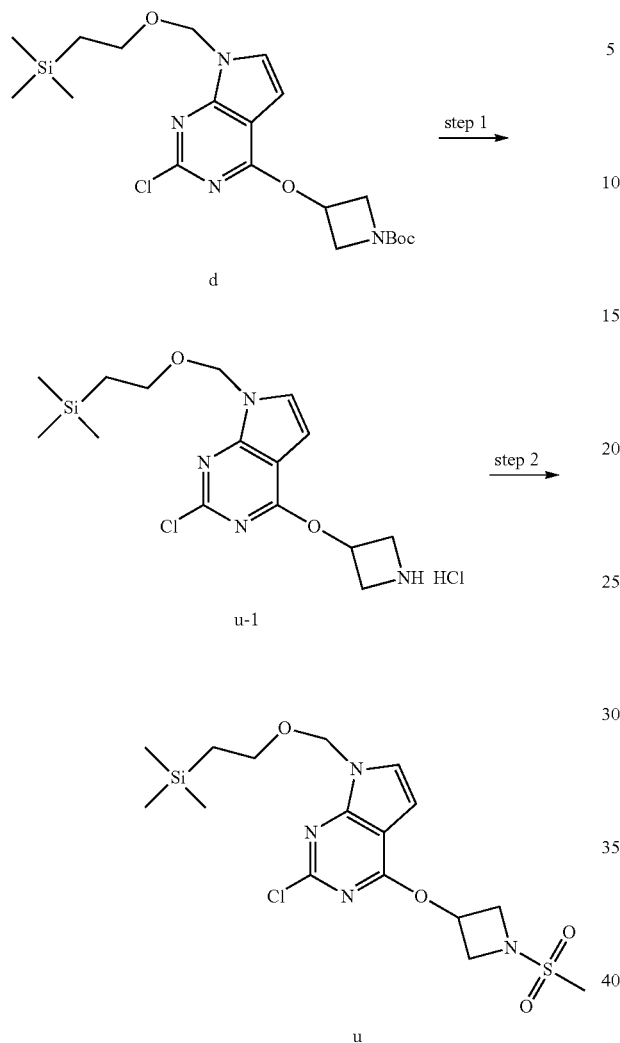

Preparation of Compound v

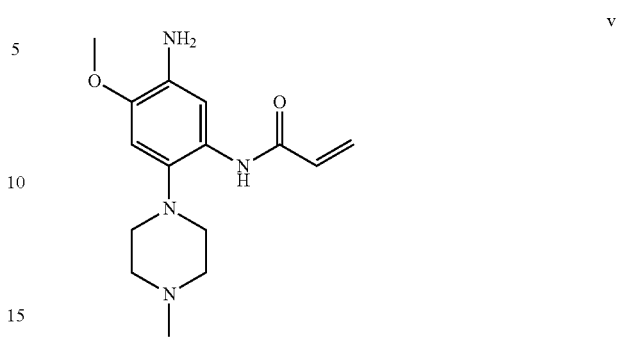

The preparation method was the same as that of compound a except that N,N,N'-trimethylethylenediamine in step 2 of the preparation method of compound a was replaced by 1-methylpiperazine. MS m/z(ESI): 291 [M+H]$^+$.

Preparation of Compound w

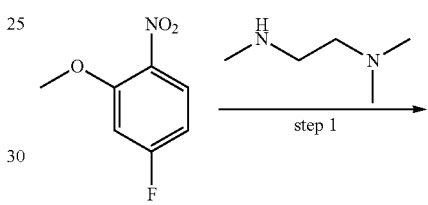

w1

Step 1

36% hydrochloric acid (0.5 ml, 4.9 mmol) was added to the solution of compound d (60 mg, 0.132 mmol) in 5 ml of methanol at 0° C. The reaction mixture was warmed to room temperature and stirred for 18 hours. After the reaction was completed, the reaction mixture was concentrated to give the crude product of compound u-1 which was used directly in the next reaction without purification. MS m/z(ESI): 355 [M+H]$^+$.

Step 2

N-diisopropylethylamine (610 mg, 4.72 mmol) was added to the solution of compound u-1 (460 mg, 1.18 mmol) in 20 ml of dichloromethane at 0° C. and stirred for 5 minutes. Then sulfonyl chloride (203 mg, 1.77 mmol) was added dropwise at 0° C. The reaction mixture was warmed to room temperature and stirred for 1 hour. After the reaction was completed, the mixture was concentrated to give a crude product which was purified by combiflash to give the compound 2-chloro-4-(1-(methylsulfonyl)azetidin-3-yloxy)-7-((2-(trimethylsilyl)ethoxy) methyl)-7H-pyrrolo[2,3-d]pyrimidine u (255 mg, yield 50%). MS m/z(ESI): 433 [M+H]$^+$.

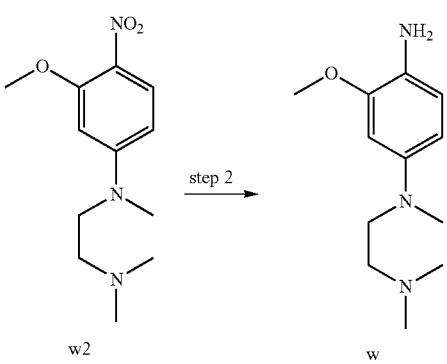

Compound w was prepared by using compound w1 and N,N,N'-trimethylethylenediamine as starting materials according to step 2 and step 3 in the preparation of compound a. Yield: 98%. MS m/z(ESI): 224 [M+H]$^+$.

EXAMPLE 1

The Preparation of N-(2-((2-(dimethylamino)ethyl)(methyl)amino)-4-methoxy-5-(4(1-methyl-1H-pyrazol-4-yl)-7H-pyrrolo[2,3-d]pyrimidn-2-ylamino)phenyl)acrylamide (1)

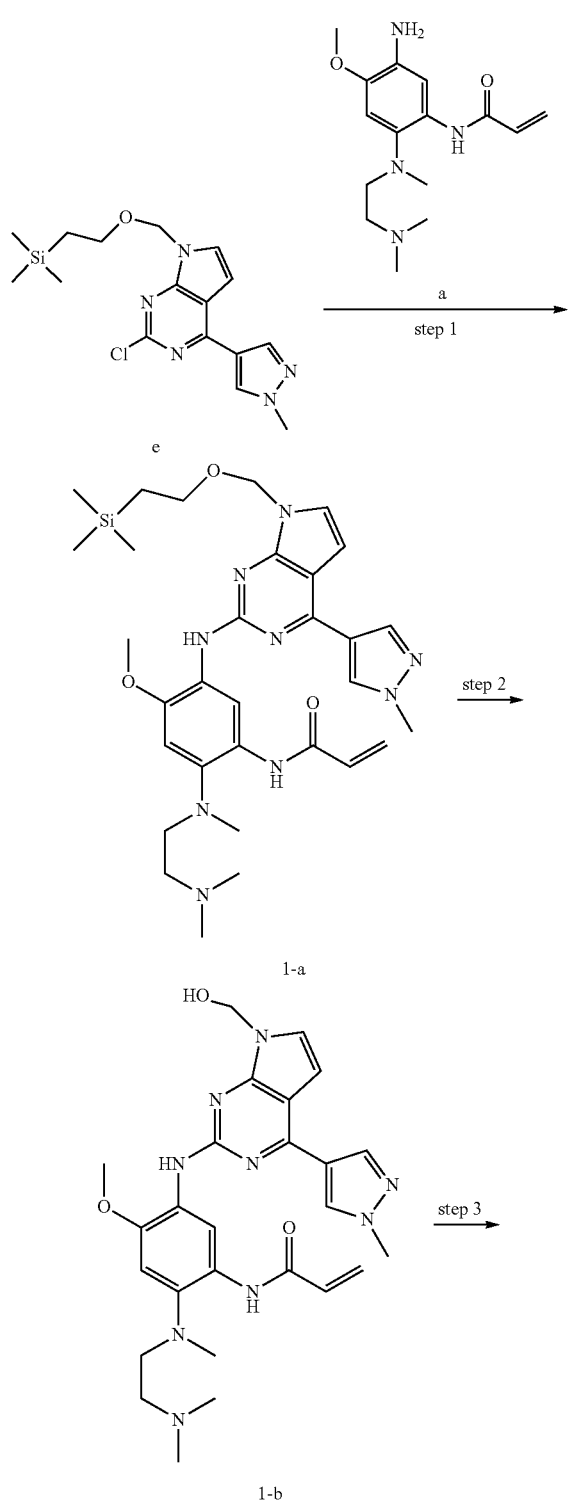

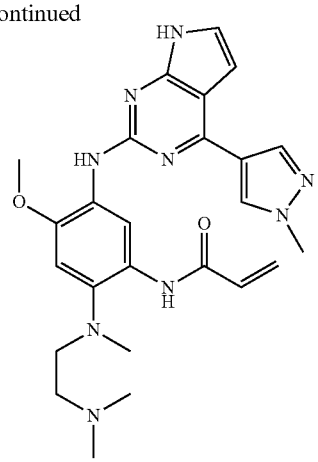

Step 1:

Compound e (100 mg, 0.27 mmol), compound a (80 mg, 0.27 mmol), $Pd_2(dba)_3$ (25 mg, 0.027 mmol), xantphos (28 mg, 0.054 mmol) and cesium carbonate (180 mg, 0.54 mmol) were placed into a 4 mL sealed tube reactor and 5 mL of 1,4-dioxane was added. Air was replaced by Ar for 1 minute and the sealed tube reactor was heated to 160° C. to react for 15 minutes. The reaction solution was filtered and the filter cake was washed with dichloromethane. The filtrate was concentrated to give a crude product which was purified and spanned by preparative liquid chromatography to give the object product 1-a (200 mg, yield 80%). MS m/z(ESI): 620[M+H]$^+$.

Step 2:

2 ml trifluoroacetic acid was added to the solution of compound 1-a (100 mg, 0.16 mmol) in 5 ml of dichloromethane and the reaction mixture was stirred at room temperature for 4 h. After the reaction was completed, the reaction solution was evaporated to dryness under reduced pressure to give compound 1-b (100 mg) which was directly used in the next step. MS m/z(ESI): 520 [M+1]$^+$.

Step 3:

Potassium carbonate (250 mg, 1.6 mmol) was added to the solution of compound 1-b (100 mg, 0.16 mmol) in ethanol/water (10/2 ml) and the reaction mixture was stirred at room temperature for 2 h. After the reaction was completed, the reaction solution was evaporated to dryness under reduced pressure and then extracted with ethyl acetate, dried over anhydrous $Na_2SO_4$ and concentrated to give a crude product which was purified and separated by preparative liquid chromatography to give title compound 1 (100 mg, yield 90%) as a yellow solid.

MS m/z(ESI): 490[M+H]$^+$. $^1$H NMR (400 MHz, CDCl$_3$) δ 10.24 (s, 1H), 9.91 (s, 1H), 9.06 (s, 1H), 8.95 (s, 1H), 8.20 (s, 1H), 7.63 (s, 1H), 7.05 (dd, J=3.5, 2.0 Hz, 1H), 6.78 (s, 1H), 6.66 (dd, J=3.5, 1.8 Hz, 1H), 6.45-6.24 (m, 2H), 5.71 (d, J=11.8 Hz, 1H), 4.06 (s, 3H), 3.90 (s, 3H), 2.91 (s, 2H), 2.71 (s, 3H), 2.26 (overlap, 8H).

EXAMPLE 2

The Preparation of N-(2-((2-(dimethylamino)ethyl)(methyl)amino)-4-methoxy-5-(4-morpholino-7H-pyrrolo[2,3-d]pyrimidin-2-ylamino)phenyl)acrylamide (2)

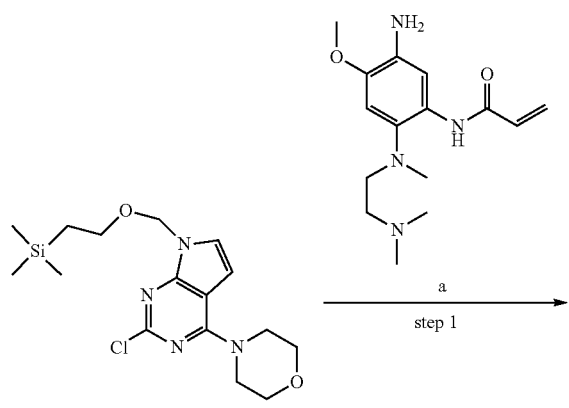

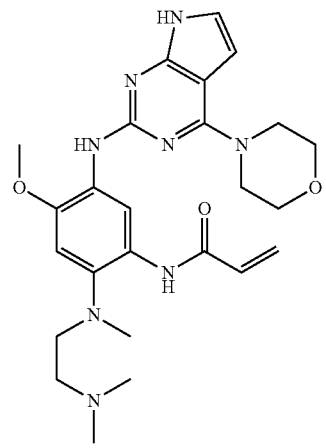

The title compound 2 as a yellow solid was prepared from compound f and compound a according to Example 1. MS m/z(ESI): 495 [M+H]$^+$; $^1$H NMR (400 MHz, CDCl$_3$) δ 10.04 (s, 1H), 9.62 (s, 1H), 9.12 (s, 1H), 7.24 (s, 1H), 6.74 (dd, J=3.5, 2.1 Hz, 1H), 6.68 (s, 1H), 6.35-6.29 (m, 2H), 6.26 (s, 1H), 5.60 (d, J=11.8 Hz, 1H), 3.95-3.89 (m, 4H), 3.82-3.80 (m, 4H), 3.80 (s, 3H), 2.81 (t, J=5.6 Hz, 2H), 2.62 (s, 3H), 2.18 (overlap, 8H).

EXAMPLE 3

The Preparation of N-(2-((2-(dimethylamino)ethyl)(methyl)amino)-4-methoxy-5-(4-(1-(methylsulfonyl)azetidin-3-yloxy)-7H-pyrrolo[2,3-d]pyrimidin-2-ylamino)phenyl)acryl amide (3)

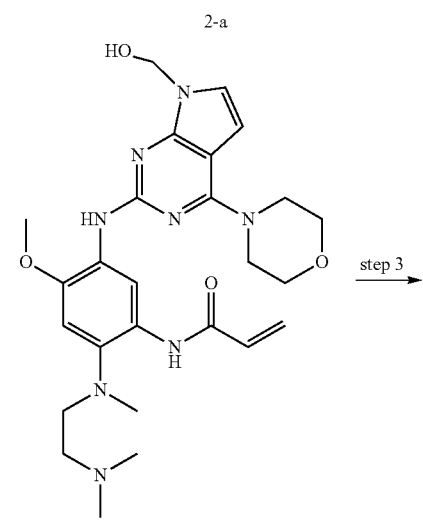

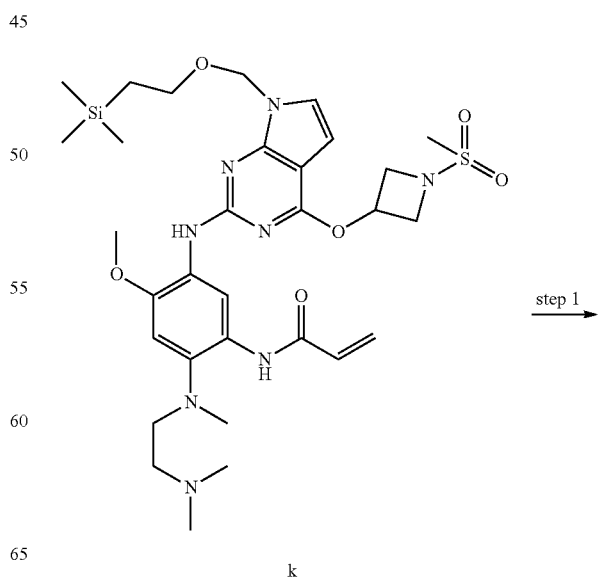

-continued

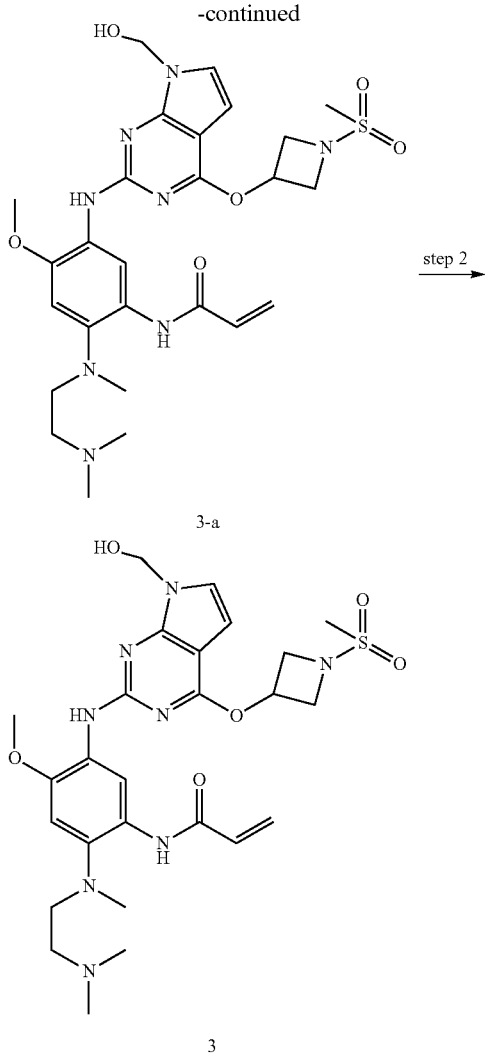

Step 1:

At 0° C., 3 ml of trifluoroacetic acid was added to the solution of compound k (90 mg, 0.13 mmol) in 3 ml of dichloromethane and stirred at 40° C. for 3 h. After the reaction was completed, the reaction solution was concentrated to give a crude product which was directly used in the next reaction without purification.

step 2:

At 0° C., the crude product of step 1 was dissolved in 3 ml of methanol and then 3 ml ammonia was added. The reaction mixture was stirred at 40° C. for 3 h. After the reaction was completed, the reaction solution was concentrated to give, a crude product which was purified and separated by preparative liquid chromatography to give 6 mg of title compound 3 as a white solid. MS m/z(ESI): 559.2 [M+H]$^+$. $^1$H NMR (400 MHz, DMSO-d$_6$) δ 11.47 (s, 1H), 10.19 (s, 1H), 8.95 (s, 1H), 7.63 (s, 1H), 7.06-7.02 (m, 1H), 7.00 (s, 1H), 6.39 (dd, J=16.9, 9.9 Hz, 1H), 6.34 (dd, J=3.5, 1.9 Hz, 1H), 6.33-6.25 (m, 1H), 5.76 (d, J=12.0 Hz, 1H), 5.68 (s, 1H), 4.33-4.23 (m, 2H), 3.99 (dd, J=9.7, 4.8 Hz, 2H), 3.86 (s, 3H), 3.03 (s, 3H), 2.85 (d, J=6.1 Hz, 2H), 2.70 (s, 3H), 2.27 (t, J=5.6 Hz, 2H), 2.20 (s, 6H).

EXAMPLE 4

The Preparation of N-(2-((2-(dimethylamino)ethyl) (methyl)amino)-4-methoxy-5-(4-(1-methyl-1H-pyrrolo[2,3-b]pyridin-5-yl)-7H-pyrrolo[2,3-d]pyrimidin-2-ylamino)phenyl)acrylamide (4)

Step 1:

Pd$_2$(dba)$_3$ (46 mg, 0.05 mmol), BINAP (63 mg, 0.12 mmol) and cesium carbonate (332 mg, 1.02 mmol) were added to the solution of compound g (210 mg, 0.51 mmol) and compound a (148 mg, 0.51 mmol) in 10 mL of 1,4-dioxane. The reaction mixture was subjected to a microwave reaction at 140° C. for 30 minutes. After the reaction was completed, the reaction mixture was filtered and rinsed with dichloromethane. The filtrate was concentrated under reduced pressure to give a crude product which was purified by combiflash [PE:EA=90:10] to give 270 mg of compound 4-a. MS m/z(ESI): 670.5[M+H]$^+$.

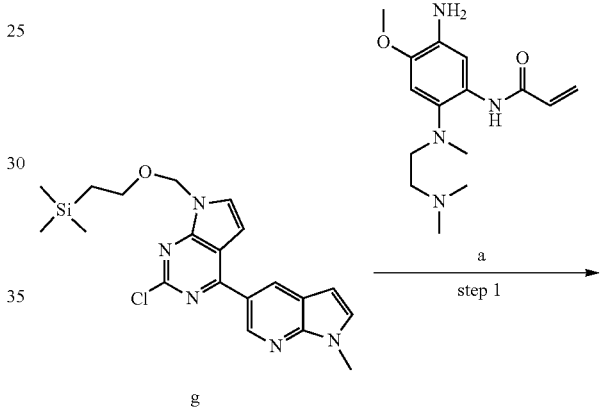

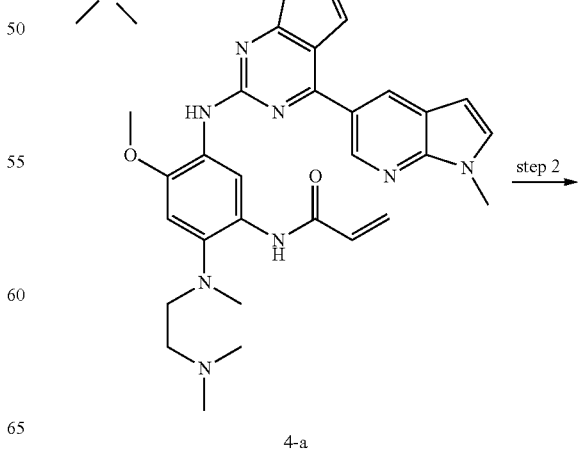

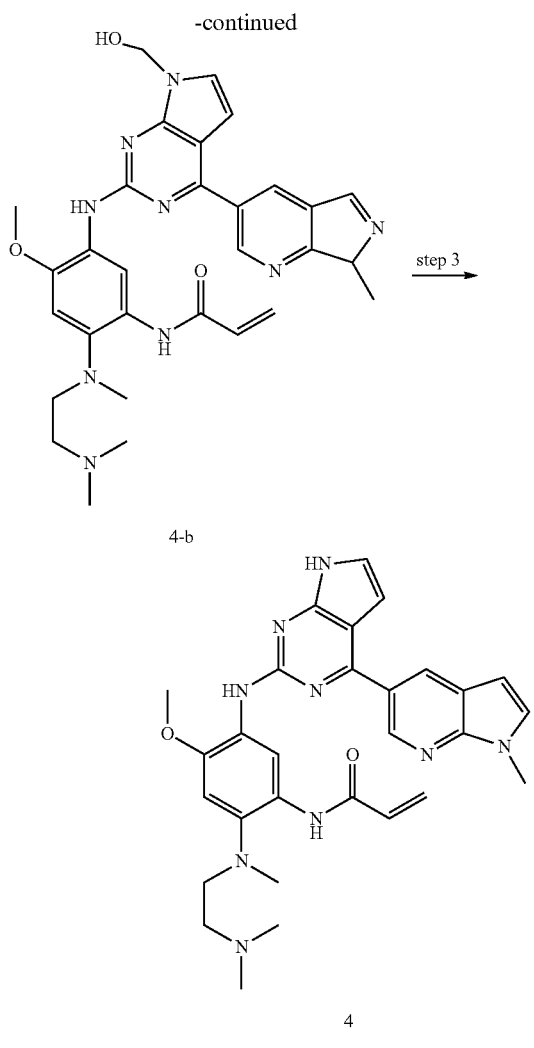

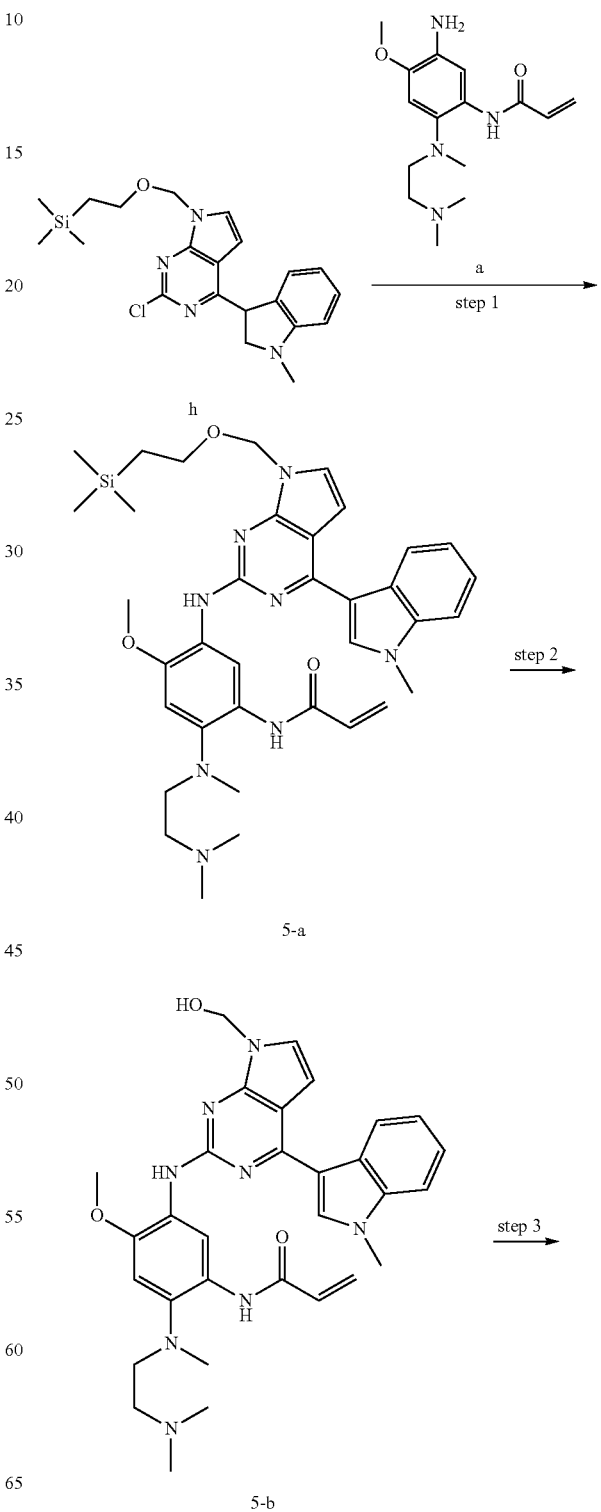

Step 2 and Step 3

41 mg of title compound 4 as a pale yellow solid was obtained by using compound 4-a as the starting material according to the method of step 1 and 2 in Example 3. MS m/z(ESI): 540.2 [M+H]+; 1H NMR (400 MHz, DMSO-d6) δ 11.61 (s, 1H), 10.17 (s, 1H), 9.24 (s, 1H), 9.09 (d, J=1.9 Hz, 1H), 8.97 (s, 1H), 7.71 (s, 1H), 7.62 (d, J=3.4 Hz, 1H), 7.29 (s, 1H), 7.02 (s, 1H), 6.80 (s, 1H), 6.61 (d, J=3.4 Hz, 1H), 6.42 (d, J=9.6 Hz, 1H), 6.33 (d, J=14.6 Hz, 1H), 5.80 (d, J=10.0 Hz, 1H), 3.90 (s, 3H), 3.90 (s, 3H), 2.88 (s, 2H), 2.71 (s, 3H), 2.29 (s, 2H), 2.21 (s, 6H).

EXAMPLE 5

The Preparation of N-(2-((2-(dimethylamino)ethyl)(methyl)amino)-4-methoxy-5-(4-(1-methyl-1H-indol-3-yl)-7H-pyrrolo[2,3-d]pyrimidin-2-ylamino)phenyl)acrylamide (5)

The crude title compotind 5 was prepared by using compound h and compound a according to the method of Example 4. The obtained crude product was purified by preparative liquid chromatography [H2O (0.05 vol % formic acid): CH3CN=85:15-90:10] to give the formate of title compound 5 as a yellow solid. MS m/z(ESI): 539 [M+H]+; 1H NMR (400 MHz, CDCl3) δ 10.05 (s, 1H), 9.92 (s, 1H), 9.59 (s, 1H), 8.53 (s, 1H) 8.48 (d, J=7.5 Hz, 1H), 8.04 (s, 1H), 7.77 (s, 1H), 7.41-7.37 (m, 1H), 7.32 (d, J=5.8 Hz, 1H), 7.30-7.28 (m, 1H), 7.04 (d, J=3.3 Hz, 1H), 6.84 (dd, J=16.9, 10.2 Hz, 1H), 6.68 (s, 1H), 6.65 (d, J=3.3 Hz, 1H), 6.44 (dd, J=16.9, 1.6 Hz, 1H), 5.74 (dd, J=10.2, 1.5 Hz, 1H), 3.92 (s, 3H), 3.90 (s, 3H), 3.16 (t, J=5.7 Hz, 2H), 2.90 (t, 5.6 Hz, 2H), 2.63 (s, 3H), 2.62 (overlap, 6H).

53
-continued
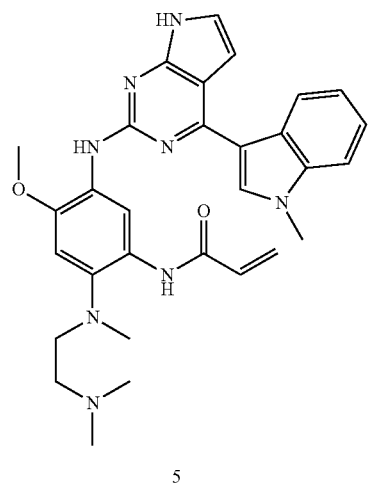 [SMILES: C=CC(=O)Nc1cc(Nc2nc(-c3cn(C)c4ccccc34)c3cc[nH]c3n2)c(OC)cc1N(C)CCN(C)C]
5
EXAMPLE 6
The Preparation of N-(2-((2-(dimethylamino)ethyl)(methyl)amino)-4-methoxy-5-(4-(pyridin-3-yl)-7H-pyrrolo[2,3-d]pyrimidin-2ylamino)phenyl)acrylamide (6)
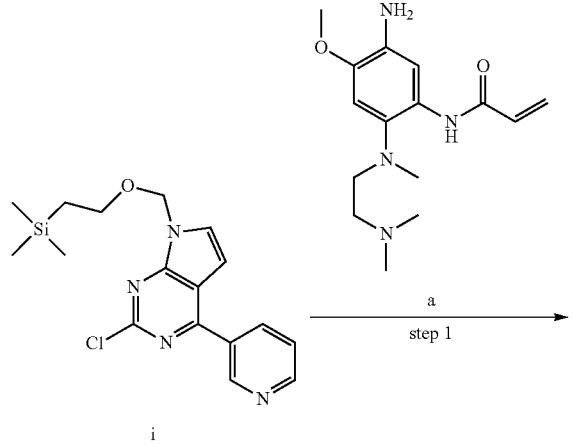
54
-continued
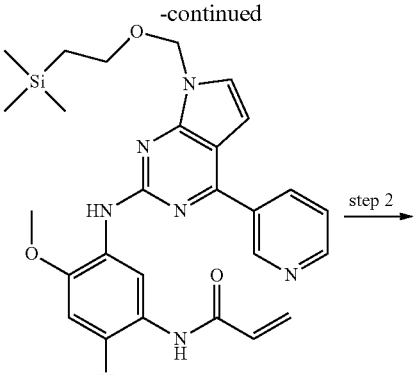
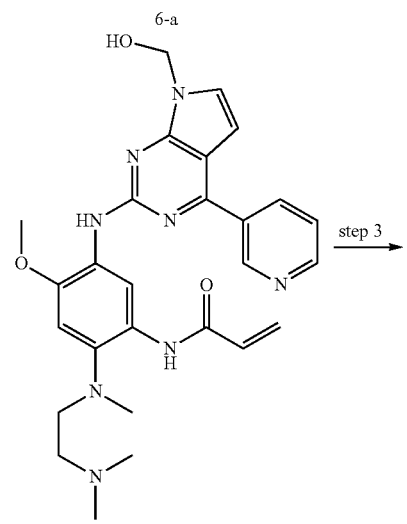
6-b
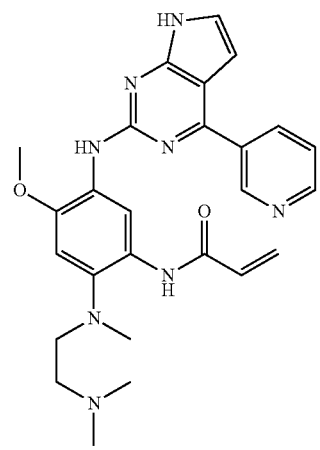
6
The title compound 6 as a pale yellow solid was prepared from compound i and compound a according to the method of Example 7. MS m/z(ESI): 487.2 [M+H]$^+$; $^1$H NMR (400 MHz, DMSO-d$_6$) δ 11.87 (s, 1H), 10.31 (s, 1H), 9.51 (s, 1H), 9.31 (s, 1H), 8.88 (t, J=5.8 Hz, 2H), 7.95 (s, 1H), 7.74 (dd, J=7.6, 5.0 Hz, 1H), 7.48 (s, 1H), 7.17 (s, 1H), 6.93 (d, J=2.8

Hz, 1H), 6.57 (dd, J=16.9, 9.9 Hz, 1H), 6.46 (d, J=16.6 Hz, 1H), 5.94 (d, J=10.0 Hz, 1H), 4.04 (s, 3H), 3.04 (s, 2H), 2.87 (s, 3H), 2.46 (s, 2H), 2.37 (s, 6H).

EXAMPLE 7

The Preparation of N-(2-((2-(dimethylamino)ethyl)(methyl)amino)-4-methoxy-5-(4-phenyl-7H-pyrrolo[2,3-d]pyrimidin-2-ylamino)phenyl)acrylamide (7)

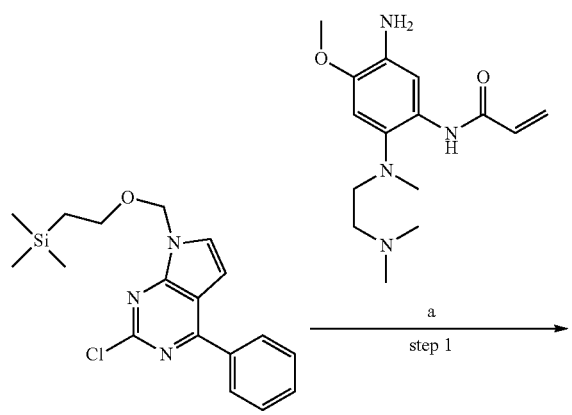

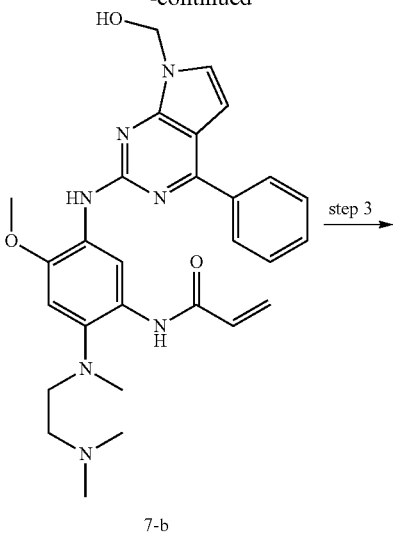

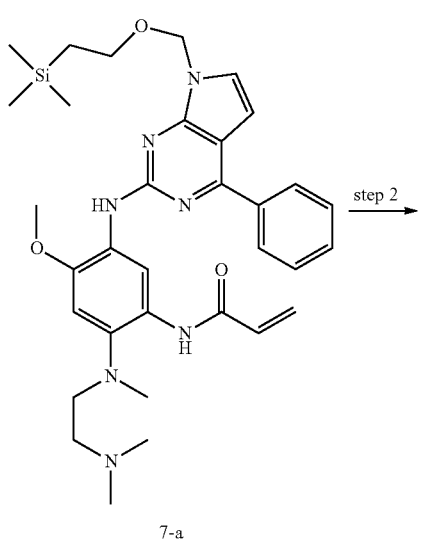

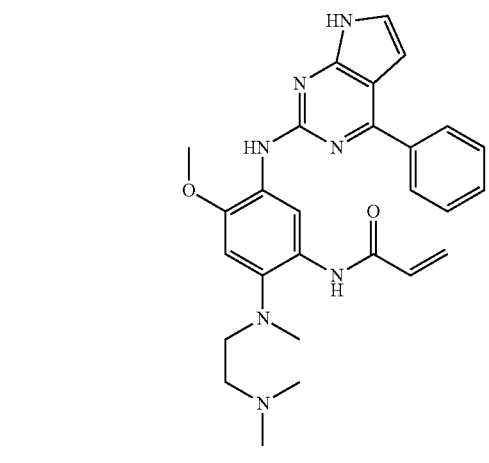

The tide compound 7 as a yellow solid was prepared from compound j and compound a according to the method of Example 4. MS m/z(ESI): 486.2 [M+H]⁺; ¹H NMR (400 MHz, DMSO-d$_6$) δ 11.79 (s, 1H), 10.30 (s, 1H), 9.36 (s, 1H), 8.44 (dd, J=7.4, 2.0 Hz, 2H), 7.86 (s, 1H), 7.75-7.69 (m, 3H), 7.44 (dd, J=3.5, 2.1 Hz, 1H), 7.16 (s, 1H), 6.88 (dd, J=3.5, 1.3 Hz, 1H), 6.58 (dd, J=16.9, 9.9 Hz, 1H), 6.47 (dd, J=16.9, 2.2 Hz, 1H), 5.94 (dd, 9.9, 2.2 Hz, 1H), 4.05 (s, 3H), 3.03 (s, 2H), 2.86 (s, 3H), 2.45 (s, 2H), 2.37 (s, 6H).

EXAMPLE 8

The Preparation of N-(5-(4-cyclohexenyl-7H-pyrrolo[2,3-d]pyrimidin-2-ylamino)-2-((2-(dimethylamino)ethyl)(methyl)amino)4-methoxyphenyl)acrylamide (8)

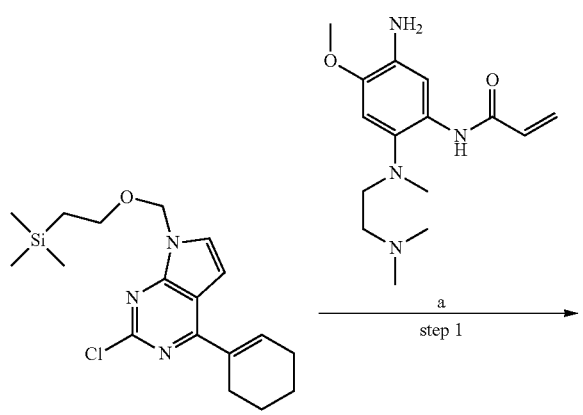

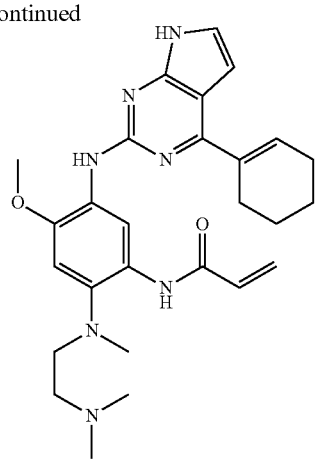

The tide compound 8 as a yellow solid was prepared from compound s and compound a according to the method of Example 4. MS m/z(ESI): 490.3 [M+H]$^+$.

EXAMPLE 9

The Preparation of N-(2-(4-(dimethylamino)piperidin-1-yl)-4-methoxy-5-(4-(1-methyl-1H-pyrazol-4-yl)-7H-pyrrolo[2,3-D]pyrimidin-2-ylamino)phenyl)acrylamide (9)

Step 1:

Compound e (100 mg, 0.275 mmol), compound b (87 mg, 0.275 mmol), Pd$_2$(dba)$_3$ (26 mg, 0.028 mmol), xantphos (32 mg, 0.056 mmol) and cesium carbonate (185 mg, 0.56 mmol) were placed into a 4 mL sealed tube reactor and 5 mL of 1,4-dioxane was added. Air was replaced by Ar for 1 minute and the sealed tube reactor was heated to 160° C. to react for 15 minutes. The reaction solution was filtered and the filter cake was washed with dichloromethane. The filtrate was concentrated to give a crude product which was purified and separated by preparative liquid chromatography to give the object product 9-a (200 mg, yield 70%). MS m/z(ESI): 646[M+H]$^+$.

Step 2-3

The crude tide compound 9 was prepared from compound 9-a according to step 1 and 2 of Example 3. The obtained crude product was purified by preparative liquid chromatography [H$_2$O(0.05 vol % formic acid):CH$_3$CN=80:20-90:10] to give title compound 9 formate as a yellow solid. MS m/z(ESI): 516[M+H]$^+$. $^1$H NMR (400 MHz, DMSO-d$_6$) δ 11.46 (s, 1H), 9.16 (s, 1H), 9.08 (s, 1H), 8.90 (s, 1H), 8.35 (s, 1H), 8.18 (s, 1H), 7.46 (s, 1H), 7.22 (dd, J=3.4, 2.3 Hz, 1H), 6.86 (s, 1H), 6.81 (dd, J=3.4, 1.5 Hz, 1H), 6.72 (dd, J=17.1, 10.0 Hz, 1H), 6.33 (d, J=16.6 Hz, 1H), 5.79 (d, J=11.0 Hz, 1H), 3.97 (s, 3H), 3.91 (s, 3H), 3.05 (d, J=11.0 Hz, 2H), 2.70 (t, J=11.1 Hz, 2H), 2.56 (overlap, 1H), 2.44 (s, 6H), 1.92 (d, J>10.6 Hz, 2H), 1.77 (m, 2H).

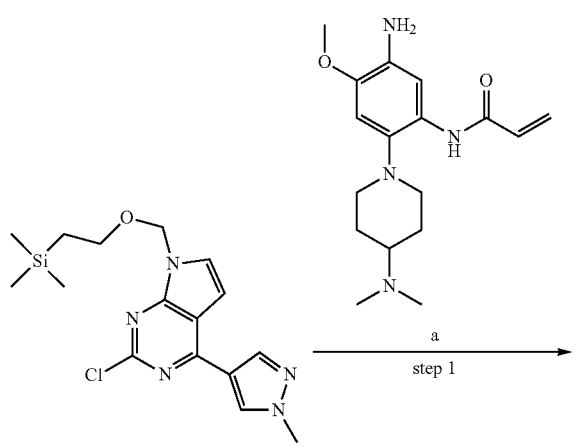
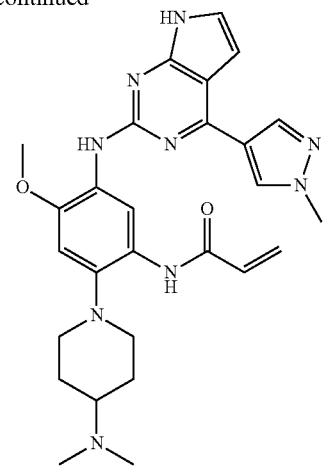
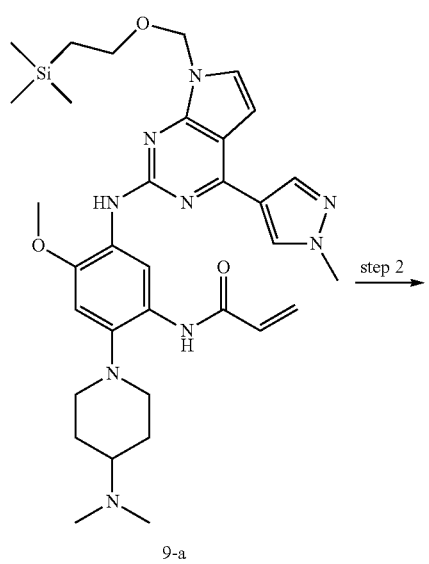
EXAMPLE 10
The Preparation of N-(2-(2-(dimethylamino)ethoxy)-4-methoxy-5-(4-(1-methyl-1H-pyrazol-4-yl)-7H-pyrrolo[2,3-d]pyrimidin-2-ylamino)phenyl)acrylamide (10)
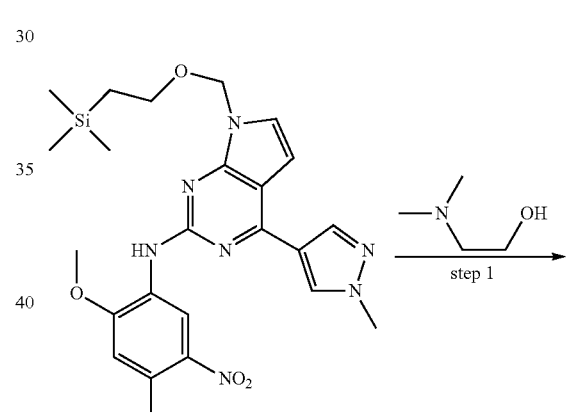
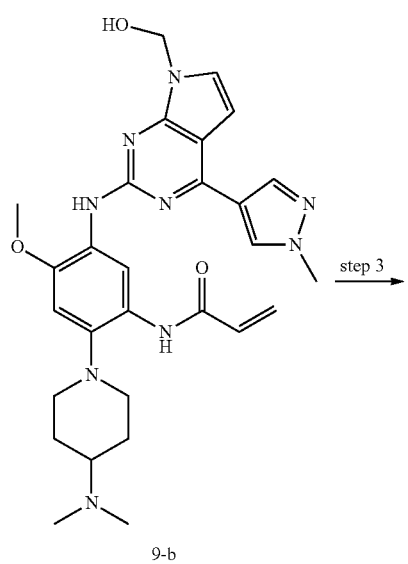
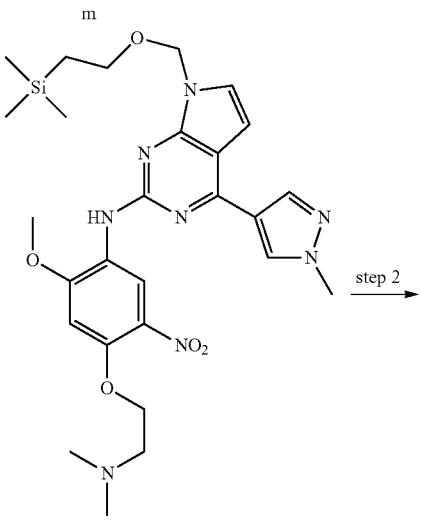

61

-continued

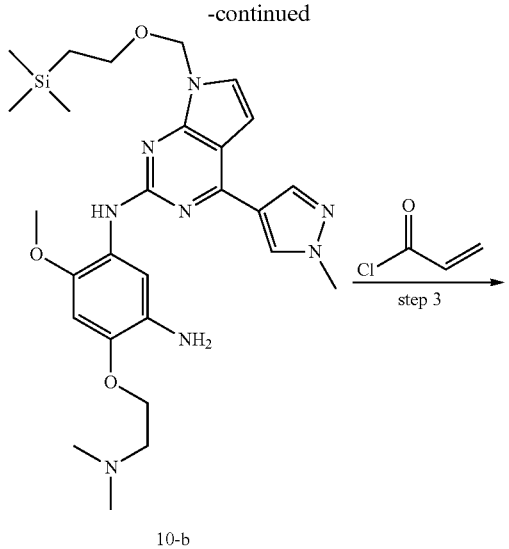

10-b

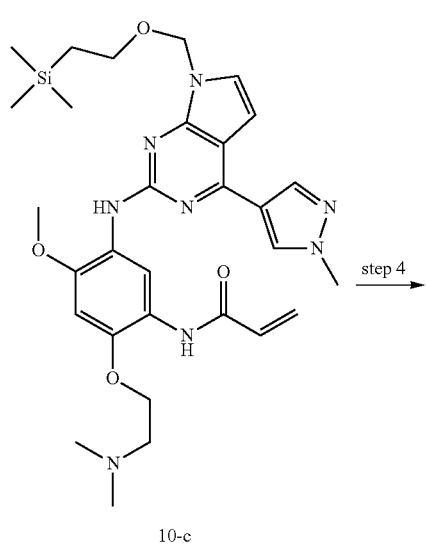

10-c

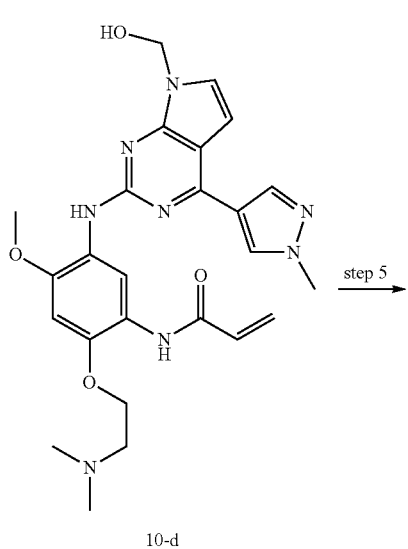

10-d

62

-continued

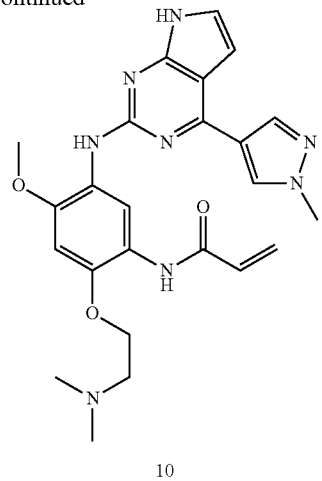

10

Step 1:

At 0° C., sodium hydride (9 mg, 1.72 mmol) was added to the solution of 2-(dimethylamino)ethanol (104 mg, 1.17 mmol) in 10 mL of THF and the mixture was stirred at 0° C. for 30 min. Compound m (400 mg, 0.78 mmol) was added and the reaction mixture as stirred at room temperature for 4 hours. After the reaction was completed, the mixture was extracted with ethyl acetate and water. The organic phase was washed with water and saturated sodium chloride solution. The organic phase was concentrated and purified by combiflash [dichloromethane:methanol=90:10] to give 400 mg of compound 10-a. MS m/z(ESI): 583.2[M+H]$^+$.

Step 2:

Pd/C(1 mg) was added to the solution of compound 10-a (10 mg, 0.017 mmol) in 5 mL of methanol. At room temperature, the mixture was stirred under H$_2$ for 4 h. After the reaction was completed, the mixture was filtered. The filtrate was concentrated to give 10 mg of compound 10-b which was directly used in the next step. MS m/z(ESI): 553.2[M+H]$^+$.

Step 3:

At 0° C., acryloyl chloride (137 mg, 0.74 mmol) and triethylamine (203 mg, 2.01 mmol) were added to the solution of compound 10-b (60 mg, 0.117 mmol) in 15 mL dichloromethane and stirred at 0° C. for 2 h. After the reaction was completed, water was added to dilute and the mixture was extracted three times with dichloromethane/water system. The organic layer was concentrated under reduced pressure to obtain a crude product which was purified and separated by preparative liquid chromatography to give compound 10-c. MS m/z(ESI): 607.2[M+H]$^+$.

Step 4 and 5:

The title compound 10 as a pale yellow solid was prepared from compound 10-c according to step 1 and 2 of Example 3. MS m/z(ESI): 490[M+H]$^+$. $^1$H NMR (400 MHz, DMSO-d$_6$) δ 11.45 (s, 1H), 9.90 (s, 1H), 9.18 (s, 1H), 8.89 (s, 1H), 8.34 (s, 1H), 7.44 (s, 1H), 7.25-7.16 (m, 1H), 6.93 (s, 1H), 6.85-6.77 (m, 1H), 6.48 (dd, J=17.0, 10.0 Hz, 1H), 6.39-6.23 (m, 1H), 5.85-5.74 (m, 1H), 4.16 (t, J=5.5 Hz, 2H), 3.97 (s, 3H), 3.91 (s, 3H), 2.55 (d, 5.6 Hz, 2H), 2.28 (s, 6H).

EXAMPLE 11

The Preparation of N-(2-(3-(dimethylamino)azetidin-1-yl)-4-methoxy-5-(4-(1-methyl-1H-pyrazol-4-yl)-7H-pyrrolo[2,3-d]pyrimidin-2-ylamino)phenyl)acrylamide Formate (11)

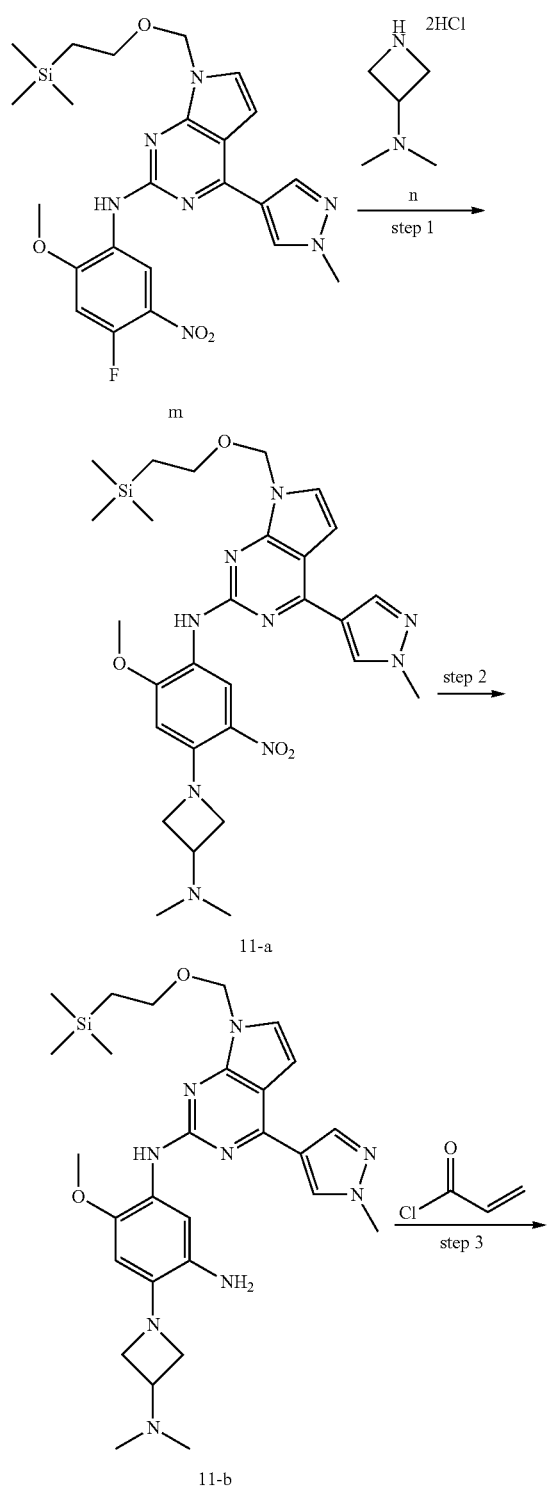

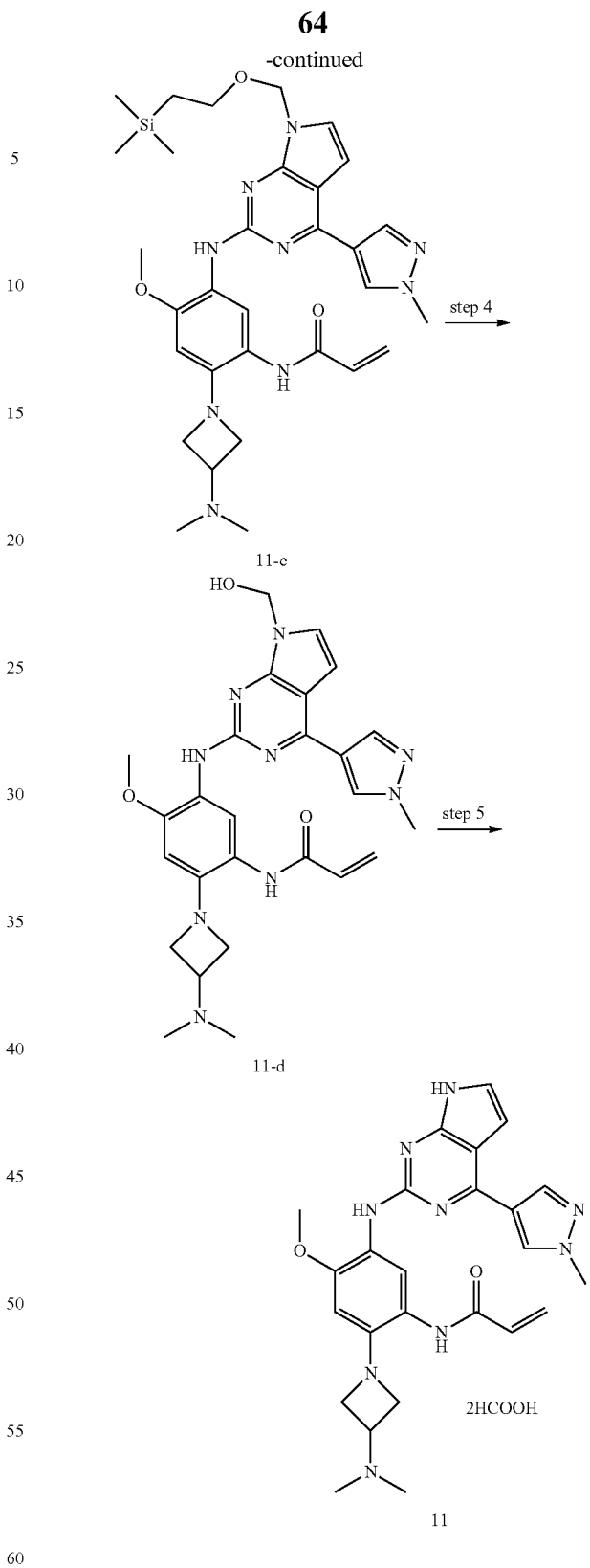

Step 1:

Compound in (400 mg, 0.78 mmol), compound n (400 mg, 2.3 mmol) and potassium carbonate (861 mg, 6.24 mmol) were added to 25 ml of DMF and stirred at 100° C. for 2 h. After the reaction was completed, the mixture was filtered. The filtrate was extracted with ethyl acetate and the organic phase was concentrated and purified by Combi-flash column chromatography to give compound 11-a (310 mg, yield 67%). MS m/z(ESI): 594 [M+H]$^+$.

Step 2-5

The title compound 11 as a pale yellow solid was prepared from compound 11-a according to step 2-5 of Example 10. MS m/z(ESI): 488[M+H]$^+$, $^1$HNMR(400 MHz, DMSO-d$_6$) δ 11.45 (s, 1H), 9.33 (s, 1H), 8.65 (s, 1H), 8.28 (s, 1H), 8.23 (s, 3H), 7.34 (s, 1H), 7.20-7.14 (m, 1H), 6.76 (d, J=2.0 Hz, 1H), 6.54 (dd, J=17.0, 10.2 Hz, 1H), 6.32-6.23 (m, 2H), 5.73 (dd, J=10.2, 2.0 Hz, 1H), 3.96-3.89 (m, 8H), 3.53 (d, J=6.7 Hz, 2H), 3.07-3.04 (m, 2.08 (s, 6H).

EXAMPLE 12

The Preparation of N-(4-methoxy-5-(4-(1-methyl-1H-pyrazol-4-yl)-7H-pyrrolo[2,3-d]pyrimidin-2-ylamino)-2-(4-methylpiperazin-1-yl)phenyl)acrylamide (12)

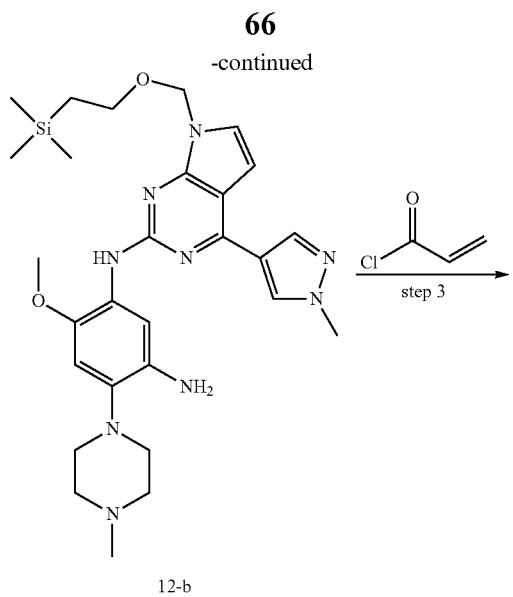

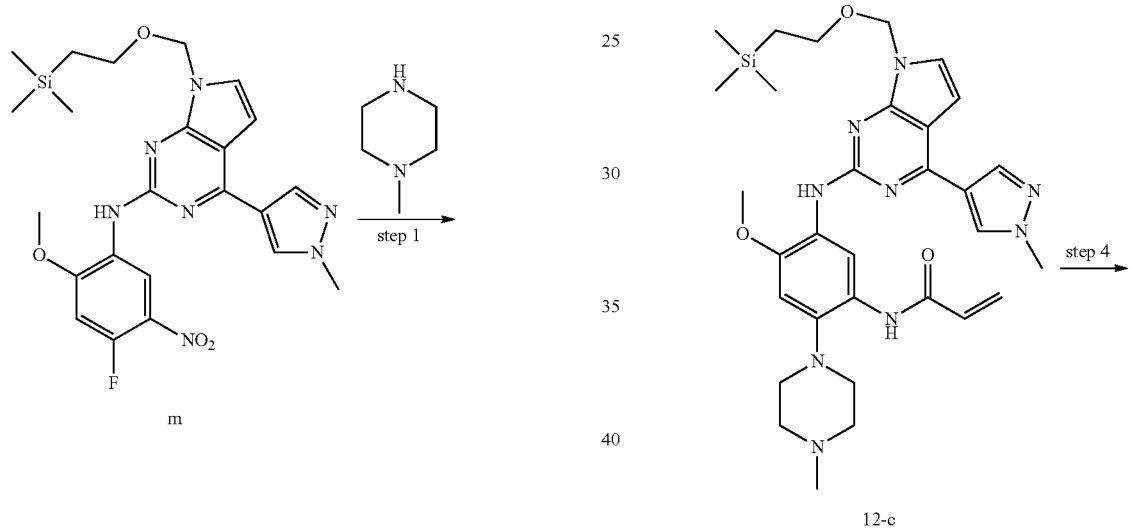

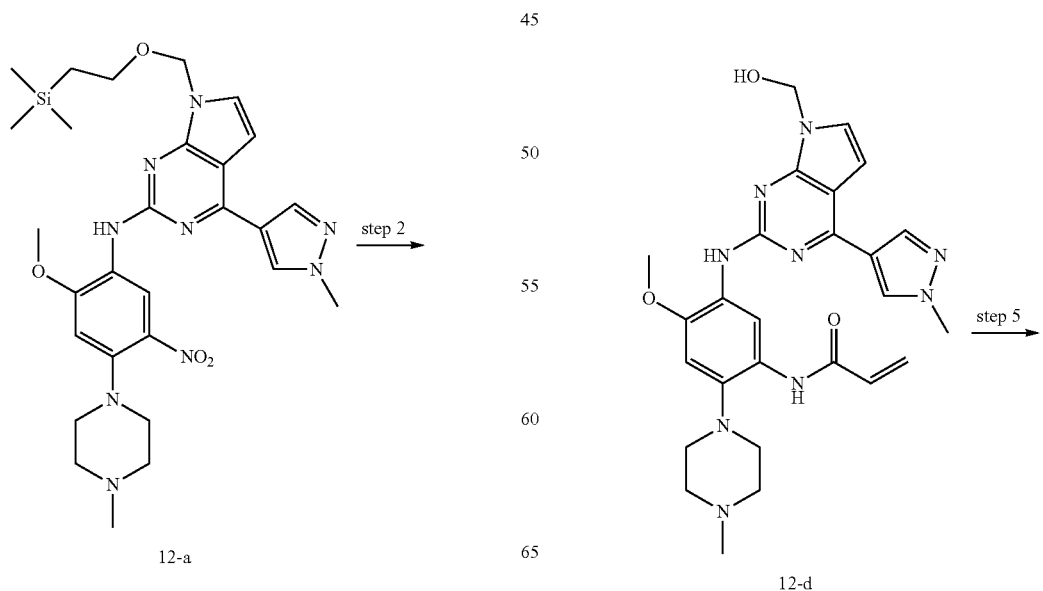

-continued

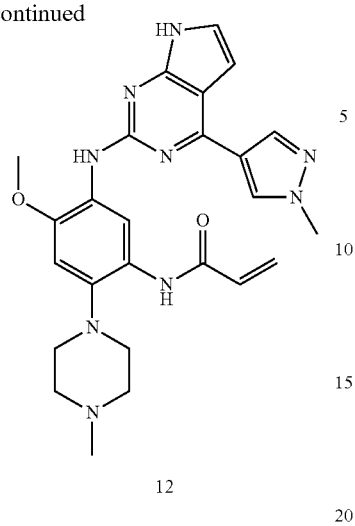

12

The title compound 12 as a yellow solid was prepared from compound m and 1-methylpiperazine according to the method of Example 11. MS m/z(ESI): 488[M+H]+. ¹HNMR (400 MHz, DMSO-d₆) δ 11.46 (s, 1H), 9.13 (s, 1H), 9.06 (s, 1H), 8.89 (s, 1H), 8.34 (s, 1H), 7.46 (s, 1H), 7.22 (dd, J=3.5, 2.3 Hz, 1H), 6.88 (s, 1H), 6.81 (dd, J=3.6, 1.7 Hz, 1H), 6.66 (dd, J=17.0, 10.2 Hz, 1H), 6.31 (d, J=16.9 Hz, 1H), 5.78 (d, J=11.6 Hz, 1H), 3.97 (s, 3H), 3.92 (s, 3H), 2.85 (t, J=4.6 Hz, 4H), 2.52 (s, 4H), 2.26 (s, 3H).

EXAMPLE 13

The Preparation of N-(5-(5-chloro-4-(1-methyl-1H-pyrazol-4-yl)-7H-pyrrolo[2,3-d]pyrimidin-2-ylamino)-2-(4(dimethylamino)piperidin-1-yl)-4-methoxyphenyl)acrylamide (13)

The title compound 13 as a yellow solid was prepared from compound r and compound b according to the method of Example 9. MS m/z(ESI): 550(M+H)+, ¹HNMR(400 MHz, DMSO-d₆) δ 11.81 (s, 1H), 9.06 (s, 1H), 8.89 (S, 1H), 8.64 (s, 1H), 8.19 (s, 1H), 7.64 (s, 1H), 7.38 (d, J=2.1 Hz, 1H), 6.85 (s, 1H), 6.71 (dd, J=16.8, 10.1 Hz, 1H), 6.30 (d, J=17.0 Hz, 1H), 5.78 (d, J=11.5 Hz, 1H), 3.96 (s, 3H), 3.88 (s, 3H), 3.03 (d, J=11.5 Hz, 2H), 2.67 (t, J=11.1 Hz, 2H), 2.31 (s, 1H), 2.29 (s, 6H), 1.86 (d, J=10.6 Hz, 2H), 1.70 (d, J=8.8 Hz, 2H).

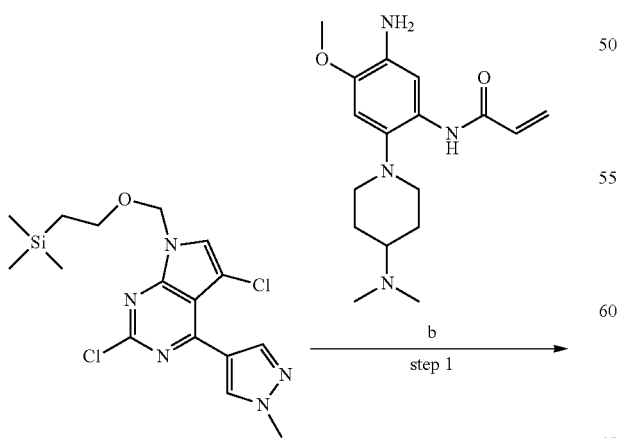

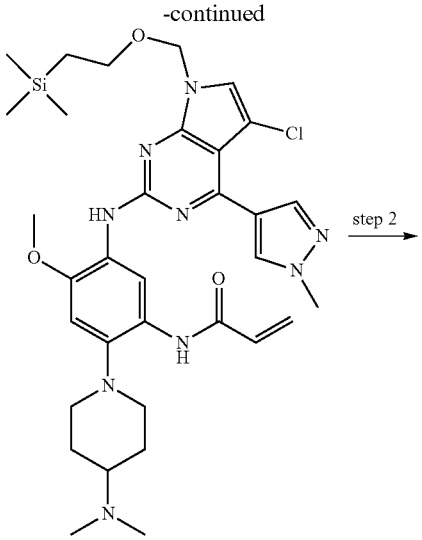

13-a

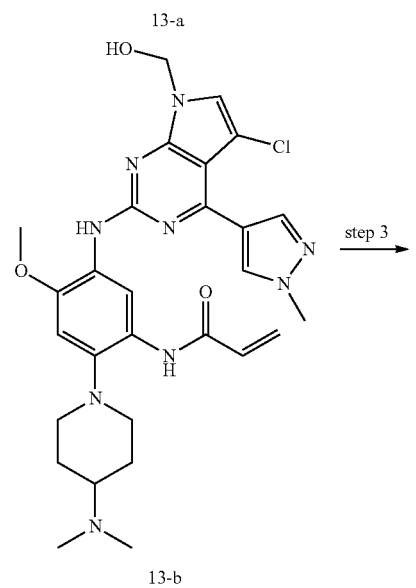

13-b

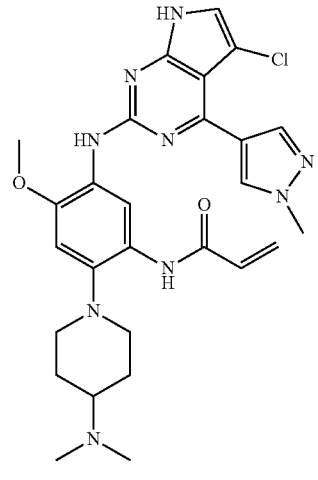

13

EXAMPLE 14

The Preparation of N-(2-(4-(dimethylamino)piperidin-1-yl)-4-methoxy-5-(5-methyl-4-(1-methyl-1H-pyrazol-4-yl)-7H-pyrrolo[2,3-d]pyrimidin-2-ylamino)phenyl)acryl amide (14)

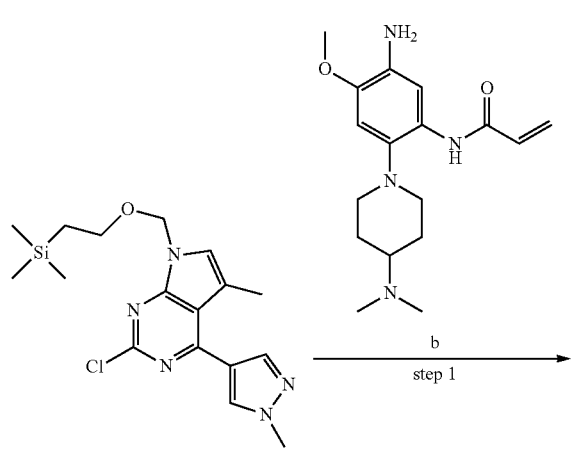

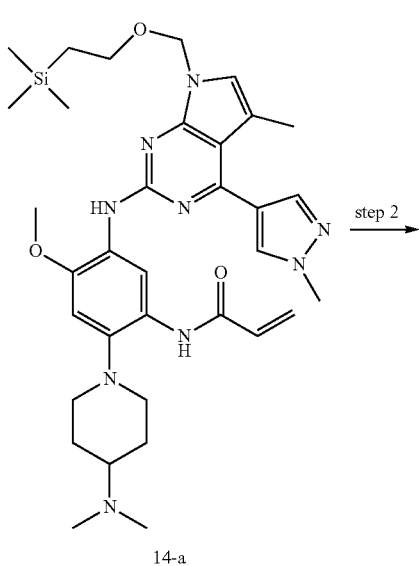

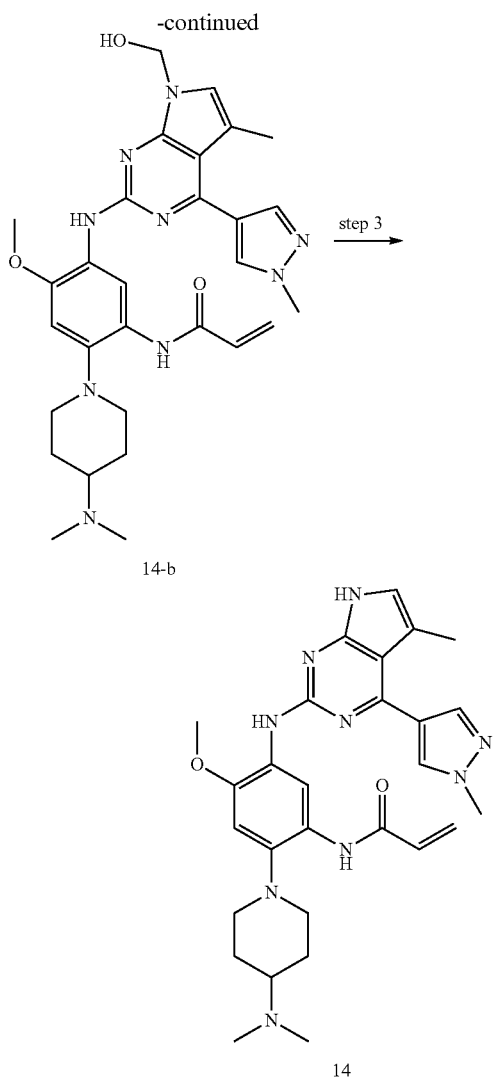

The title compound 14 as a pale yellow solid was prepared from compound p and compound b according to the method of Example 9. MS m/z(ESI): 530.3[M+H]$^+$. $^1$HNMR(400 MHz, DMO-d$_6$) $^1$H NMR (400 MHz, DMSO-d$_6$) δ 11.18 (s, 1H), 9.03 (d, J=3.4 Hz, 2H), 8.52 (s, 1H), 8.01 (s, 1H), 7.43 (s, 1H), 6.95 (s, 1H), 6.84 (s, 1H), 6.70 (dd, 16.9, 10.1 Hz, 1H), 6.30 (d, J=16.9 Hz, 1H), 5.78 (d, J=10.3 Hz, 1H), 3.95 (s, 3H), 3.89 (s, 3H), 3.01 (d, J=11.3 Hz, 2H), 2.66 (t, J=10.9 Hz, 2H), 2.30 (s, 3H), 2.24 (s, 6H), 2.23-2.18 (m, 1H), 1.84 (d, J=11.3 Hz, 2H), 1.68 (d, J=11.2 Hz, 2H).

EXAMPLE 15

The Preparation of N-(2-(4-(dimethylamino)piperidin-1-yl)-4-methoxy-5-(4-(1-methyl-1H-indol-3-yl)-7H-pyrrolo[2,3-D]pyrimidin-2-ylamino)phenyl)acrylamide (15)

The title compound 15 as a yellow solid was prepared from compound h and compound b according to the method of Example 1. MS m/z(ESI); 565[M+H]$^+$. $^1$H NMR (400 MHz, DMSO) δ 11.41 (s, 1H), 9.06 (s, 1H), 8.64 (s, 1H), 8.60 (d, J=7.9 Hz, 1H), 8.42 (s, 1H), 8.23 (s, 1H), 7.65 (s, 1H), 7.51 (d, J=8.1 Hz, 1H), 7.25 (t, J=7.2 Hz, 1H), 7.17 (t, J=6.5 Hz, 2H), 6.85 (dd, J=3.9, 2.1 Hz, 2H), 6.68 (dd, J=16.8, 10.3 Hz, 1H), 6.20 (d, J=16.9 Hz, 1H), 5.72 (d, J=10.5 Hz, 1H), 3.94 (s, 3H), 3.87 (s, 3H), 3.09 (d, J=10.8 Hz, 2H), 2.71 (t, J=11.2 Hz, 2H), 2.62 (s, 1H), 2.46 (s, 6H), 1.94 (d, J=10.5 Hz, 2H), 1.77 (d, J=9.7 Hz, 2H).
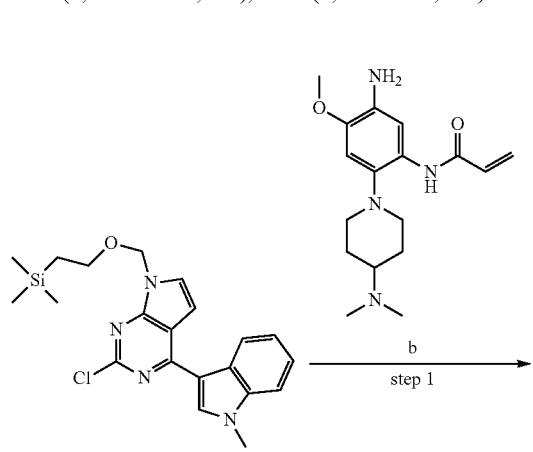
h
step 1
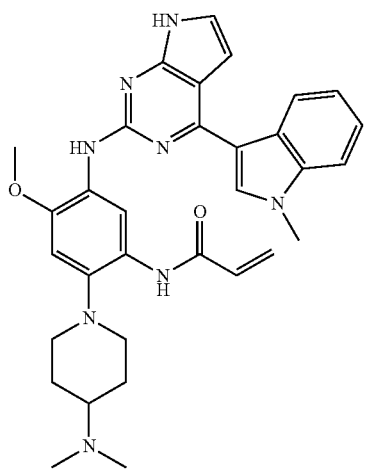
15
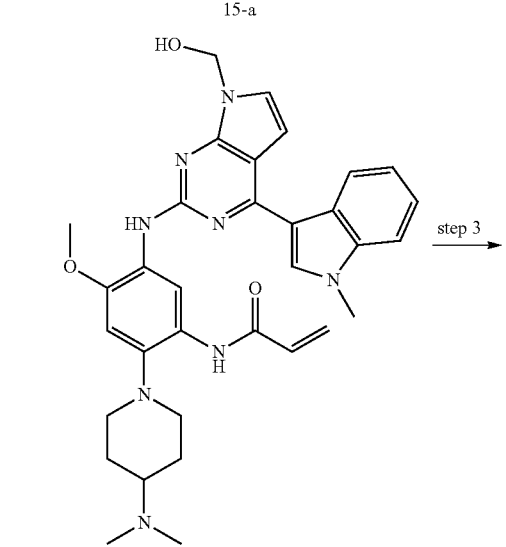
15-a
15-b
EXAMPLE 16
The Preparation of N-(2-((2-(dimethylamino)ethyl)(methyl)amino)-4-methoxy-5-(7-methyl-4-(1-methy-1H-pyrazol-4-yl)-7H-pyrrolo[2,3-d]pyrimidin-2-ylamino)phenyl)acrylamide (16)
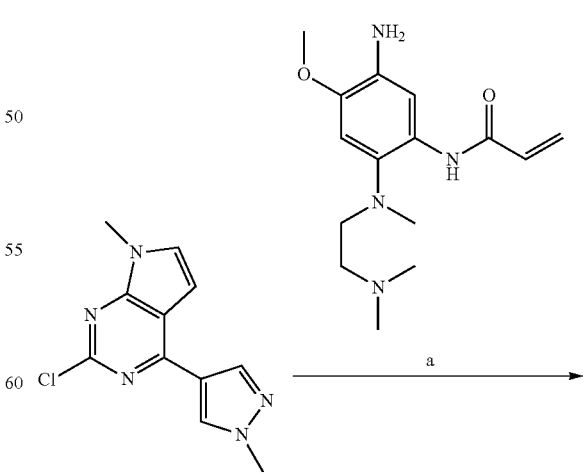
t
a

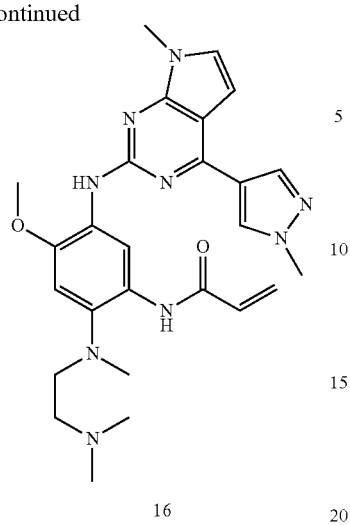

16

The title compound 16 as a pale yellow solid was prepared from compound t and compound a according to step 1 of Example 4. MS m/z(ESI):504[M+H]$^+$. $^1$H NMR (400 MHz, DMSO) δ 10.23 (s, 1H), 9.75 (s, 1H), 8.92 (s, 1H), 8.36 (s, 1H), 7.56 (s, 1H), 7.29 (d, J=4.0 Hz, 1H), 7.04 (s, 1H), 6.85 (d, 3.2 Hz, 1H), 6.42-6.29 (m, 2H), 5.79 (dd, 11.4, 1.6 Hz, 1H), 3.97 (s, 3H), 3.93 (s, 3H), 3.79 (s, 3H), 2.87 (t, 4.2 Hz, 2H), 2.70 (s, 2H), 2.26 (t, J=4.2 Hz, 2H), 2.20 (s, 6H).

EXAMPLE 17

The Preparation of N-(2-(4-(dimethylamino)piperidin-1-yl)-4-methoxy-5-(4-(1-(methylsulfonyl)azetidin-3-yloxy)-7H-pyrrolo[2,3-D]pyrimidin-2-ylamino)phenyl)acrylamide (17)

The title compound 17 as a yellow solid was prepared from compound u and compound b according to the method of Example 9. MS m/z(ESI): 585[M+H]$^+$. $^1$H NMR (400 MHz, CD$_3$OD) δ 9.18 (s, 1H), 6.97 (d, 1H, J=3.2), 6.89 (s, 1H), 6.59 (dd, J=17.6, 9.6 Hz, 1H), 6.44 (d, J=16.8, 1H), 6.41 (d, J=4.0, 1H), 5.82 (d, 10.4 Hz, 1H), 5.82-5.79 (m, 1H), 4.40-4.34 (m, 2H), 4.10-4.05 (m, 2H), 3.93 (s, 3H), 3.22-3.15 (m, 2H), 2.98 (s, 3H), 2.93 (s, 6H), 2.87-2.82 (m, 2H), 2.20-2.13 (m, 2H), 2.06-1.91 (m, 2H).

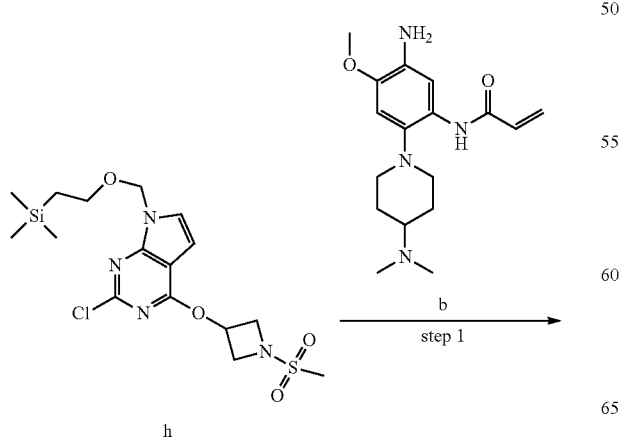

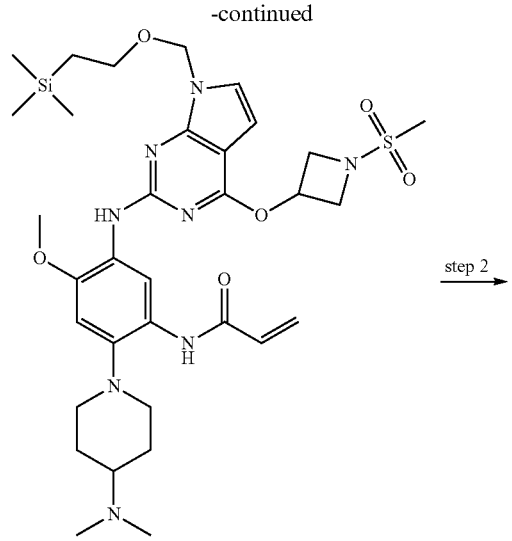

17-a

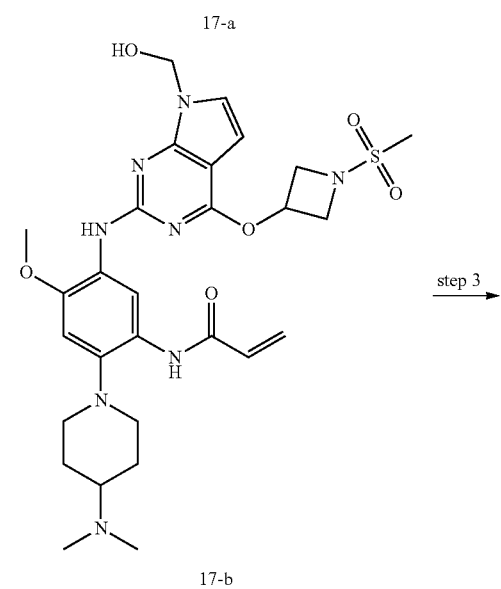

17-b

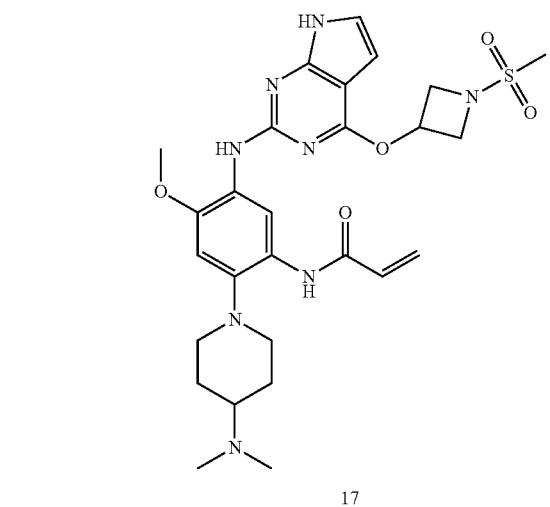 [SMILES: C=CC(=O)Nc1cc(Nc2nc(OC3CN(S(C)(=O)=O)C3)c3cc[nH]c3n2)c(OC)cc1N1CCC(N(C)C)CC1]

17

EXAMPLE 18

The Preparation of N-(4-methoxy-2-(4-methylpiperazin-1-yl)-5-(4-(1-(methylsulfonyl)azetidin-3-yloxy)-7H-pyrrolo[2,3-d]pyrimidin-2-ylamino)phenyl)acrylamide (18)

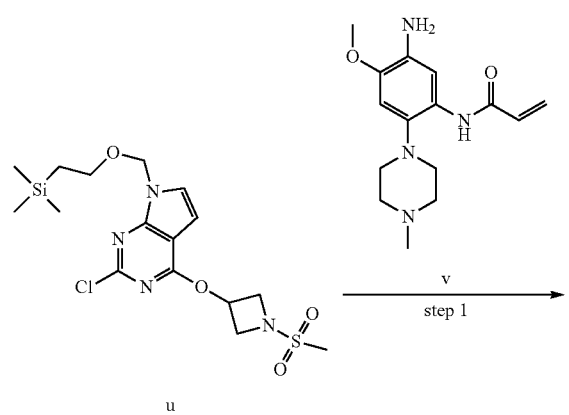

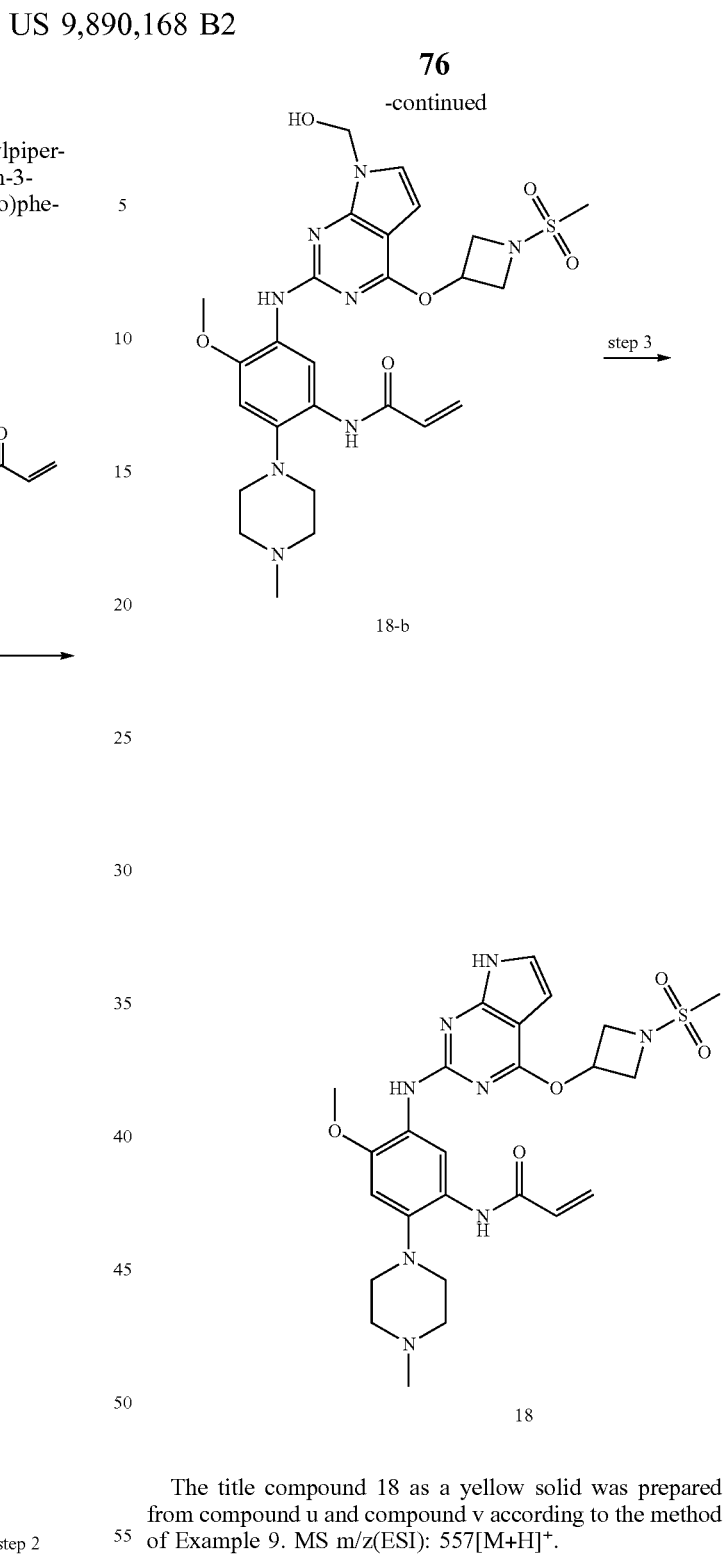

The title compound 18 as a yellow solid was prepared from compound u and compound v according to the method of Example 9. MS m/z(ESI): 557[M+H]$^+$.

EXAMPLE 19-34

Compounds 19-34 have the structure of formula (I), wherein the substituents A, X, $R_0$, $R_1$, $R_2$, and $R_3$ are defined as shown in the following table. Compounds 19-34 were prepared by the similar methods for compounds 1-18 according to the different structures listed in the following table. All starting materials and intermediates used can be prepared by those skilled in the art according to the existing methods.

| Compound No. | A ring | R₃ | R₀ | R₁ | R₂ | X | MS [M + H]⁺ |
|---|---|---|---|---|---|---|---|
| 19 | 5-(1-methyl-7-azaindol-5-yl) | 4-(dimethylamino)piperidin-1-yl | H | H | CH₃ | Covalent bond | 580 |
| 20 | 5-(1-methyl-7-azaindazol-5-yl) | N-methyl-N-(2-(dimethylamino)ethyl) | CH₃ | H | H | Covalent bond | 554 |
| 21 | 5-(1-methyl-7-azaindazol-5-yl) | N-methyl-N-(2-(dimethylamino)ethyl) | CH₃ | H | CH₃ | Covalent bond | 568 |
| 22 | 5-(1-methyl-7-azaindol-5-yl) | 4-methylpiperazin-1-yl | H | H | Cl | Covalent bond | 572 |
| 23 | 5-(1,3-dimethyl-7-azaindol-5-yl) | N-methyl-N-(2-(dimethylamino)ethyl) | H | H | H | Covalent bond | 554 |
| 24 | morpholin-4-yl | 4-(dimethylamino)piperidin-1-yl | H | H | CH₃ | Covalent bond | 535 |
| 25 | phenyl | 4-(dimethylamino)piperidin-1-yl | H | H | CH₃ | Covalent bond | 526 |
| 26 | pyridin-3-yl | 4-methylpiperazin-1-yl | CH₃ | H | H | Covalent bond | 498 |
| 27 | 3-methyl-1-methylpyrazol-4-yl | N-methyl-N-(2-(dimethylamino)ethyl) | CH₃ | H | H | Covalent bond | 518 |
| 28 | 1-methylpyrazol-4-yl | N-methyl-N-(2-(dimethylamino)ethyl) | CH₃ | H | Cl | Covalent bond | 538 |

-continued
| Compound No. | A ring | $R_3$ | $R_0$ | $R_1$ | $R_2$ | X | MS $[M + H]^+$ |
|---|---|---|---|---|---|---|---|
| 29 |  | 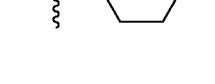 | $CH_3$ | H | H | Covalent bond | 544 |
| 30 |  | 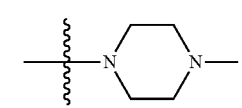 [SMILES: *N1CCN(C)CC1] | H | H | Cl | Covalent bond | 536 |
| 31 |  | 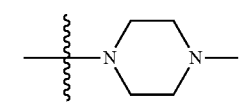 [SMILES: *N1CCN(C)CC1] | $CH_3$ | H | H | Covalent bond | 502 |
| 32 |  | 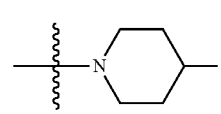 | $CH_3$ | H | H | O | 599 |
| 33 |  | 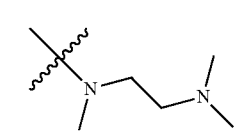 [SMILES: *N(C)CCN(C)C] | H | H | $CH_3$ | O | 573 |
| 34 |  | 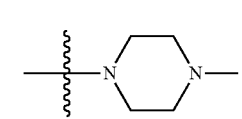 | H | H | Cl | O | 591 |
COMPARATIVE EXAMPLE
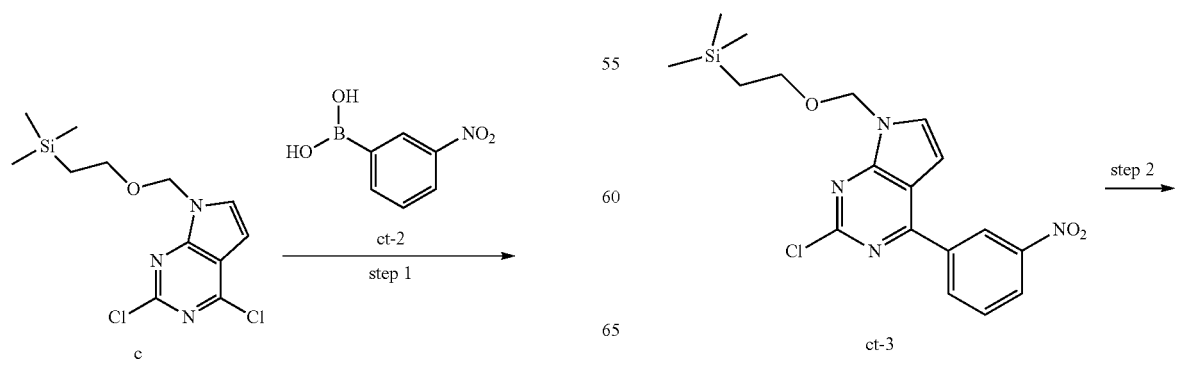

81
-continued

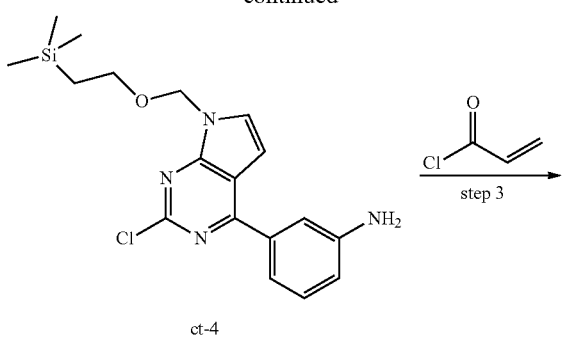
ct-4

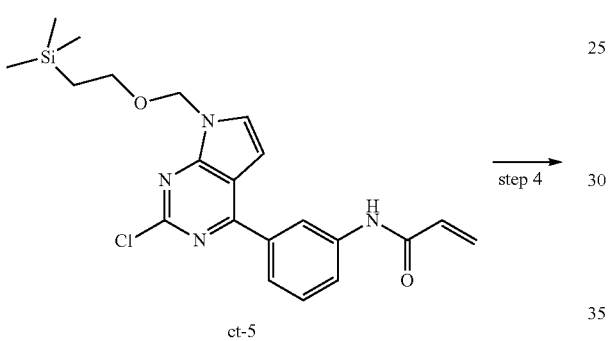
ct-5

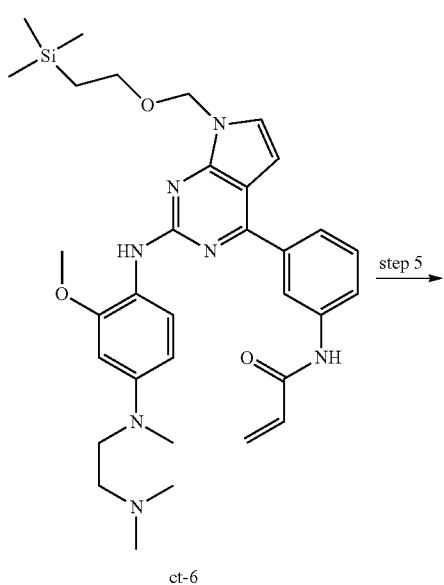
ct-6

82
-continued

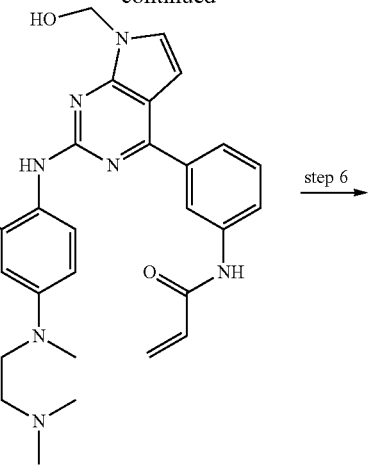
ct-7

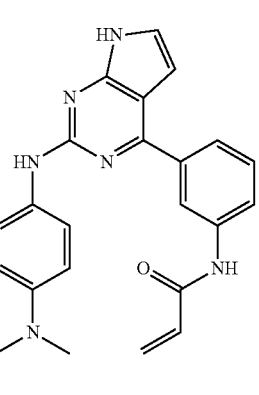
Comparative compound 1 step 1: Compound ct-3 was prepared from compound c and compound ct-2 according to the preparation method of compound i. Yield: 65%. MS m/z(ESI): 405 [M+H]$^+$.

step 2-3: Compound ct-5 was prepared from compound ct-3 according to step 3 and step 4 in the preparation of compound a. Yield: 55%. MS m/z(ESI): 429 [M+H]$^+$.

step 4: Compound ct-6 was prepared from compound ct-5 and compound w according to step 1 in Example 1. Yield: 11.7%. MS m/z(ESI): 616 [M+H]$^+$.

step 5-6: Comparative compound I was prepared from compound ct-6 according to the method of Example 3. Yield 11%. MS m/z(ESI):486[M+H]$^+$.

TEST EXAMPLE 1

Assay of Inhibition Activity on Wild Type EGFR and Mutant EGFR Kinase

All reagents used in the following z'-lyte assay were purchased from Invitrogen.

The inhibitory activities on T790M/L858R double mutant EGFR kinase (Invitrogen, PV4879) and wild-type EGFR kinase (Invitrogen, PV3872) were determined by the z'-lyte assay.

The working concentrations of each component in 10 μL T790M/L858R kinase reaction system were: 25 μM ATP, 0.1 ng/μL T790M/L858R kinase, 2 μM Tyr04 substrate (Invitrogen, PV3193). The concentration of DMSO after addition of the compound prepared in the above examples of the present invention (i.e., the compound to be tested) was 2 vol %.

The working concentrations of each component in 10 μL wild-type EGER kinase reaction system were: 10 μM ATP, 0.8 ng/μL wild-type EGFR kinase, 2 μM Tyr04 substrate (Invitrogen, PV3193). The concentration of DMSO after addition of the compound to be tested was 2 vol %.

10 mM drug stock solution was dissolved at room temperature and diluted to a final concentration of 4-0.002 μM with 8 vol % DMSO solution. 2.5 μL of the solution of the compound to be tested and 5 μL of the mixture of T790M/L858R kinase (or wild-type EGFR kinase) and Tyr04 substrate diluted with the reaction buffer were added to each well. Then 2.5 μl of ATP was added to initiate the reaction. Wherein, ATP was replaced by the reaction buffer in C1 well, no drug was added to C2 well, and the phosphorylated substrate was added to C3 well according to the instructions. The mixture was allowed to react at 25° C. in a shaker in dark for 60 min, 5 μL of Development Reagent B (invitrogen, diluted with TR-FRET dilution buffer) was added and allowed to react at room temperature in the shaker for 60 minutes. The plate was read on a Victor X5 plate reader (PerkinElmer) and the absorbance was measured at excitation wavelengths of 405 nm and emission wavelengths of 450 nm and 520 nm (for example, $C3_{520}$ nm indicates the absorbance for C3 well at 520 nm).

The inhibition rate was calculated according to the following method (refer to the instructions of Invitronen, PV3193):

1. ER=Coumarin Emission (450 nm)/Fluorescein Emission (520 mn)
2. Phosphorylation ratio=$(1-((ER \times C3_{520\ nm}-C3_{450\ nm})/((C1_{450\ nm}-C3_{450\ nm})+ER \times (C3_{520\ nm}-C1_{520\ nm})))) \times 100\%$
3. Inhibition ratio (IR)=(1-(phospholylation ratio of the test compound)/(phosphorylation ratio of C2))×100%

The half-inhibitory concentration $IC_{50}$ was obtained through fitting calculation by using XLFIT 5.0 software (IDBS, UK).

TABLE 1

Enzyme inhibitory activity and selective inhibitory activity

| Compound No. | T790M/L858R ($IC_{50}/\mu M$) | EGFR WT ($IC_{50}/\mu M$) | Selective inhibitory activity against enzymes [$IC_{50}$ (EGFR WT)/$IC_{50}$ (T790M/L858R)] |
|---|---|---|---|
| 1 | 0.010 | 0.393 | 39.3 |
| 2 | 0.045 | >1 | >22.2 |
| 3 | 0.005 | 0.088 | 17.6 |
| 4 | 0.001 | 0.039 | 39 |
| 5 | 0.003 | 0.015 | 5 |
| 6 | 0.013 | 0.347 | 27 |
| 7 | 0.020 | 0.315 | 16 |
| 9 | 0.022 | >1 | >45.5 |
| 10 | 0.024 | 0.578 | 24.1 |
| 11 | 0.197 | >1 | >5.1 |
| 12 | 0.098 | >1 | >10.2 |
| 13 | 0.051 | >1 | >19.6 |
| 14 | 0.110 | >1 | >9.1 |
| AZD-9291 | 0.002 | 0.003 | 1.5 |
| BIBW2992 | 0.005 | 0.001 | 0.2 |
| Comparative compound 1 | 1.002 | >10 | >10 |

It can be seen from table 1 that compounds 1-14 in the examples of the present invention exhibit a strong inhibitory activity against the EGFR mutant enzyme (T790M/L858R) but a weak inhibitory activity against EGFR wild-type enzyme (T790M WT) compared with the positive control BIBW2992 (alfatinib) and AZD-9291 (the preparation method thereof is referred to WO2013014448A1, and the structure is as follows). Moreover, it can be been found from this study that the compounds obtained by changing the substitution position of the acrylamide group have little activity. Therefore, the compounds of the present invention have good selective inhibitory activity against EGFR mutant enzymes.

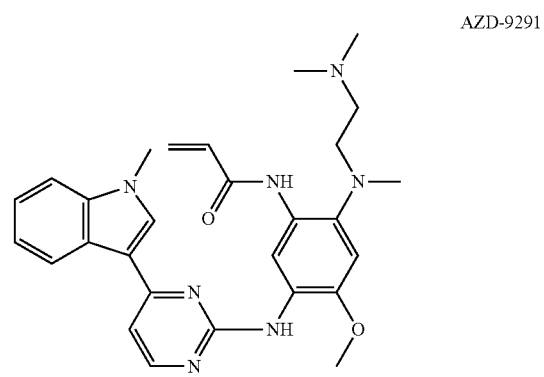 [SMILES: C=CC(=O)Nc1cc(Nc2nccc(-c3cn(C)c4ccccc34)n2)c(OC)cc1N(C)CCN(C)C]

AZD-9291

TEST EXAMPLE 2

Inhibition of EGFR Phosphorylation in A431 (EGFR Wild-Type) and H1975 (EGFR T790M Mutant) Cells by EGFR T790M Inhibitor (Determined by ELISA)

The reagents used in the following methods, the preparation methods of solutions, the cell treatment and the preparation steps of lysate were carried out according to the instructions of R&D DYC3570, R&D DYC1095E and R&D DYC1095BE.

I. Reagents and Solutions

Cell lysis buffer: 1%(WSV) NP-40, 20 mM Tris (pH 8.0), 137 mM NaCl, 10%(V/V) glycerol, 1 mM $NaVO_2$, 2 mM EDTA.

Cell lysis solution: Cell lysis buffer+10 μg/mL Aprotinin (Sigma)+10 μg/mL Leupeptin (Sigma), prepared on site.

1× PBS buffer: NaCl: 0.137M, KCl: 0.0027M, $Na_2PO_4$-$12H_2O$: 0.01M, $KH_2PO_4$: 0.0015M, pH 7.4.

Wash buffer: PBS buffer containing 0.05% (v/v) Tween-20.

Detection antibody diluent: 20 mM Tris, 137 mM NaCl, 0.05% (v/v) Tween-20, 0.1% (w/v) BSA, pH 7.2-7.4.

Blocking solution: PBS buffer containing 1% (w/v) BSA.

ELISA kits: R&D DYC3570, R&D DYC1095E and R&D DYC1095BE.

II. H1975 Cells 2.1 H1975 cell treatment and lysis solution preparation (1) H1975 cells (purchased from the Cell Bank of the Type Culture Collection Committee, Chinese Academy of Sciences) were seeded into 96-well plates at a density of 1×10⁴/well, and 90 μl of RPMI medium containing 10% (V/V) FBS was contained in each well and cultured overnight at 37° C. in 5% (v/v) $CO_2$.

(2) The compounds to be tested were diluted in accordance with the drug dilution method in the MTT assay. 10

µL of the diluted compound solution or diluted DMSO was added to the corresponding wells of the cell culture plate, and the final concentration of DMSO was 0.5% (V/V). The plate was cultured at 37° C. in 5% (v/v) $CO_2$ for 1 h. The cell culture system treated with DMSO alone was used as cell control.

(3) The medium was removed and then 100 µL of cell lysis solution was added. The plate was sealed and placed in a refrigerator at −80° C. overnight. The cell lysis buffer was used as blank control.

2.2 ELISA Assay Steps

The assay was conducted according to the instructions given in R&D DYC1095E or R&D DYC1095BE.

(1) R&D capture antibody ((DYC1095BE or DYC1095E)) was diluted with PBS in the proportion of 1:180. 100 µL of the diluted antibody was added to each well of the ELISA plate (Corning costar 42592) and the coated plate was incubated at 25° C. with shaking overnight.

(2) The plate wad washed 3 times with 360 µL of the wash buffer.

(3) 300 µL of the blocking solution was added and the plate was incubated at 25° C. with shaking for 2 hours.

(4) The plate wad washed 3 times with 360 µL of the wash buffer.

(5) 40 µL of cell lysis buffer and 60 µL of cell lysis solution were added and the plate was incubated at 25° C. with shaking for 2 hours.

(6) The plate wad washed 3 times with 360 µL of the wash buffer.

(7) The detection antibody was diluted with the detection antibody diluent in the proportion specified in the instructions of the kit. 100 µL of the diluent antibody was added to each well and the plate was incubated at 25° C. with shaking in dark for 1 h.

(8) The plate wad washed 3 times with 360 µL of wash buffer.

(9) A reagent and B reagent in the TMB substrate (R&D DY999) were mixed in 1:1. 100 µL of the mixture was added to each well and incubated in dark at 25° C. with shaking for 20 min.

(10) 50 µL, of 2N $H_2SO_4$ was added to each well.

(11) The plate was read with a microplate reader (Thermo Multiskan K3). OD 450 values and OD570 values of the cell control, blank control, and drug treatment wells were measured. $OD_{cell}$, $OD_{blank}$ and $OD_{drug\ treatment}$ were obtained by subtracting the corresponding OD570 value from the OD 450 value of the same well.

2.3 Data Analysis

Inhibition rate (%)=100%×($OD_{cell}$−$OD_{drug\ treatment}$)/($OD_{cell}$−$OD_{blank}$)

2.4 $ID_{50}$ values were calculated using the XLFIT 5.0 software based on the calculated inhibition rate and the results were shown in table 4.

III. A431 Cells 3.1 A431 Cell Treatment and Testing Procedures (1) A431 cells (purchased from the Cell Bank of the Type Culture Collection Committee, Chinese Academy of Sciences) were seeded in 96-well plates at a density of 1×10⁴/well in 90 µl DMEM medium containing 10% FBS and cultured at 37° C. in 5% $CO_2$ overnight.

(2) The A431 cell culture medium was replaced with 90 µl of serum-free DMEM medium and the plate was cultured overnight.

(3) The compound to be tested was diluted according to the drug dilution method in MTT assay. 10 µL of the dilated compound solution or diluted DMSO was added to the corresponding wells of the cell culture plate, and the final concentration of DMSO was 0.5%. The plate was cultured at 37° C. in 5% $CO_2$ for 1 hour. 10 µl of 2 µg/L EGF(R&D, 236-EG-01M) was added to each well except the cell control well and 10 µl of serum-free DMEM was added to the cell well and incubated for 45 minutes. The cells without EGF and drugs were used as cell control, and the cells treated with EGF without drugs were used as EGF control.

(4) The medium was removed and then 100 µL, of the cell lysis solution was added. The plate was sealed and placed in a refrigerator at −80° C. overnight.

3.2 ELISA Assay Steps

The assay was conducted according to the instructions given in R&D DYC3570E.

(1) R&D capture antibody (DYC3570E) was diluted with PBS in the proportion of 1:180. 100 µL, of the diluted antibody was added to each well of the ELISA plate (Corning costar 42592) and the coated plate was incubated at 25° C. with shaking overnight.

(2) The plate was washed 3 times with 360 µL of the wash buffer.

(3) 200 µL of the blocking solution was added and the plate was incubated at 25° C. with shaking for 2 hours.

(4) The plate was washed 3 times with 360 µL of wash buffers (5) 40 µL of cell lysis butler and 60 µL of cell lysis solution were added and the plate was incubated at 25° C. with shaking for 2 hours.

(6) The plate wad washed 3 times with 360 µL of the wash buffer.

(7) The detection antibody was diluted with the detection antibody diluent in the proportion specified in the instructions of the kit. 100 µL of the diluent antibody was added to each well and the plate was incubated at 25° C. with shaking in dark for 1 h.

(8) The plate wad washed 3 times with 360 µL of the wash butler.

(9) A reagent and B reagent in TMB substrate (R&D DY999) were mixed in 1:1. 100 µL mixture was added to each well and incubated in dark at 25° C. with shaking tor 20 min.

(10) 50 µL of 2N $H_2SO_4$ was added to each well.

(11) The plate was read with a microplate reader (Thermo Multiskan K3). OD 450 values and OD570 values of the cell control, blank control, and drug treatment wells were measured. $OD_{EGF}$, $OD_{drug}$ and $OD_{cell}$ were obtained by subtracting the corresponding OD570 value from the OD 450 value of the same well.

3.3 Data Analysis

Inhibition rate (%)=100%×($OD_{EGF}$−$OD_{drug}$)/($OD_{EGF}$−$OD_{cell}$)

3.4 $IC_{50}$ Values were Calculated Using the XLFIT 5.0 Software Based on the Calculated to Inhibition Rate and the Results were Shown in Table 2.

TABLE 2

| | Results of the cell activity by ELISA assay | | |
|---|---|---|---|
| Compound No. | H1975 cell ($IC_{50}$/µM) | A431 cell ($IC_{50}$/µM) | Selective inhibitory activity against targets at the cell level [$IC_{50}$ (A431 cell)/ $IC_{50}$ (H1975 cell)] |
| 1 | 0.112 | 3.667 | 32.7 |
| 2 | 0.322 | >10 | 31 |
| 3 | 0.032 | 0.860 | 26.9 |

TABLE 2-continued

Results of the cell activity by ELISA assay

| Compound No. | H1975 cell (IC$_{50}$/μM) | A431 cell (IC$_{50}$/μM) | Selective inhibitory activity against targets at the cell level [IC$_{50}$ (A431 cell)/ IC$_{50}$ (H1975 cell)] |
|---|---|---|---|
| 4 | 0.015 | 0.254 | 17 |
| 5 | 0.016 | 0.119 | 7.4 |
| 6 | 0.096 | 1.674 | 17.4 |
| 7 | 0.204 | 1.874 | 9.2 |
| 9 | 0.384 | >10 | >26 |
| 10 | 0.166 | 8.982 | 54.1 |
| 13 | 0.329 | >10 | 30.4 |
| BIBW2992 | 0.021 | 0.005 | 0.24 |

As can be seen from Table 2, the compounds of the examples of the present invention have a better selective inhibitory activity against EGFR mutant cells than that of the positive control BIBW2992.

TEST EXAMPLE 3

Cell Inhibitory Activity Tested by MTT (3-(4,5-dimethylthiazole-2)-2,5-diphenyltetrazolium bromide) Assay The steps of the MTT assay are carried out using methods well known to those skilled in the art, and all the reagents used in the methods are commercially available.

Firstly, the medium was removed and 1 mL of 0.25% trypsin/EDTA was added (Gibco, 25200-056). After the first wash, 1.5 mL of trypsin/EDTA was added to digest the adherent cells until the cells detached. Then 3.5 mL of the culture medium was added to terminate the digestion. The digested cell suspension was transferred to a 15 mL centrifuge tube and centrifuged at 1300 rpm for 3 minutes. The supernatant was discarded and the cells were resuspended in fresh medium. The cells were then counted and diluted to the following concentrations: 27,800 cells per milliliter of H1975 cells, 33,300 cells per milliliter of A431 cells and NIH3T3 cells. Cells were seeded in 96 well plates (BD 3072), 90 μL/well, and cultured overnight.

A431 cell culture medium: DMEM (Hyclone SH30243.01B) containing 10% FBS (Gibeco, 10099-141);

NIH3T3 cell culture medium: DMEM alyclone SH30243.01B) containing 10% FBS (Gibco, 10099-141);

H1975 cell culture medium: RPMI-1640 (Hyclone SH30809.01B) containing 10% FBS (Gibco, 10099-141);

20 μL of 10 mM compound to be tested (200×) was diluted with the following concentration gradients (2000, 666.67, 222.22, 74.07, 24.69, 8.23, 2.74, 0.91 μM), followed by adding serum-free medium (final concentrations: 100, 33.33, 11.11, 3.404, 1.235, 0.412, 0.137, 0.046 μM), and 10 μl of drug was added to each well of the cell culture plate with a final DMSO concentration of 0.5%.

After the drug was added, the cells were incubated in an incubator for 72 hours. 10 μL of 5 mg/ml MTT (Sigma, M5655) solution was added to each well. The 96-well plate was then incubated in a 37° C. and 5% CO2 incubator for 4 h.

The plate was then centrifuged at 2000 rpm for 5 min. After the supernatant was removed, 150 μl of DMSO was added to each well and the plate was shaken in a shaker until all crystal violet was dissolved. Finally, absorbance at 492 nm was measured using a microplate reader and IC$_{50}$ was calculated using the XLFIT 5.0 software (IDBS, UK).

TABLE 3

Inhibitory activity and selectivity of the compounds on cell growth

| Compound No. | H1975 cell (IC$_{50}$/μM) | A431 cell (IC$_{50}$/μM) | Selective inhibitory activity against cell growth [IC$_{50}$ (A431 cell)/ IC$_{50}$ (H1975 cell)] |
|---|---|---|---|
| 1 | 0.043 | 1.561 | 36.3 |
| 2 | 0.143 | 4.006 | 28 |
| 3 | 0.029 | 2.930 | 101 |
| 4 | 0.029 | 1.122 | 38.7 |
| 5 | 0.009 | 0.308 | 34.2 |
| 6 | 0.079 | 1.801 | 22.8 |
| 7 | 0.225 | 1.688 | 7.5 |
| 9 | 0.300 | 4.342 | 14.5 |
| 10 | 0.112 | 3.799 | 34 |
| 13 | 0.531 | 3.036 | 5.7 |
| BIBW2992 | 0.088 | 0.029 | 0.33 |

As can be seen from Table 3, compared to the positive control BIBW2992, the example compounds of the present invention showed a stronger inhibitory activity against EGFR mutant type cells (H1975 cells), but showed a weak inhibition to EGFR wild type cells (A431 cells). The compounds of the present invention thus have a good selective inhibitory activity against EGFR mutant cells.

TABLE 4

Results of the toxicity test of the compounds on NIH3T3 cells

| Compound No. | MTT assay for NIH3T3 cells (IC$_{50}$/μM) |
|---|---|
| 1 | >10 |
| 2 | >10 |
| 3 | >10 |
| 4 | 2.094 |
| 5 | 2.632 |
| 6 | 5.101 |
| 7 | 2.423 |
| 9 | >10 |
| 10 | >10 |
| 13 | >10 |
| BIBW2992 | 2.750 |

As can be seen from Table 4, the example compounds of the present invention have higher IC$_{50}$ values for NIH3T3 cells, and thus exhibit less toxicity compared to the positive control BIBW2992.

The results of the asssays of in vitro kinase activity inhibition, intracellular EGFR phosphorylation level inhibition and cell arowth inhibition demonstrate that the example compounds of the present invention exhibit a stronger inhibitory activity against mutant EGFR enzyme activity, EGFR phosphotylation level, and cell proliferadon but show a weak inhibition on wild-type EGFR enzyme activity, EGFR phosphorylation level, and cell proliferation. Therefore, the compounds of the present invention have excellent selectivity for EGFR mutant cells. The results of cytotoxicity test show that the compounds of the present invention have a minimal inhibitory effect on NIH-3T3 cells thereby showing low cytotoxicity. Therefore, these compounds have excellent selective inhibitory activity and low cytotoxicity on T790M mutant EGFR.

At the same time, the compounds of the present invention exhibit good bioavailability.

All literatures mentioned in the present appliCation are incorporated by: reference herein, as though each individually incorporated by reference. Additionally, it should be understood that after reading the above teachings, many variations and modifications may be made by the skilled in the art, and these equivalents also fall within the scope as defined by the appended claims.

The invention claimed is:

1. A compound of formula (I), or a pharmaceutically acceptable salt, solvate, or stereoisomer thereof:

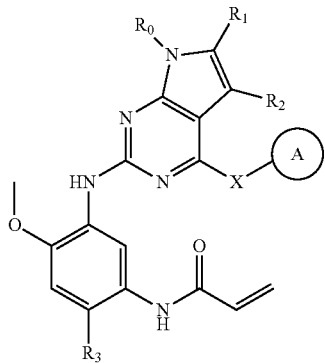

wherein, ring A is a substituted or unsubstituted $C_{3-10}$ heterocyclic ring, substituted or unsubstituted $C_{6-10}$ aryl ring or substituted or unsubstituted $C_{4-10}$ cycloalkenyl ring;

when substituted, 1-6 hydrogen atoms of the heterocyclic, aryl or cycloalkenyl ring are substituted with a substituent selected from the group consisting of hydroxy, CN, $NO_2$, halogen, $C_{1-3}$ alkyl, $C_{1-3}$ haloalkyl, —CON$(C_{1-3}$ alkyl$)_2$, —C(O)O$C_{1-3}$ alkyl, —OC(O)$C_{1-3}$ alkyl, —CO$C_{1-3}$ alkyl, —CO-phenyl, —$SO_2C_{1-3}$ alkyl, —$SO_2$-phenyl, —S(O)$C_{1-3}$ alkyl, —S(O)-phenyl, and —N($C_{1-3}$ alkyl$)_2$;

X is a covalent bond, or NH, O or S;

$R_0$ is H, $C_{1-3}$ alkyl, $C_{1-3}$ haloalkyl, $C_{3-6}$ cycloalkyl, $C_{3-6}$ halocycloalkyl, —CHO, —CO$C_{1-3}$ alkyl, —CO-phenyl, —$SO_2C_{1-3}$ alkyl, or —$SO_2$-phenyl;

$R_1$ and $R_2$ are each independently H, halogen, $C_{1-3}$ alkyl, or $C_{1-3}$ haloalkyl; and $R_3$ is selected from the group consisting of:

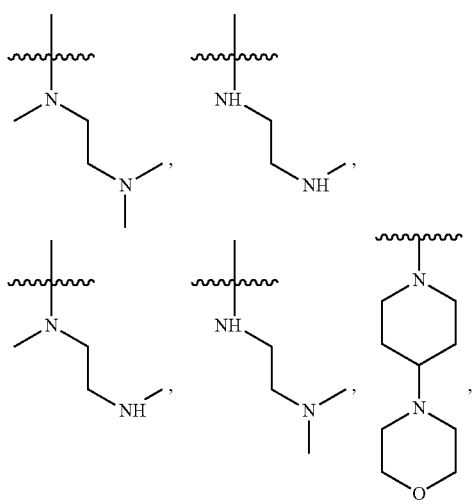

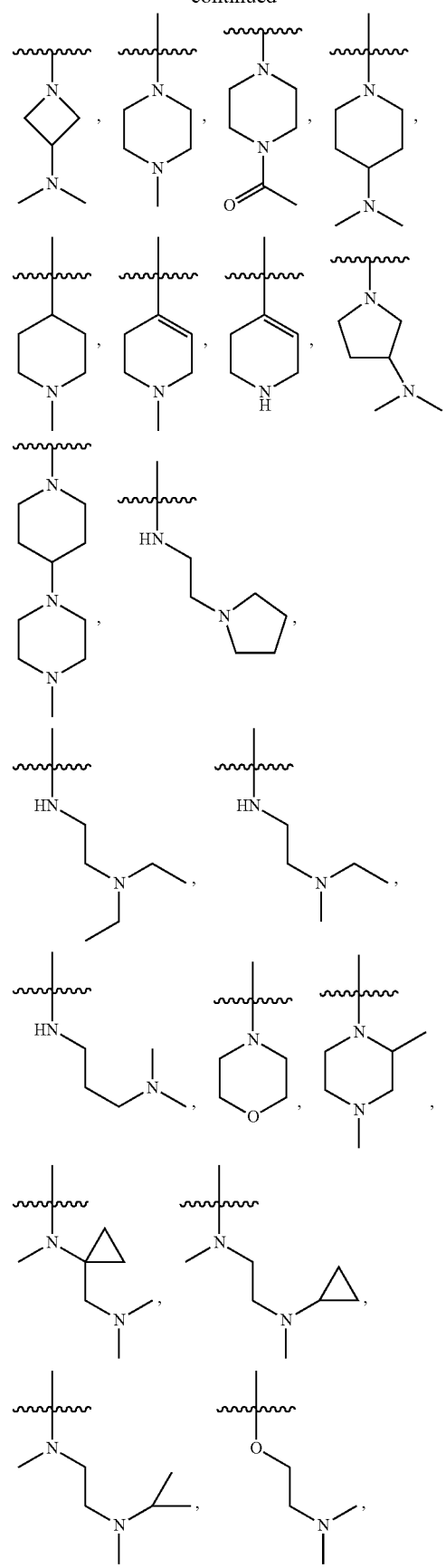

-continued

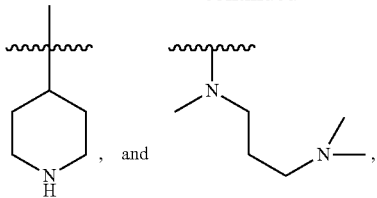

wherein phenyl is unsubstituted or substituted with 1 to 3 substituents selected from the group consisting of halogen and $C_{1-3}$ alkyl.

2. The compound, or the pharmaceutically acceptable salt, solvate, or stereoisomer thereof of claim 1, wherein $R_3$ is selected from the group consisting of:

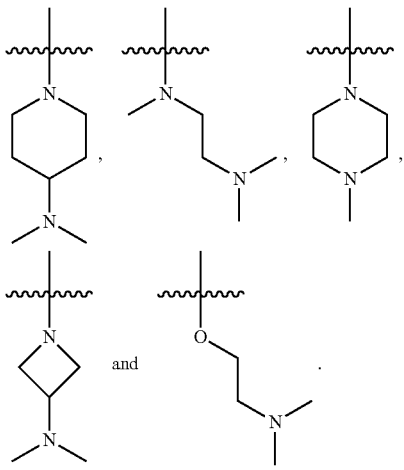

3. The compound, or the pharmaceutically acceptable salt, solvate, or stereoisomer thereof of claim 1, wherein $R_0$ is H, methyl, ethyl, propyl, isopropyl, cyclopropyl, cyclobutyl, cyclopentyl, cyclohexyl, monofluoroethyl, difluoromethyl, trifluoromethyl, —$COCH_3$, —CO-phenyl, —$SO_2CH_3$ or —$SO_2$-phenyl; wherein phenyl is unsubstituted or substituted with 1 to 3 substituents selected from the group consisting of: fluorine, chlorine, bromine, methyl, and ethyl; and $R_1$ and $R_2$ are each independently H, fluorine, chlorine, bromine, methyl, ethyl, propyl, isopropyl, monofluoroethyl, difluoromethyl, or trifluoromethyl.

4. The compound, or the pharmaceutically acceptable salt, solvate, or stereoisomer thereof of claim 1, wherein the substituted or unsubstituted $C_{3-10}$ heterocyclic ring is a substituted or unsubstituted 9-10 membered bicyclic heteroaryl ring containing 1, 2 or 3 nitrogen atoms and is selected from the group consisting of:

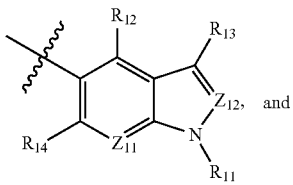

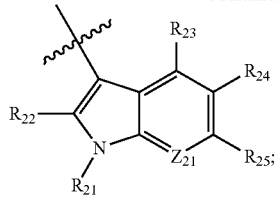

wherein $Z_{11}$ is $CR_{15}$ or N; $Z_{12}$ is $CR_{16}$ or N; $Z_{21}$ is $CR_{26}$ or N;

$R_{12}$, $R_{13}$, $R_{14}$, $R_{15}$, $R_{16}$, $R_{22}$, $R_{23}$, $R_{24}$, $R_{25}$, and $R_{26}$ are each independently H, hydroxy, CN, $NO_2$, halogen, $C_{1-3}$ haloalkyl, $C_{1-3}$ alkyl, —CON ($C_{1-3}$ alkyl)$_2$, —N($C_{1-3}$ alkyl)$_2$, —C(O)O$C_{1-3}$ alkyl, —OC(O)$C_{1-3}$ alkyl, —CO$C_{1-3}$ alkyl, —CO-phenyl, —$SO_2C_{1-3}$ alkyl, —$SO_2$-phenyl, —S(O)$C_{1-3}$ alkyl, or —S(O)-phenyl; wherein phenyl are unsubstituted or substituted with 1 to 3 substituents selected from the group consisting of fluorine, chlorine, and methyl; and $R_{11}$ and $R_{21}$ are each independently H, $C_{1-3}$ haloalkyl, $C_{1-3}$ alkyl, —CO$C_{1-3}$ alkyl, —CO-phenyl, —$SO_2C_{1-3}$ alkyl, or —$SO_2$-phenyl; wherein phenyl is unsubstituted or substituted with 1 to 3 substituents selected from the group consisting of: fluorine, chlorine, and methyl.

5. The compound, or the pharmaceutically acceptable salt, solvate, or stereoisomer thereof of claim 1, wherein the substituted or unsubstituted $C_{3-10}$ heterocyclic ring is a substituted or unsubstituted 5-6 membered monocyclic heteroaryl ring containing 1-2 nitrogen atoms and is selected from the group consisting of:

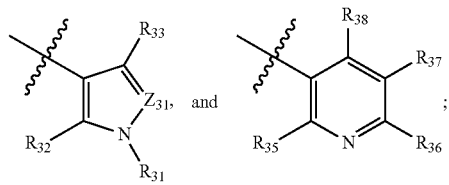

wherein $Z_{31}$ is $CR_{34}$ or N;

$R_{32}$, $R_{33}$, $R_{34}$, $R_{35}$, $R_{36}$, $R_{37}$, and $R_{38}$ are each independently H, hydroxy, CN, $NO_2$, halogen, $C_{1-3}$ haloalkyl, $C_{1-3}$ alkyl, —CON($C_{1-3}$ alkyl)$_2$, —N($C_{1-3}$ alkyl)$_2$, —C(O)O$C_{1-3}$ alkyl, —OC(O)$C_{1-3}$ alkyl, —CO$C_{1-3}$ alkyl, —CO-phenyl, —$SO_2C_{1-3}$ alkyl, —$SO_2$-phenyl, —S(O)$C_{1-3}$ alkyl, or —S(O)-phenyl;

wherein phenyl is unsubstituted or substituted with 1 to 3 substituents selected from the group consisting of fluorine, chlorine, and methyl; and $R_{31}$ is H, $C_{1-3}$ haloalkyl, $C_{1-3}$ alkyl, —CO$C_{1-3}$ alkyl, —CO-phenyl, —$SO_2C_{1-3}$ alkyl, or —$SO_2$-phenyl; wherein phenyl is unsubstituted or substituted with 1 to 3 substituents selected from the group consisting of fluorine, chlorine, and methyl.

6. The compound, or the pharmaceutically acceptable salt, solvate, or stereoisomer thereof of claim 1, wherein the substituted or unsubstituted $C_{3-10}$ heterocyclic ring is a substituted or unsubstituted 4-7 membered saturated monocyclic heterocyclic ring containing one nitrogen atom and is selected from the group consisting of:

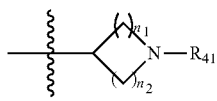

wherein $n_1$ is 1, 2 or 3; $n_2$ is 1 or 2; and $R_{41}$ is H, $C_{1-3}$ alkyl, $C_{1-3}$ haloalkyl, —$COC_{1-3}$ alkyl, —CO-phenyl, —$SO_2C_{1-3}$ alkyl, —$SO_2$-phenyl, —$S(O)C_{1-3}$ alkyl, or —S(O)-phenyl; wherein phenyl is unsubstituted or substituted with 1 to 3 substituents selected from the group consisting of fluorine, chlorine, and methyl.

7. The compound, or the pharmaceutically acceptable salt, solvate, or stereoisomer thereof of claim 4, wherein, the compound of formula (I) is a compound of formula (II) or formula (III):

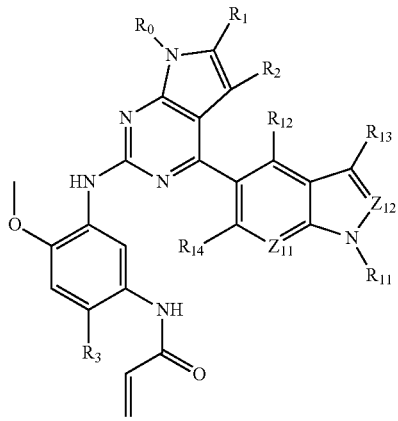

II wherein $R_{11}$, $R_{12}$, $R_{13}$, $R_{14}$, $R_0$, $R_1$, $R_2$, $R_3$, $Z_{11}$, and $Z_{12}$ are defined as in claim 4;

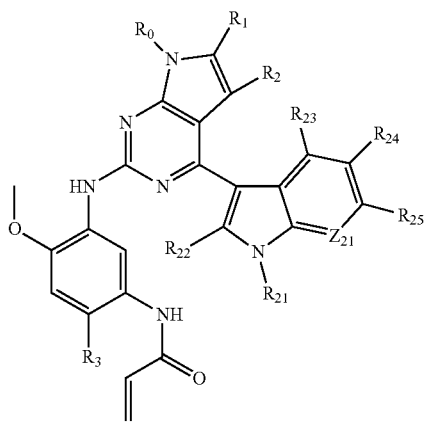

III wherein $R_{21}$, $R_{22}$, $R_{23}$, $R_{24}$, $R_{25}$, $R_0$, $R_1$, $R_2$, $R_3$, and $Z_{21}$ are defined as in claim 4.

8. The compound, or the pharmaceutically acceptable salt, solvate, or stereoisomer thereof of claim 1, wherein the substituted or unsubstituted $C_{3-10}$ heterocyclic ring is:

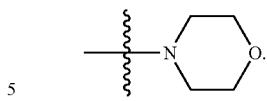

9. The compound, or the pharmaceutically acceptable salt, solvate, or stereoisomer thereof of claim 1, wherein the substituted or unsubstituted $C_{6-10}$ aryl ring is:

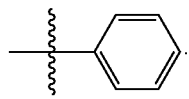

10. The compound, or the pharmaceutically acceptable salt, solvate, or stereoisomer thereof of claim 1, wherein the compound of formula (I) is a compound of formula (VII) or formula (VIII):

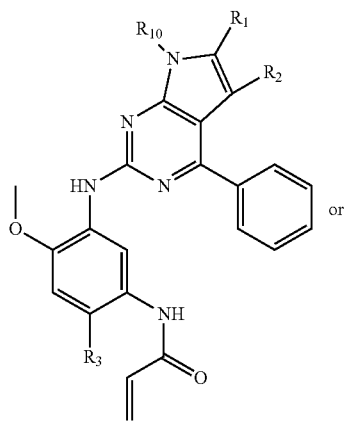

VII or

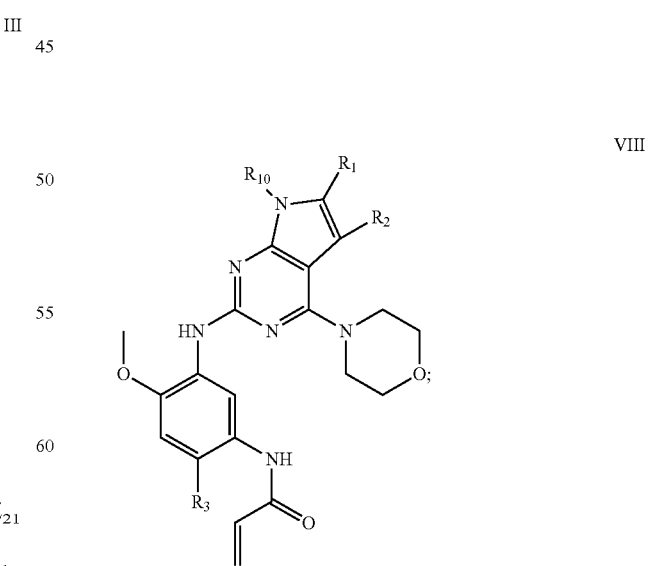

VIII wherein $R_0$, $R_1$, $R_2$, and $R_3$ are defined as in claim 1.

11. A compound selected from the group consisting of:
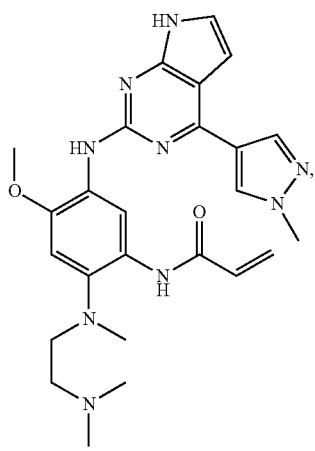
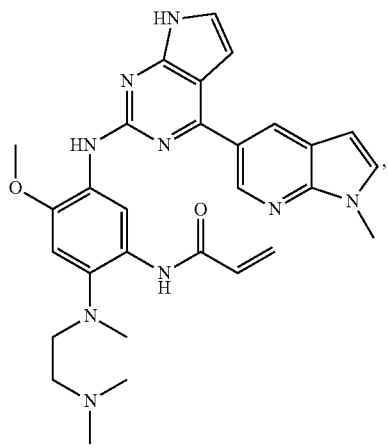
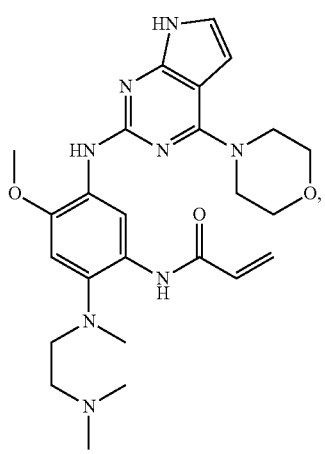
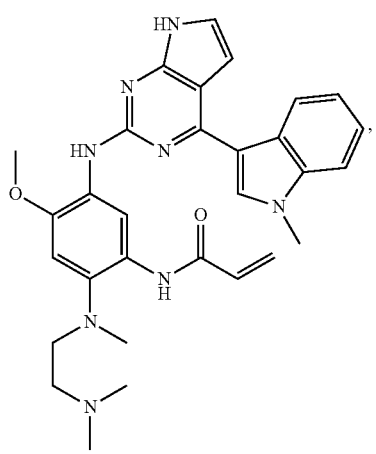
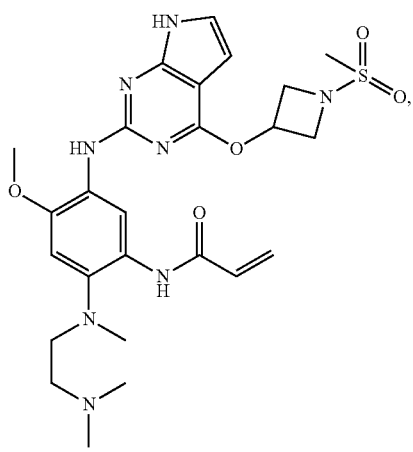
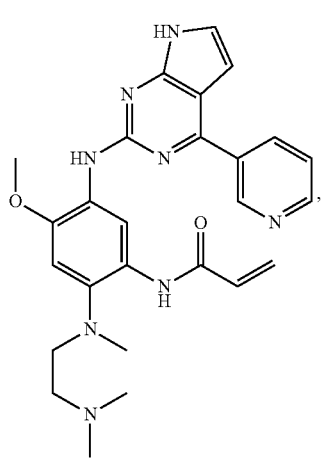

97
-continued
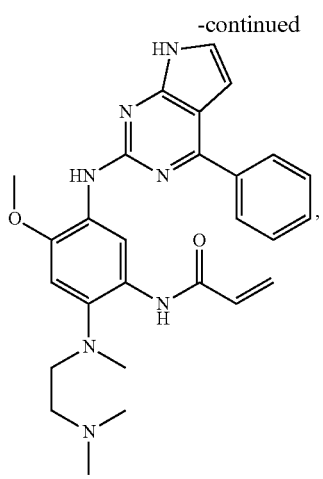
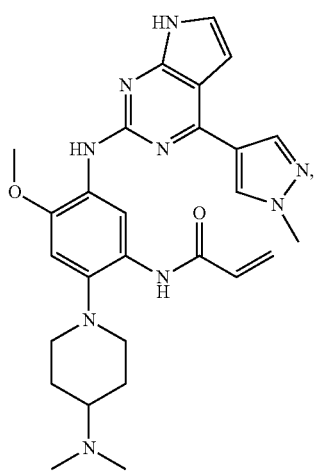
98
-continued
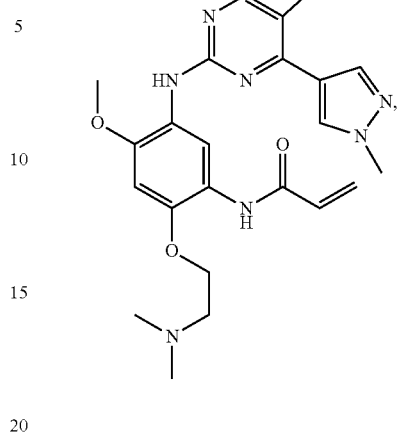
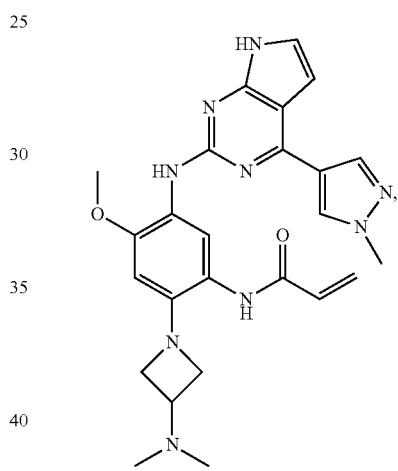
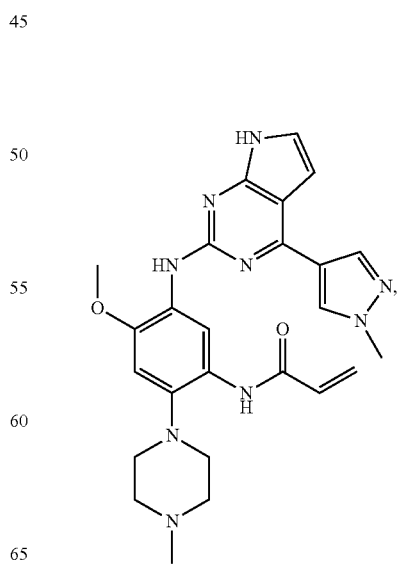

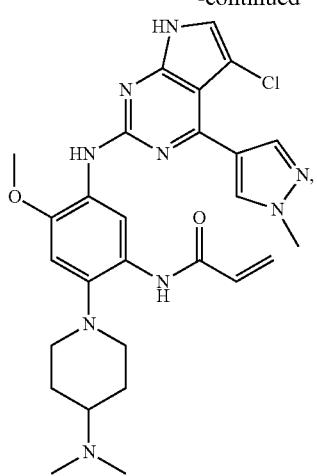

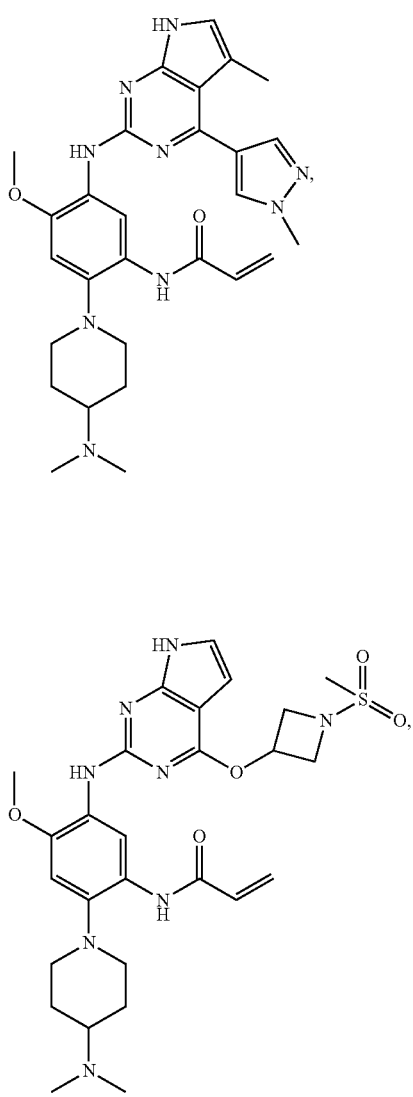

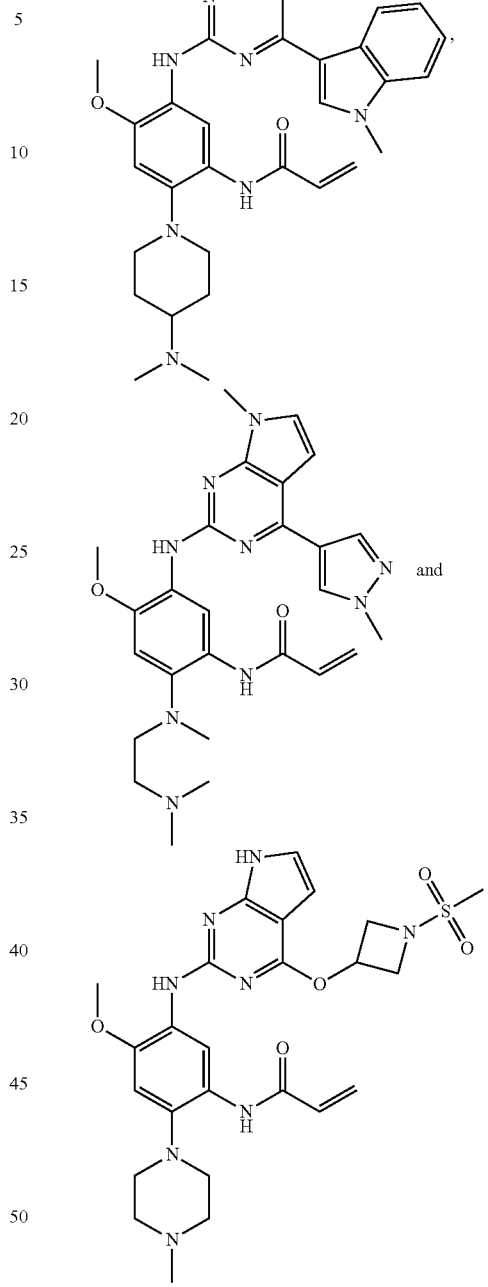

or a pharmaceutically acceptable salt, solvate, or stereoisomer thereof.

12. A pharmaceutical composition comprising the compound, or the pharmaceutically acceptable salt, solvate, or stereoisomer thereof according to claim 1, and a pharmaceutically acceptable carrier.

13. A medicinal composition comprising the compound, or the pharmaceutically acceptable salt, solvate, or stereoisomer thereof according to claim 1; and one or more medicaments selected from the group consisting of gefitinib, erlotinib, erlotinib, lapatinib, XL647, NVP-AEE-788, ARRY-334543, EKB-569, BIBW2992, HKI272, BMS-690514, CI-1033, vandetanib, PF00299804, WZ4002, cetuximab, trastuzumab, panitumumab, matuzumab, nimotuzumab, zalutumumab, pertuzumab, MDX-214, CDX-110, IMC-11F8, Zemab, Her2 vaccine PX 1041, HSP90 inhibitor, CNF2024, tanespimycin, alvespimycin, IPI-504, SNX-5422, and NVP-AUY922.

14. A method for preparing the compound of formula (I), or a pharmaceutically acceptable salt, solvate, or stereoisomer thereof according to claim 1, wherein
the method comprises the following steps:
(i) subjecting a compound of formula I-f to a reduction reaction to form a compound of formula I-g; and
(ii) subjecting the compound of formula I-g and acryloyl chloride to a condensation reaction to form the compound of formula (I);

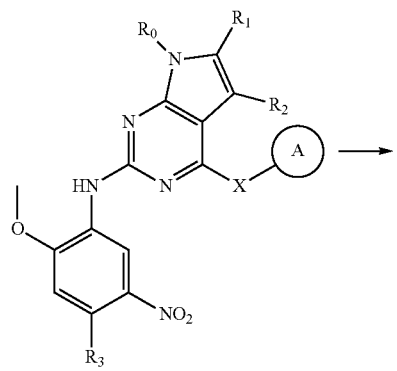

I-f

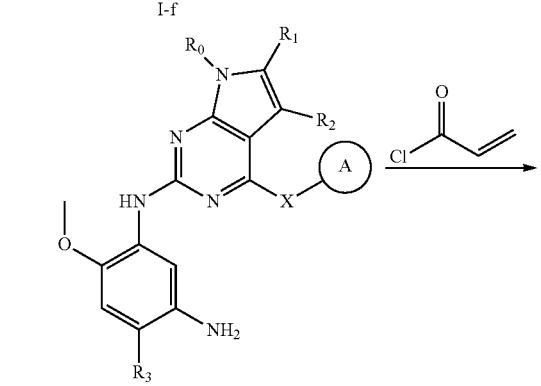

I-g

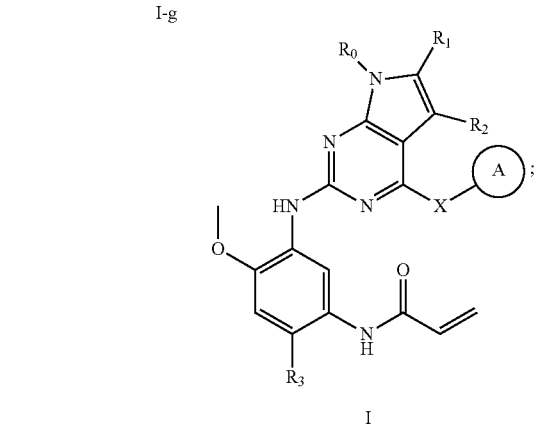

I or the method comprises step (i'): allowing a compound of formula I-c to react with a compound of formula I-h in an inert solvent to form the compound of formula (I);

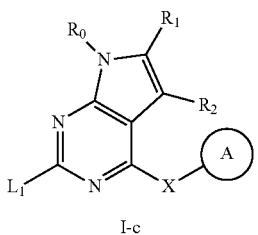

I-c

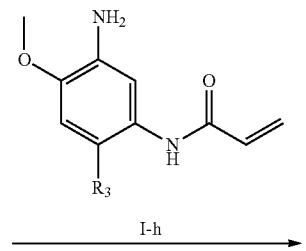

I-h

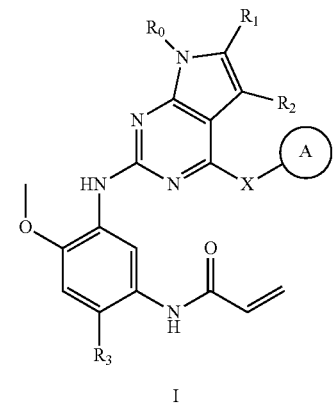

I wherein in each of the above formulas, $R_0$, $R_1$, $R_2$, $R_3$, X, and A ring are defined as in claim 1; and $L_1$ is a leaving group.

15. The compound, or the pharmaceutically acceptable salt, solvate, or stereoisomer thereof of claim 5, wherein the compound of formula (I) is a compound of formula (IV) or formula (V):

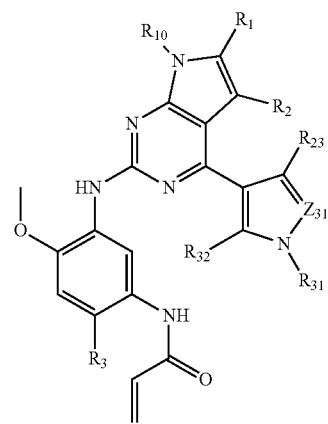

IV wherein R$_{31}$, R$_{32}$, R$_{33}$, R$_0$, R$_1$, R$_2$, R$_3$, and Z$_{31}$ are defined as in claim 5;

V

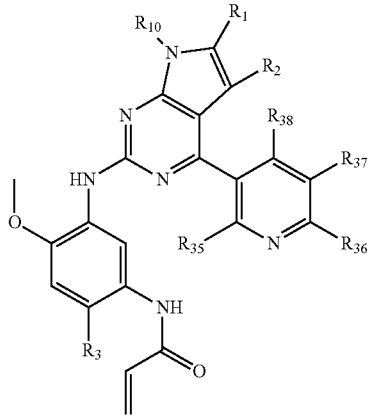

wherein R$_{35}$, R$_{36}$, R$_{37}$, R$_{38}$, R$_0$, R$_1$, R$_2$, and R$_3$ are defined as in claim 5.

16. The compound, or the pharmaceutically acceptable salt, solvate, or stereoisomer thereof of claim 6, wherein, the compound of formula (I) is a compound of formula (VI):

VI

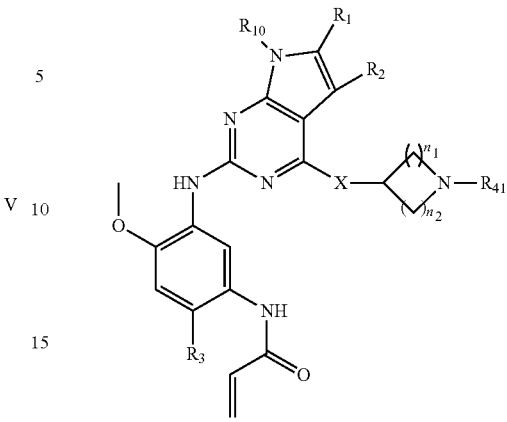

wherein R$_{41}$, R$_0$, R$_1$, R$_2$, R$_3$, X, n$_1$, and n$_2$ are defined as in claim 6.

17. A method of inhibiting EGFR tyrosine kinase activity in a subject in need thereof, the method comprising administering to the subject the pharmaceutical composition of claim 12.

18. A method of treating an EGFR-related disease in a subject in need thereof, the method comprising administering to the subject the pharmaceutical composition of claim 12, wherein the EGFR-related disease is a cancer selected from the group consisting of gastric cancer, non-small cell lung cancer, esophageal cancer, and pancreatic cancer.

19. The method of claim 17, wherein the EGFR tyrosine kinase comprises a T790M mutation.

20. A pharmaceutical composition comprising the compound, or the pharmaceutically acceptable salt, solvate, or stereoisomer thereof according to claim 11, and a pharmaceutically acceptable carrier.

* * * * *